(12) United States Patent
Benedetti et al.

(10) Patent No.: US 9,707,217 B1
(45) Date of Patent: Jul. 18, 2017

(54) DOSE-DUMPING RESISTANT CONTROLLED RELEASE DOSAGE FORM

(71) Applicant: OSMOTICA KERESKEDELMI ES SZOLGALTATO KFT, Budapest (HU)

(72) Inventors: Hernan D. Benedetti, Buenos Aires (AR); Cristian R. Franco, Buenos Aires (AR); Guido S. Bigatti, Madrid (ES); Joaquina Faour, Buenos Aires (AR); Ana C. Pastini, Buenos Aires (AR)

(73) Assignee: Osmotica Kereskedelmi es Szolgaltato KFT, Budapest (HU)

( * ) Notice: Subject to any disclaimer, the term of this patent is extended or adjusted under 35 U.S.C. 154(b) by 0 days.

(21) Appl. No.: 15/424,134

(22) Filed: Feb. 3, 2017

Related U.S. Application Data

(60) Provisional application No. 62/454,269, filed on Feb. 3, 2017.

(51) Int. Cl.

| | | |
|---|---|---|
| *A61K 31/4458* | (2006.01) | |
| *A61K 9/00* | (2006.01) | |
| *A61K 9/24* | (2006.01) | |
| *A61K 9/28* | (2006.01) | |
| *A61K 9/20* | (2006.01) | |

(52) U.S. Cl.
CPC ........ *A61K 31/4458* (2013.01); *A61K 9/0004* (2013.01); *A61K 9/209* (2013.01); *A61K 9/2009* (2013.01); *A61K 9/2013* (2013.01); *A61K 9/2031* (2013.01); *A61K 9/2054* (2013.01); *A61K 9/2866* (2013.01); *A61K 9/2886* (2013.01)

(58) Field of Classification Search
CPC .. A61K 31/197; A61K 9/0004; A61K 9/0053; A61K 9/006; A61K 9/145; A61K 9/146; A61K 9/20; A61K 9/2031; A61K 9/2866
See application file for complete search history.

(56) References Cited

U.S. PATENT DOCUMENTS

| | | |
|---|---|---|
| 3,625,214 A | 12/1971 | Higuchi |
| 4,036,227 A | 7/1977 | Zaffaroni |
| 4,142,526 A | 3/1979 | Zaffaroni |
| 4,200,098 A | 4/1980 | Ayer |
| 4,285,987 A | 8/1981 | Ayer |
| 4,449,983 A | 5/1984 | Cortese |
| 4,576,604 A | 3/1986 | Guittard |
| 4,612,008 A | 9/1986 | Wong |
| 4,673,405 A | 6/1987 | Guittard |
| 4,814,181 A | 3/1989 | Jordan |
| 4,874,388 A | 10/1989 | Wong |

(Continued)

OTHER PUBLICATIONS

English translation of CN1209098C, Jul. 2005; 13 pages.*
English translaton of CN104739797, Jul. 2015; 10 pages.*

*Primary Examiner* — Ernst V Arnold
(74) *Attorney, Agent, or Firm* — Rick Matos; Innovar, L.L.C.

(57) ABSTRACT

The present invention provides a simple and improved dose form that is capable of providing a controlled release of methylphenidate contained in the core thereof. The invention also provides methods of administering the dosage form and of treating conditions that are therapeutically responsive to methylphenidate. The dosage form exhibits improved resistance to alcohol-related dose dumping.

29 Claims, 20 Drawing Sheets

(56) References Cited

U.S. PATENT DOCUMENTS

| | | | |
|---|---|---|---|
| 4,892,778 | A | 1/1990 | Theeuwes |
| 4,915,954 | A | 4/1990 | Ayer |
| 4,940,465 | A | 7/1990 | Theeuwes |
| 4,957,494 | A | 9/1990 | Wong |
| 5,156,850 | A | 10/1992 | Wong |
| 5,178,866 | A | 1/1993 | Wright |
| 5,232,705 | A | 8/1993 | Wong |
| 5,474,786 | A | 12/1995 | Kotwal |
| 5,558,879 | A | 9/1996 | Chen |
| 5,593,694 | A | 1/1997 | Hayashida |
| 5,785,994 | A * | 7/1998 | Wong |
| 6,919,373 | B1 * | 7/2005 | Lam .................... A61K 9/0004 514/532 |
| 6,930,129 | B2 | 8/2005 | Lam |
| 8,163,798 | B2 | 4/2012 | Gupta |
| 8,629,179 | B2 | 1/2014 | Gupta |
| 9,000,038 | B2 | 4/2015 | Lam |
| 9,029,416 | B2 | 5/2015 | Lam |
| 9,144,549 | B2 | 9/2015 | Gupta |

\* cited by examiner (fasted)

(fed)

DOSE-DUMPING RESISTANT CONTROLLED RELEASE DOSAGE FORM

CROSS-REFERENCE TO EARLIER FILED APPLICATION

The present application claims the benefit of provisional application No. 62/454,269 filed Feb. 3, 2017, the entire disclosure of which is hereby incorporated by reference.

FIELD OF THE INVENTION

This invention pertains to a delivery device for the controlled delivery of methylphenidate to a subject in need thereof. More particularly, it pertains to a controlled release dosage form, wherein the dosage form exhibits improved resistance to alcohol-related dose-dumping. Methods of use and preparation thereof are also provided.

BACKGROUND OF THE INVENTION

Methylphenidate (MPH, methyl 2-phenyl-2-(piperidin-2-yl)acetate, a $5HT_{1A}$ receptor agonist) is sold under the trademarks RITALIN, CONCERTA®, APTENSIO, BIPHENTIN, DAYTRANA, EQUASYM, MEDIKINET, METADATE, METHYLIN, QUILLIVANT and others. It is commonly used for the treatment of attention deficit hyperactivity disorder (ADHD), narcolepsy, and for off-label use in the treatment of postural orthostatic tachycardia syndrome, lethargy, fatigue, bipolar disorder, lack of attention (lack of attentiveness), opioid induced somnolence, major depressive disorder and obesity. It has a plasma half-life of about 2-3 hours, so immediate or rapid release dosage forms are typically administered two to four times daily. Common dosage forms include conventional tablets, capsules, chewable tablets and oral solutions, which are indicated as needing to be administered 30-45 min before a meal. MPH can be administered alone or can be administered as adjunct therapy.

There is the possibility of developing dependence upon MPH (a Schedule II drug), especially if it is abused. Consuming alcohol (ethanol or a beverage containing ethanol) is one way to enhance the bioavailability of MPH by up to 40% (Patrick et al., "Influence of ethanol and gender on methylphenidate pharmacokinetics and pharmacodynamics" in Clin. Pharm. Thera. (March 2007), 81(3), 346-353). Too rapid of a release of MPH will result in too high of a Cmax, too short of a Tmax, increased adverse events and increased release of dopamine, which results in a euphoric effect and thus leads to abuse and addiction. In fact, ethylphenidate can be formed in vivo after ingestion of ethanol and MPH (Markowitz et al., "Detection of the novel metabolite ethylphenidate after methylphenidate overdose with alcohol coingestion", in J. Clin. Psychopharm. (1999), 19(4), 362-366). There is a need to provide extended release dosage forms that are resistant to such alcohol ingestion-related dose dumping.

In view of the short half-life of MPH, extended release tablet, capsule, powder, particle and osmotic device dosage forms have been developed: METADATE-ER, RITALIN-SR, APTENSIO-XR, METADATE-CD, RITALIN-LA, CONCERTA®, QUILLIVANT-XR. Even transdermal dosage forms are available. Extended release dosage forms include higher doses of MPH and, so, are useful for reducing the total number of daily doses required. Extended release dosage forms containing MPH have been suggested by or disclosed in the patent literature: U.S. Pat. No. 4,285,987, U.S. Pat. No. 4,200,098, U.S. Pat. No. 5,558,879, U.S. Pat. No. 4,449,983, U.S. Pat. No. 4,576,604, U.S. Pat. No. 4,673,405, U.S. Pat. No. 5,593,694, U.S. Pat. No. 3,625,214, U.S. Pat. No. 4,814,181, U.S. Pat. No. 5,474,786, U.S. Pat. No. 4,892,778, U.S. Pat. No. 4,940,465, U.S. Pat. No. 4,915,954, U.S. Pat. No. 4,874,388, U.S. Pat. No. 4,957,494, U.S. Pat. No. 5,156,850, U.S. Pat. No. 5,232,705, U.S. Pat. No. 5,785,994, U.S. Pat. No. 4,612,008, U.S. Pat. No. 5,178,866, U.S. Pat. No. 4,142,526, U.S. Pat. No. 4,036,227, U.S. Pat. No. 9,144,549, U.S. Pat. No. 8,629,179, U.S. Pat. No. 8,163,798, U.S. Pat. No. 6,930,129, U.S. Pat. No. 6,919,373.

Literature reports, however, that some oral extended release dosage forms may exhibit dose dumping when coadministered orally with an alcoholic beverage (Meisner et al. "Extended release stimulant medication misuse with alcohol co-administration", in J. Can. Acad. Child Adolesc. Psychiatry (November 2008), 17(4), 181-182). For example, literature reports that extended release capsules but not CONCERTA®, an OROS® osmotic device with a tri-layered core, exhibit dose dumping in vitro when placed in alcoholic solution. 98 or 84% of the drug was released from RITALIN LA (40-mg) or METADATE CD (60-mg) capsules within the first hour at an alcohol concentration of 40% (UCB, Inc. METADATE CD once-daily MPH HCl extended-release capsules prescribing information, Smyrna, G A, 2015 February; Novartis, RITALIN LA MPH HCl extended-release capsules prescribing information, East Hanover, N J, 2015 July). 96% was released from APTENSIO XR (80-mg) capsules within 2 hours at an alcohol concentration up to 40% (Rhodes Pharmaceuticals, APTENSIO XR MPH HCl extended-release capsules prescribing information, Coventry, R I, 2015 April; Janssen Pharmaceuticals, Inc. CONCERTA® MPH HCl extended-release tablets prescribing information, Titusville, N.J.; 2015 April).

The product insert for CONCERTA® osmotic devices, which provide an ascending release rate for MPH over a period of at least 5-6 h, includes a comparative summary of the pharmacokinetic parameters for a single 18 mg dose of CONCERTA® once daily versus a 5 mg dose of rapid release tablet three times daily.

| Parameter | CONCERTA® 18 mg 1× daily | MPH 5 mg 3× daily |
| --- | --- | --- |
| Cmax (ng/mL) | 3.7 ± 1.0 | 4.2 ± 1.0 |
| Tmax (h) | 6.8 ± 1.8 | 6.5 ± 1.8 |
| AUCinf (ng-g/mL) | 41.8 ± 13.9 | 38.0 ± 11.0 |
| T1/2 (h) | 3.5 ± 0.4 | 3.0 ± 0.5 |

The comparative plasma profiles are depicted in FIG. 1. The product literature also reports no food effect and no food-related dose-dumping.

Even though the literature asserts that oral ingestion of alcohol results in no alcohol-related dose-dumping effect upon release of MPH from CONCERTA® osmotic devices, the present inventors have found substantial evidence to the contrary. It would be a significant addition to the art to provide a controlled release dosage form suitable for once or twice daily oral administration that still provides therapeutic levels of MPH for an extended period of time while concomitantly reducing the potential for dose-dumping caused by ethanol.

There are other dosage form known to exhibit alcohol-related dose-dumping. Such dosage forms typically contain a narcotic or other abusable drug as the therapeutic agent or active ingredient. It would be a significant advancement in the art to provide a controlled release dosage form suitable for once or twice daily oral administration that provides therapeutic levels of the narcotic for an extended period of time while concomitantly reducing the potential for dose-dumping caused by ethanol.

SUMMARY OF THE INVENTION

The invention provides a controlled release oral dosage form comprising an abusable drug, such as a narcotic, suitable for once or twice daily oral administration to a subject in need thereof for the treatment of a disease, disorder or condition that is therapeutically responsive to the abusable drug. The controlled release dosage form provides substantially improved resistance toward ethanol-related dose-dumping as compared to other controlled release dosage forms containing the same abusable drug.

The invention provides a controlled release oral dosage form comprising methylphenidate (MPH) suitable for once or twice daily oral administration to a subject in need thereof for the treatment of a disease, disorder or condition that is therapeutically responsive to MPH. The invention also provides methods of use thereof. The invention provides improved efficacy and safety profiles for drugs when administered as described herein. The controlled release dosage form provides substantially improved resistance toward ethanol-related dose-dumping as compared to CONCERTA® osmotic device formulations (as described in: Food & Drug Administration (FDA) New Drug Application (NDA) No. N021121— dosage strengths 18 mg, 36 mg, 54 mg, 27 mg; and U.S. Pat. No. 6,919,373, U.S. Pat. No. 6,930,129, U.S. Pat. No. 8,163,798, U.S. Pat. No. 8,629,179, U.S. Pat. No. 9,000,038, U.S. Pat. No. 9,029,416, and U.S. Pat. No. 9,144,549).

The present invention overcomes some of the disadvantages of the art by providing a controlled release oral dosage form comprising a core comprising at least one abusable drug (e.g. MPH) and at least one pharmaceutical excipient, and a coating surrounding (enclosing) the core, wherein the dosage form exhibits reduced ethanol-related dose-dumping in vitro when placed in an aqueous alcohol solution.

An osmotic device of the invention exhibits enhanced resistance to ethanol-related dose-dumping, wherein the osmotic device provides a less than 1.5-fold ethanol-related increase in the total amount of abusable drug (e.g. MPH) released from the core during the first 120 min after placement in an aqueous environment when comparing the drug release rates in 0.1 N HCl and in 40% ethanol in 0.1 N HCl.

The osmotic device exhibits enhanced resistance to ethanol-related dose-dumping, wherein the osmotic device provides a less than 2-fold ethanol-related increase in the average rate of abusable drug (e.g. MPH) released from the core during the time period of 15 min to 120 min after placement in an aqueous environment when comparing the release rates in 0.1 N HCl and in 40% ethanol in 0.1 N HCl.

In some embodiments, the dosage form comprises: a) a core comprising at least one abusable drug (e.g. MPH) and at least one excipient, b) a semipermeable membrane surrounding the core and comprising at least one preformed passageway. In some embodiments, the controlled release oral dosage form is an osmotic device.

In some embodiments, the controlled release oral dosage form comprises: a) a core comprising at least one abusable drug (e.g. MPH) and at least one water-swellable excipient, b) a semipermeable membrane surrounding the core and comprising at least one film-forming cellulose ester and at least one preformed passageway.

Some embodiments of the invention those wherein: a) the core comprises at least one abusable drug (e.g. MPH) and at least two water-swellable excipients, and the semipermeable membrane surrounding the core comprises at least one film-forming cellulose ester and at least one preformed passageway; b) the core comprises at least one abusable drug (e.g. MPH) and at least two water-swellable excipients, and the semipermeable membrane comprises at least one film-forming cellulose ester, at least one plasticizer, and at least one preformed passageway; or c) the core comprises at least one abusable drug (e.g. MPH), at least two water-swellable excipients, and at least one binder, and the semipermeable membrane comprises one type or grade of film-forming cellulose ester, at least one plasticizer and at least one preformed passageway.

In some embodiments, the core is a bi-layered core comprising: a) a drug-containing pull layer and a water swellable push layer; b) a drug-containing pull layer and an inert (non-drug-containing) water swellable push layer; or c) a water swellable drug-containing pull layer and a water swellable push layer.

In embodiments wherein the core comprises a drug-containing pull layer and a water swellable push layer: a) the weight of the pull layer is higher than the weight of the push layer; b) the weight of the pull layer is lower than the weight of the push layer; or c) the weight of the pull layer is about the same as the weight of the push layer.

In some embodiments, the at least one water-swellable excipient: a) is a water swellable natural, synthetic or semi-synthetic polymer; b) comprises a single grade or type of polymer; c) comprises two different grades of the same type of polymer, meaning the two grades share the same general chemical structure but differ in one or more physical properties; d) comprises two different types of polymer, meaning the two polymers have different general chemical structure (made from different monomer(s)) and differ in one or more physical properties; e) comprises a combination of a cellulose derivative and polyalkylene oxide (PAO); f) comprises a combination of hydroxypropyl methylcellulose (HPMC, which is a hydroxyalkyl alkylcellulose) and polyethylene oxide (PEO, which is a polyalkylene oxide); g) comprises a major portion (majority) of a first grade and a minor portion (minority) of a second grade of the same type of polymer; h) comprises a major portion of a first type and a minor portion of a second type of polymer; i) comprises a major portion of PEO and a minor portion of HPMC; or j) is a combination or one or more of the above.

In some embodiments, the pull layer comprises at least one water swellable polymer and the water swellable push layer comprises at least one water swellable polymer. In some embodiments, the pull layer comprises at least two water swellable polymers and the water swellable push layer comprises at least two water swellable polymers. When two water swellable polymers are present in a respective layer, the polymers can be of two different types (made from different monomer(s)) or two different grades (made from the same monomers but exhibiting different physical properties).

In some embodiments, the pull layer comprises PAO and cellulose derivative, and/or the water swellable push layer comprises PAO and cellulose derivative. In some embodiments, the viscosity and molecular weight of the PAO in the pull layer is lower than that of the PAO in the push layer. In some embodiments, the viscosity and molecular weight of the cellulose derivative in the pull layer is lower than that of the cellulose derivative in the push layer. In some embodiments, the grade of cellulose derivative in the pull layer is substantially the same as the grade of cellulose derivative in the push layer. In some embodiments, the grade of PAO in the pull layer is different than the grade of PAO in the push layer.

In some embodiments, the pull layer comprises at least one abusable drug (e.g. MPH), water swellable PAO polymer, hydrophilic cellulose derivative, and acidic agent. In some embodiments, the water swellable push layer comprises water swellable PAO polymer, hydrophilic cellulose derivative, and osmotic salt.

In some embodiments, the extended release dosage form comprises a core enclosed within a semipermeable membrane, wherein:
the core comprises:
 a) a pull layer comprising at least one abusable drug (e.g. MPH), first water swellable PAO polymer, and first hydrophilic cellulose derivative; and
 b) a water swellable push layer comprising second water swellable PAO polymer, and second hydrophilic cellulose derivative;
the membrane comprises at least one preformed passageway, at least one film-forming cellulose ester, and at least one plasticizer.

In some embodiments, the extended release dosage form comprises a core enclosed within a semipermeable membrane, wherein:
the core comprises:
 a) a pull layer comprising at least one abusable drug (e.g. MPH), first water swellable PAO polymer, first hydrophilic cellulose derivative, and acidic agent; and
 b) a water swellable push layer comprising second water swellable PAO polymer, second hydrophilic cellulose derivative, and osmotic salt;
the membrane comprises at least one preformed passageway, at least one film-forming cellulose ester, and at least one plasticizer.

In some embodiments, the dosage form further comprises a drug-containing coating exterior to the membrane. The drug in this coating can be the at least one abusable drug (e.g. MPH), another drug or a combination thereof. This coating can be an immediate release or rapid release coating. If the abusable drug is present in the coating, the amount of abusable drug in the coating is less than amount of abusable drug in the core.

In some embodiments, the dosage form further comprises an immediate or rapid release composition comprising at least one abusable drug (e.g. MPH). In some embodiments, the dosage form: a) comprises a drug-containing coat exterior to the semipermeable membrane; b) comprises an inert water soluble or erodible coat composition surrounding the semipermeable membrane and between the semipermeable membrane and another coat; c) comprises one or more compression coatings and one or more sprayed-on coatings or membranes exterior to the semipermeable membrane; d) excludes a drug-containing coat exterior to the semipermeable membrane; e) comprises an inert water soluble or erodible coat external to the semipermeable membrane; or f) comprises at least any two of the above.

In some embodiments, the amount of PAO in the pull layer is higher than the amount of cellulose derivative in the pull layer. In some embodiments, the amount of PAO in the push layer is higher than the amount of cellulose derivative in the push layer. In some embodiments, the amount of PAO in the pull layer is lower than the amount of cellulose derivative in the pull layer. In some embodiments, the amount of PAO in the push layer is lower than the amount of cellulose derivative in the push layer.

In some embodiments, the cellulose derivative is selected from the group consisting of alkylcellulose, hydroxyalkylcellulose and hydroxyalkyl alkylcellulose. In some embodiments, alkyl is independently upon each occurrence selected from the group consisting of methyl, ethyl or propyl (n-propyl or i-propyl).

In some embodiments, the at least one abusable drug (e.g. MPH) is independently upon each occurrence: a) present in salt form; b) present in freebase form; c) present in prodrug form; or d) present as a combination of one or more of the above. Some embodiments exclude a prodrug form of the at least one abusable drug (e.g. MPH). Some embodiments exclude a salt form of the at least one abusable drug (e.g. MPH).

In some embodiments, the at least one osmotic salt: a) does not have an ion in common with the abusable drug (MPH) salt; b) has an ion in common with the abusable drug (MPH) salt; c) is a halide salt; or d) is a combination of one or more of the above.

In some embodiments, the film-forming cellulose ester: a) comprises a single type and grade of cellulose ester polymer; b) comprises a combination of at least two different grades of the same type of cellulose ester polymer; c) comprises a combination of two different types of cellulose ester polymer; d) comprises at least one cellulose acetate polymer; e) comprises at least two different grades of cellulose acetate polymer; f) comprises at least as cellulose acetate Grade 1 (Polymer 1) and Grade 2 (Polymer 2); g) has a formulation as described herein; or h) is a combination of one or more of the above.

In embodiments wherein at least two grades or types of film-forming cellulose ester are present in the membrane: a) the amount of a first grade is higher than the amount of a second grade; b) the amount of a first type is higher than the amount of a second type; c) the amount of a first grade is about the same as the amount of a second grade; d) the amount of a first type is about the same as the amount of a second type; or e) a combination thereof.

In some embodiments, the membrane further comprises at least one plasticizer, and the amount of plasticizer is less than the total amount of film-forming cellulose ester.

In some embodiments, the semipermeable membrane does not rupture within 10 hours after placement in an aqueous environment of use.

In some embodiments, the core: a) further comprises at least one binder; b) further comprises at least one filler; c) further comprises at least one antioxidant; d) further comprises at least one glidant; e) further comprises at least one lubricant; f) has a formulation as described herein; g) is a bi-layered core; h) is a compressed composition; i) excludes a composition or coat or layer between the core and the semipermeable membrane; or j) is a combination of one or more of the above.

In some embodiments, the dosage form: a) provides a controlled release of MPH from the core for a period of at least 8 h, at least 10 h, at least 12 h, at least 16 h, at least 20 h and/or up to 24 hours after administration; b) provides a release of MPH from the core characterized by an in vitro first order, pseudo-first order, zero order or pseudo-zero order dissolution profile determined as described herein; and/or c) provides a plasma profile defined by the pharmacokinetic parameters described herein. Some embodiments exclude a dosage form that releases MPH from the core according to a release profile exhibiting an ascending MPH release rate over an extended period of time, e.g. a period of at least 4 h, at least 5 h, at least 6 h, at least 7 hours or at least 8 h.

The present invention further provides a method for treating a condition, disorder or disease that is therapeutically responsive to the abusable drug (e.g. MPH), the method comprising administering a controlled release dosage form as described herein. In some embodiments, the condition, disease or disorder is selected from the group consisting of attention deficit hyperactivity disorder (ADHD), narcolepsy, postural orthostatic tachycardia syndrome, lethargy, fatigue, bipolar disorder, lack of attention (lack of attentiveness), opioid induced somnolence, major depressive disorder and obesity.

The dosage form of the invention can be administered in the fed state or in the fasting (fasted) state. In some embodiments, the dosage form exhibits little to no positive or negative food effect following oral administration as determined by comparison of Cmax, Tmax or $AUC_{0-t}$ for single dose administration to healthy subjects under fasted and fed conditions. The phrase "little to no" is taken to mean no more than a 10%, 20% or 30% difference in the observed Cmax or $AUC_{0-t}$ when comparing pharmacokinetics in the fed versus fasting states. The dosage form of the invention provides less food effect than that provided by CONCERTA® osmotic device when administered at equivalent doses and under the same conditions, especially as determined by comparison of Tmax.

In some embodiments, the extended release dosage form provides a reduced Cmax and/or AUC as compared to oral administration of a reference immediate release dosage form comprising the same dose of abusable drug (e.g. MPH). In some embodiments, the extended release dosage form provides a reduced Cmax and about the same AUC as compared to oral administration of a reference immediate release dosage form comprising the same dose of abusable drug (e.g. MPH) and still provides substantially the same or an improved clinical benefit over the immediate release dosage form.

In some embodiments where the dosage form is administered twice daily, a first dose is administered during the first 12-hour period of a 24-hour period, and a second dose is administered during the second 12-hr period of the same 24-hour period. In some embodiments where the dosage form is administered twice daily, the first and second doses are administered about 8 h to about 16 h, about 9 h to about 15 h, about 10 h to about 14 h, about 11 h to about 13 h or about 12 h (hours) apart. In some embodiments where the dosage form is administered twice daily, the first dose is administered in the morning hours, and the second dose is administered in the evening or nighttime hours. In some embodiments where the dosage form is administered twice daily, the first total daily dose is higher than the second total daily dose, or the first total daily dose is lower than the second total daily dose.

In some embodiments, the extended or controlled release dosage form of the invention provides a Cmax and AUC for the abusable drug (e.g. MPH) that is lower than that provided by an immediate release dosage form comprising the same molar amount of the abusable drug (e.g. MPH) and still provides substantially the same or an improved clinical benefit over the immediate release dosage form.

In some embodiments, the extended or controlled release dosage form of the invention provides a lower Cmax and about the same AUC for the abusable drug (e.g. MPH) as that provided by an immediate release dosage form comprising the same molar amount of the abusable drug (e.g. MPH) and still provides substantially the same or an improved clinical benefit over the immediate release dosage form.

The invention provides a method of treating an abusable drug-responsive (e.g. MPH-responsive) condition in a subject comprising orally administering one or more doses of abusable drug (e.g. MPH) in an extended (controlled) release dosage form per day, whereby less adverse events are observed than treatment with rapid release tablets MPH.

The invention also provides use of the dosage form for the treatment of a condition that is therapeutically responsive to the abusable drug (e.g. MPH) comprising administering one or more of the dosage forms as described herein to a subject in need thereof according to a dosing regimen as described herein.

The dosage form of the invention is administered orally once, twice or three-times daily, including daytime and/or nighttime administration.

The dosage form exhibits lower alcohol-related dose-dumping than the CONCERTA® osmotic device when equivalent doses and test conditions are used. In some embodiments, the instant osmotic device provides a less than 1.5-fold, less than 1.4-fold, less than 1.3-fold, less than 1.2-fold, less than 1.15 fold, less than 1.1-fold or less than 1.05-fold ethanol-related increase in the total amount of MPH released during the first 120 min, when comparing the release rates in aqueous 0.1 N HCl and in 40% ethanol in aqueous 0.1 N HCl. In some embodiments, the instant osmotic device provides a less than 2-fold, less than 1.8-fold, less than 1.7-fold, less than 1.6-fold, less than 1.5-fold, less than 1.4-fold, or less than 1.3-fold ethanol-related increase in the average rate of MPH release during the time period of 15 min to 120 min, when comparing the release rates of MPH in aqueous 0.1 N HCl and in 40% ethanol in aqueous 0.1 N HCl.

The invention includes all combinations of the aspects, embodiments and sub-embodiments disclosed herein. Other features, advantages and embodiments of the invention will become apparent to those skilled in the art by the following description, accompanying examples and appended claims.

BRIEF DESCRIPTION OF THE FIGURES

The following drawings are part of the present specification and are included to further demonstrate certain aspects of the invention. The invention may be better understood by reference to one or more of these drawings in combination with the detailed description of the specific embodiments presented herein.

DETAILED DESCRIPTION OF THE INVENTION

Figure 1:
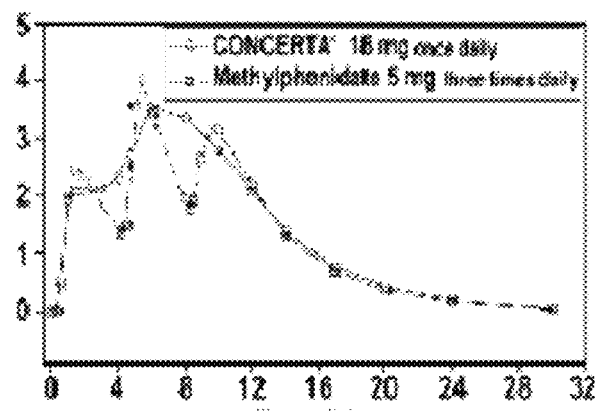
FIG. 1 depicts prior art plasma profile for CONCERTA® (18 mg dose, once daily) and a comparative rapid release tablet (5 mg dose, three times daily).

As used herein, the term methylphenidate (MPH) refers to any and all isomers thereof, meaning it includes the optically pure enantiomers, the diastereomers, the optically enriched forms, the diastereomerically enriched forms, the racemic form, S,S-form, R,R-form, S,R-form, and R,S-form. MPH can be present in its freebase form or in a salt form thereof. Pharmaceutically acceptable salt forms are contemplated, the most common being the hydrochloride salt. The amount (or dose) of MPH present in an osmotic device refers to its freebase form and/or its salt form unless otherwise specified. In some embodiments, the MPH salt has an ion in common with the osmotic salt. In some embodiments, the preferred MPH salt is a mineral acid salt, such as the hydrochloride or hydrobromide salt. MPH can be present in hydrate, hemihydrate, or anhydrous form or mixtures thereof. MPH can be present in crystalline or amorphous forms of mixtures thereof. Mixtures of all forms of MPH are contemplated within the scope of the invention.

By "environment" is meant an "environment of use", which is a locale in which a device of the invention is placed and into which the contents of the device (dosage form) are released. By "aqueous environment of use" is meant an environment of use containing an aqueous medium to which a device of the invention is exposed during use. The aqueous medium can be water, buffer, aqueous fluid, body fluid or other such medium. Exemplary aqueous environments of use include a subject, an assay fluid, or other similar environments. A subject can be human or non-human.

By "rapid release" is meant a release of an active agent to an environment over a period of 1-59 minutes or 1 minute to three hours once release has begun and release can begin within a few minutes after administration or after expiration of a delay period (lag time) after administration.

By "immediate release" is meant a release of an active agent to an environment over a period of seconds to no more than about 30 minutes once release has begun and release begins within a second to no more than about 15 minutes after administration. An immediate release dosage form is considered a more narrowly defined rapid release dosage form, so the terms may be used interchangeably herein.

By "controlled release" is meant a release of an active agent to an environment over a period of about eight hours up to about 12 hours, up to about 14 hours, up to about 16 hours, up to about 18 hours, up to about 20 hours, a day, or more than a day. The terms controlled release, sustained release and extended release are used interchangeably herein. A controlled release can also mean substantially continuous release of drug throughout the majority of the transit time of the dosage form through the gastrointestinal tract following oral administration thereof.

A controlled release can begin within a few minutes after administration or after expiration of a delay period (lag time) after administration.

A delayed but controlled release dosage form is one that provides a delayed release of a drug followed by a controlled release of the drug. By delayed release is meant any formulation technique wherein release of the active substance from the dosage form is modified to occur at a later time than that from a conventional immediate release product. In other words, the beginning of the controlled release of drug is delayed by an initial period of time. The period of delay is generally about 5 minutes to 10 hours, 30 minutes to 10 hours, 15 min to 5 hours, 15 min to 2 hours, 15 min to 1 hour, or 1 hour to 10 hours.

A zero-order release profile characterizes the release profile of a dosage form that releases a constant amount of drug per unit time. A pseudo-zero order release profile is one that approximates a zero-order release profile. A dissolution curve shows a zero or pseudo-zero order release profile if its release rate remains constant (or relatively constant within ±10% of the average value) in the interval of time $0 \leq a \leq t \leq b$. Any profile following the equation:

$$(M(t)/M_r) = k(t-a)^n, 0.9 \leq n \leq 1.1$$

has the following release rate equation:

$$(1/M)(dM/dt) = kn(t-a)^{n-1}$$

A first order release profile characterizes the release profile of a dosage form that releases a percentage of a drug charge per unit time. A pseudo-first order release profile is one that approximates a first order release profile. A dissolution curve shows a first or pseudo-first order release profile within a certain interval of time $0 \leq a \leq t \leq b$ if its release rate is a continued monotone decreasing function of time. Specifically, a dissolution curve shows a first order profile whenever its release rate is proportional to the remaining undissolved amount of drug, as determined by the following equation:

$$(M(t)/MT) = 1 - \exp(-kt).$$

A dissolution curve shows a pseudo-first order profile when the drug release rate decreases with time as described by the Fickian or anomalous Fickian diffusion controlled release equation:

$$(M(t)/M_T) = kt^n, 0.3 \leq n \leq 0.7.$$

In some embodiments, the invention excludes dosage forms that exhibit a zero order or first order release profile.

A sigmoidal release profile can be divided into three phases: a first slower release rate phase, a second faster release rate phase and a third slower release rate phase. A sigmoidal release profile characterizes the release profile of a dosage form that releases a drug in a controlled manner but very slowly during a first release period, then more rapidly during a second release period and finally very slowly during a third release period such that the release profile resembles a sigmoid. A dissolution curve shows a sigmoid release profile within a certain interval of time $0 \leq a \leq t \leq b$ if its release rate reaches a single maximum within the interval (a, b) excluding the extremes. That is equivalent to consider a point of time T* so that the release rate is an increasing function of time for $a \leq t \leq T^*$ and a decreasing function of time, as determined by the following equation:

Weibull Function $$(M(t)/M_T) = W_{inf}\{1 - \exp\{-[(t-t_i)/\beta]^\alpha\}\} \text{ Parameter ranges:}$$

$t_i$: between 0 and 3
$\beta$: between 7 and 12
$\alpha$: $1 < \alpha < 3$
Winf: between 0.5 and 1.1.

As used herein, the phrase "ascending rate of drug release" refers to a periodic release rate that is increased over the immediately-preceding periodic release rate, where the periodic intervals are the same and the ascending rate is provided for at least four hours after exposure of the dosage form to an aqueous environment. For example, when the quantity of drug released from a dosage form is measured at hourly intervals and the quantity of drug released during the fourth hour following exposure of the dosage form to an aqueous environment of use (determined at t=4 hours minus t=3 hours) is greater than the quantity of drug released from the dosage form during the third hour following exposure of the dosage form to an aqueous environment of use (determined at t=3 hours minus t=2 hours), an ascending release rate from the third hour to the fourth hour has occurred, and when the quantity of drug released during the third hour following exposure of the dosage form to an aqueous environment of use (determined at t=3 hours minus t=2 hours) is greater than the quantity of drug released from the dosage form during the second hour following exposure of the dosage form to an aqueous environment of use (determined at t=2 hours minus t=1 hours), an ascending release rate from the second hour to the third hour has occurred, and when the quantity of drug released during the second hour following exposure of the dosage form to an aqueous environment of use (determined at t=2 hours minus t=1 hours) is greater than the quantity of drug released from the dosage form during the first hour following exposure of the dosage form to an aqueous environment of use (determined at t=1 hours minus t=0 hour), an ascending release rate from the first hour to the second hour has occurred. The "ascending rate of drug release" described herein refers to the release rate from a dosage form adapted to provide controlled release of drug and does not include release of drug from any immediate-release drug coating that may be applied to the dosage form. In some embodiments, the invention includes a controlled release dosage form that does not exhibit an ascending rate of drug release from the core of the coated dosage form.

The core comprises at least one or at least two water swellable excipients which expand in size during use of the dosage form. A gel or gelatinous mass forms in the core when exposed to water. Drug may or may not be extruded from the core in the form of a gel via the preformed passageway and/or a passageway formed during use. The drug diffuses from the gel in dissolved form during use.

In vitro release profiles of MPH from the coated core of an exemplary osmotic device comprising 18 mg of MPH (distributed between the core and an exterior drug-containing coating) was characterized as follows when the in vitro release profiles were obtained according to USP <724> in the aqueous media (50 mL, as specified below) at 37±0.5° C. in an Apparatus type 7.

TABLE 1 pH 3
Dissolution (% wt)

| Time (hr) | Median or mean | Min | Max |
| --- | --- | --- | --- |
| 0 | 0 | 0 | 0 |
| 1 | 24 | 23 | 25 |
| 2 | 30 | 29 | 31 |
| 4 | 52 | 49 | 54 |
| 6 | 76 | 73 | 79 |
| 8 | 97 | 96 | 100 |
| 10 | 100 | 98 | 100 |

TABLE 2

0.1 N HCl
Dissolution (% wt)

| Time (hr) | Median or mean | Min | Max |
| --- | --- | --- | --- |
| 0 | 0 | 0 | 0 |
| 1 | 24 | 22 | 27 |
| 2 | 29 | 27 | 32 |
| 4 | 50 | 47 | 53 |
| 6 | 73 | 70 | 76 |
| 8 | 96 | 93 | 98 |
| 10 | 100 | 96 | 100 |

TABLE 3 pH 4.5 acetate buffer
Dissolution (% wt)

| Time (hr) | Median or mean | Min | Max |
| --- | --- | --- | --- |
| 0 | 0 | 0 | 0 |
| 1 | 24 | 21 | 25 |
| 2 | 30 | 27 | 31 |
| 4 | 51 | 46 | 55 |
| 6 | 75 | 68 | 83 |
| 8 | 97 | 92 | 100 |
| 10 | 100 | 95 | 100 |

TABLE 4 pH 6.8 phosphate buffer
Dissolution (% wt)

| Time (hr) | Median or mean | Min | Max |
| --- | --- | --- | --- |
| 0 | 0 | 0 | 0 |
| 1 | 23 | 21 | 25 |
| 2 | 29 | 27 | 32 |
| 4 | 50 | 48 | 53 |
| 6 | 75 | 71 | 76 |
| 8 | 96 | 93 | 100 |
| 10 | 100 | 96 | 100 |

TABLE 5

Deionized water
Dissolution (% wt)

| Time (hr) | Median or mean | Min | Max |
| --- | --- | --- | --- |
| 0 | 0 | 0 | 0 |
| 1 | 24 | 22 | 27 |
| 2 | 31 | 29 | 33 |
| 4 | 53 | 51 | 57 |
| 6 | 78 | 74 | 83 |
| 8 | 99 | 97 | 100 |
| 10 | 100 | 99 | 100 |

Based upon the above and other data, the osmotic devices provide a controlled release of MPH that is substantially (±10% or ±5% of the specified values) independent of the pH of the aqueous medium. In other words, the drug release profile changes by less than 10% when evaluated in aqueous solutions varying in pH as specified herein.

The values set forth in the above and below tables herein are approximate values. Depending upon the conditions of measurement as well as the assay used to determine those values, they may have a standard deviation of +/−2%, +/−5% or +/−10% of the indicated value.

The maximum and minimum release profiles can be thought of as approximations of the upper and lower boundaries within which the release profile of the exemplary osmotic device will vary on an overall or point to point basis. In other words, the area defined by the upper and lower boundaries is an approximation of the mean release profile plus or minus the standard deviation at the points of measurement.

Different embodiments of dosage form comprise different dosage strengths of MPH; however, the release profile is substantially independent of dosage strength. The release profile of MPH (from the core and the exterior drug-containing coating) of the dosage form can be more generally characterized as follows when determined according to USP <724> in the aqueous media (50 mL) specified below at 37±0.5° C. in an Apparatus type 7.

TABLE 6

| Time (hr) | Deionized water Dissolution (% wt) Median or mean range | Deionized water Dissolution (% wt) Median or mean range | Deionized water Dissolution (% wt) Median or mean range |
|---|---|---|---|
| 0 | 0 | 0 | 0 |
| 1 | 21-27 | 20-30 | 16-24 |
| 2 | 27-34 | 25-35 | 25-34 |
| 4 | 46-57 | 45-60 | 42-58 |
| 6 | 68-83 | 68-85 | 58-79 |
| 8 | 92-100 | 90-100 | 71-95 |
| 10 | 95-100 | 91-100 | 79-100 |

The osmotic device of the invention comprising a core surrounded by a semipermeable membrane and having an exterior MPH-containing coating can exhibit any of the following drug release (dissolution) profiles for the total amount of drug released when placed in aqueous 0.1 N HCl at 37±1° C. in the absence of EtOH.

| Time (hr) | MPH released (% wt) Median or mean range | MPH released (% wt) Median or mean range | MPH released (% wt) Median or mean range | MPH released (% wt) Median or mean range |
|---|---|---|---|---|
| 1 | 20-30 | 22-27 | 21-27 | 15-25 |
| 2 | 25-35 | 29-33 | 27-34 | 25-35 |
| 4 | 45-60 | 51-57 | 46-57 | 42-60 |
| 6 | 68-85 | 74-83 | 68-83 | 58-85 |
| 8 | 90-100 | 97-100 | 92-100 | 71-95 |
| 10 | 91-100 | 99-100 | 95-100 | 79-100 |
| 1 | 15-25 | 15-25 | | |
| 2 | 25-35 | 25-35 | | |
| 4 | 45-60 | 47-60 | | |
| 6 | 62-85 | 65-80 | | |
| 8 | 80-95 | 80-95 | | |
| 10 | 85-100 | 88-100 | | |

The dosage form of the invention can provide an overall release profile wherein about 65% to about 85% wt of the drug is released in a controlled or continuous manner throughout a period of about 6 h after placement in an environment of use or after oral administration. The release can be such that about 25% to about 35% wt of the drug is released by about 2 hours, about 45% to about 60% wt of the drug is released by about 4 hours, about 65% to about 85% of the drug is released by about 6 hours, about 85% to about 100% wt of the drug is released by about 8 hours and no less than 85% of the drug is released by about 10 hours after placement of the osmotic device (comprising a core, semipermeable membrane and exterior drug-containing coating) in an environment of use or after oral administration.

The dosage form of the invention can provide a release profile wherein about 55% to about 80% wt of the drug is released in a controlled or continuous manner throughout a period of about 6 h after placement of the osmotic device (comprising a core, semipermeable membrane and exterior drug-containing coating) in an environment of use or after oral administration. The release can be such that about 25% to about 35% wt of the drug is released by about 2 hours, about 42% to about 60% wt of the drug is released by about 4 hours, about 55% to about 80% of the drug is released by about 6 hours, about 70% to about 100% wt of the drug is released by about 8 hours and no less than 80% of the drug is released by about 10 hours after placement in an environment of use or after oral administration.

The release can be such that about 50 to about 100% wt of the drug is released by about six hours, about 65 to about 100% of the drug is released by about 8 hours, and no less than 70% of the drug is released by about 12 hours after placement of the osmotic device (comprising a core, semipermeable membrane and exterior drug-containing coating) in an environment of use or after oral administration.

In some embodiments, the release profile of drug from the membrane coated core is first order, pseudo-first order, zero order or pseudo-zero order. Drug is released in a continuous or controlled manner. In some embodiments, the dosage form of the invention excludes a gastroretentive dosage form.

Figure 2A:
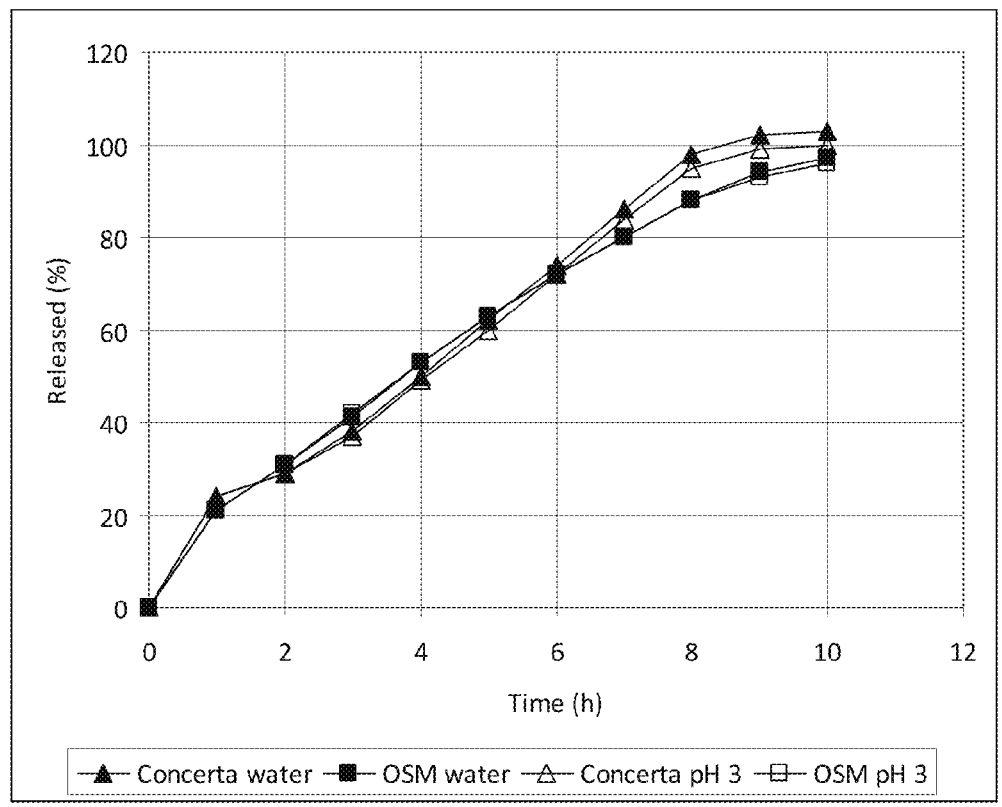
FIG. 2A depicts the comparative overall in vitro drug release profiles for CONCERTA® osmotic device (54 mg dose) in deionized water (filled triangle) and water at pH 3 (open triangle) and the dosage form of the invention (54 mg dose) in deionized water (filled square) and water at pH 3 (open square).

The dosage form will generally provide release of MPH from the membrane coated core according to a zero order, pseudo-zero order, first order or pseudo-first order in vitro release profile. This release profile is different than the release profile provided by CONCERTA® osmotic devices. FIG. 2A depicts the in vitro release profiles for CONCERTA® osmotic device (diamonds, 54 mg dosage strength) and the osmotic device of the invention (squares) in deionized water (filled indicators) and in water with pH adjusted to 3 (open indicators). CONCERTA® osmotic devices provide a sigmoidal release of drug, whereby the rate of drug release accelerates (increases) throughout the period of 1-6 hours or 1-8 hours after placement in the water. In other words, the CONCERTA® osmotic devices provide an ascending rate of drug release over an extended period of at least 5-6 h. On the other hand, the instant osmotic device does not exhibit an increasing (ascending) rate of drug release and instead provides a steady (zero order or pseudo-zero order) or decreasing (descending, first order or pseudo-first order) rate of drug release throughout the period of 1-6 hours or 1-8 hours after placement in the water. Both devices comprise MPH in the core and in an exterior drug-containing coating.

Figure 2B:
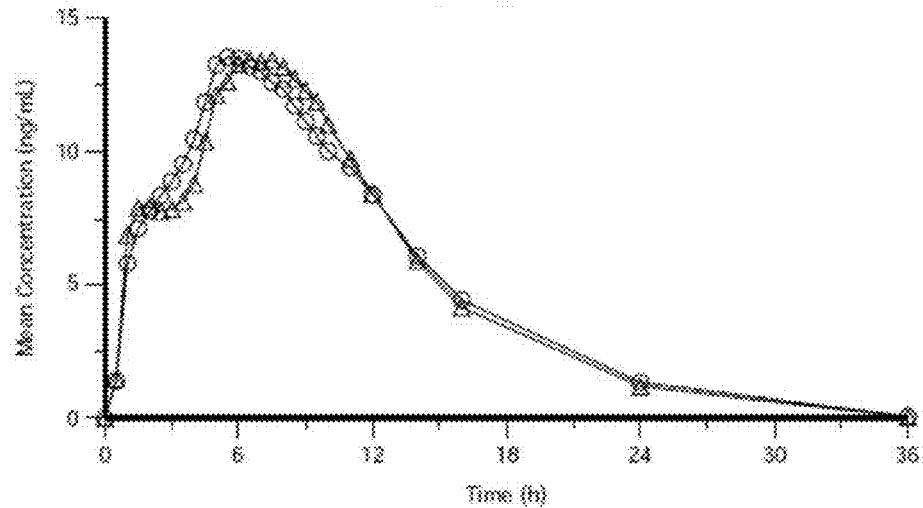
FIGS. 2B and 2C depict the comparative exemplary plasma profiles for CONCERTA® osmotic device (open triangles, 54 mg dose) and the dosage form of the invention (open circles, 54 mg dose) following administration of a single dose of each to healthy subjects under fasted (FIG. 2B) and fed (FIG. 2C) conditions.
Figure 2C:
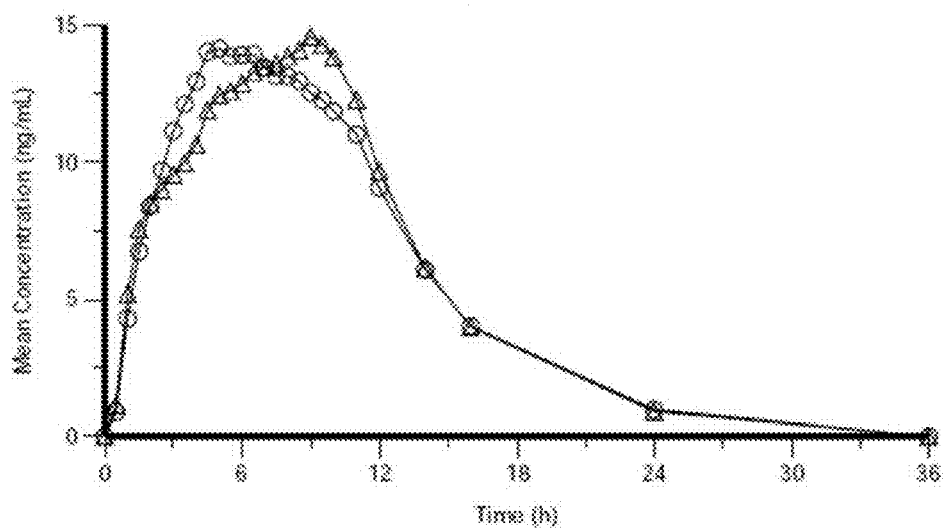

The osmotic device provides an improved pharmacokinetic profile when orally administered to a subject as compared to CONCERTA® osmotic devices. FIGS. 2B and 2C depict the comparative exemplary plasma profiles for CONCERTA® (open triangles, 54 mg dose) and the dosage form of the invention (open circles, 54 mg dose) following administration of a single dose of each to healthy subjects under fasted (FIG. 2B) and fed (FIG. 2C) conditions. The observed pharmacokinetic parameters are summarized as follows. The data was obtained during the clinical trial described in Example 8. Both osmotic devices comprise a core, semipermeable membrane and exterior drug-containing coating.

TABLE 7

| Parameter | Fed (FIG. 2C) | | | | Fasted (FIG. 2B) | | | |
| --- | --- | --- | --- | --- | --- | --- | --- | --- |
| | OSM | | CONCERTA ® | | OSM | | CONCERTA ® | |
| | Mean | SD | mean | SD | mean | SD | mean | SD |
| Tmax (h) | 5.69 | 2.30 | 7.96 | 2.08 | 5.95 | 0.99 | 6.95 | 1.28 |
| Cmax (ng/mL) | 16.3 | 4.78 | 16.5 | 4.59 | 14.5 | 5.55 | 14.6 | 6.01 |
| $AUC_{inf}$ (h * ng/mL) | 182.3 | 53.66 | 182.5 | 54.62 | 176.6 | 82.39 | 173.8 | 78.34 |

Even though the package insert for the CONCERTA® osmotic device indicates "CONCERTA® should be administered orally once daily in the morning with or without food", and "In patients, there were no differences in either the pharmacokinetics or the pharmacodynamic performance of CONCERTA® when administered after a high-fat breakfast", the above data suggests food undesirably increases the Tmax for the CONCERTA® osmotic device; however, food surprisingly has very little impact upon the Tmax for the instant osmotic device. This surprising advantage allows for the administration of the instant osmotic device regardless of ingestion of food and thus provides a substantial clinical and therapeutic benefit over the CONCERTA® osmotic device.

Figure 2D:
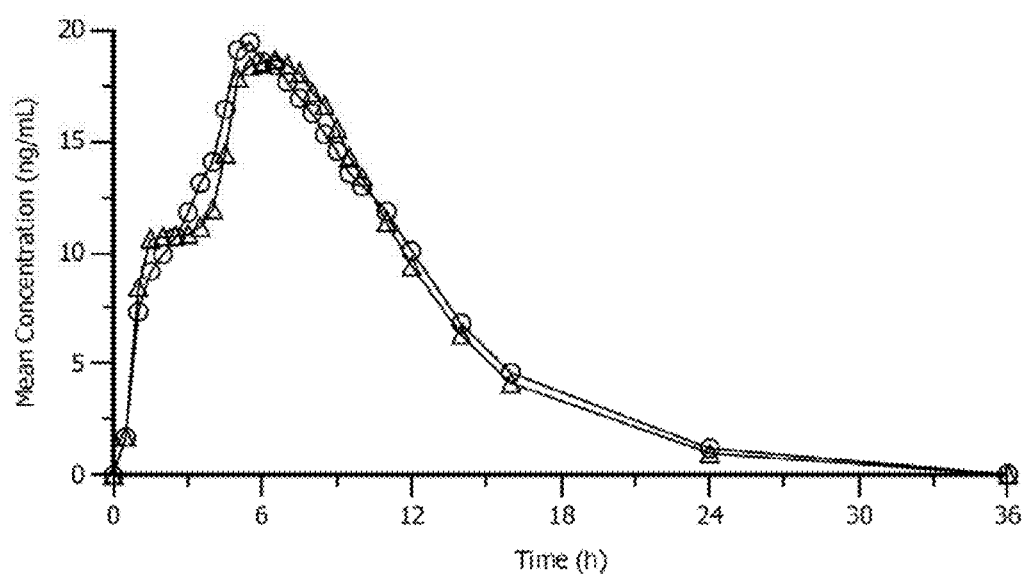
FIG. 2D depicts the comparative exemplary plasma profiles for CONCERTA® osmotic device (open triangles, 2×36 mg dose) and the dosage form of the invention (open circles, 72 mg dose) following administration of a single dose of each to healthy subjects under fasted conditions.

FIG. 2D depicts the comparative exemplary plasma profiles for CONCERTA® (open triangles, 2×36 mg dose) and the dosage form of the invention (open circles, 72 mg dose) following administration of a single dose of each to healthy subjects under fasted conditions. The observed pharmacokinetic parameters are summarized as follows. The data was obtained during the clinical trial described in Example 9. Both osmotic devices comprise a core, semipermeable membrane and exterior drug-containing coating.

TABLE 8

| | Fasted (FIG. 2D) | | | |
| --- | --- | --- | --- | --- |
| | OSM | | CONCERTA | |
| Parameter | mean | SD | mean | SD |
| Tmax (h) | 5.68 | 0.96 | 6.25 | 1.33 |
| Cmax (ng/mL) | 20.6 | 6.24 | 20.3 | 7.41 |
| $AUC_{inf}$ (h * ng/mL) | 218.1 | 83.78 | 210.9 | 84.11 |

In some embodiments, the instant osmotic device is approximately bioequivalent to the CONCERTA® osmotic device in terms of Cmax and/or AUCinf.

The instant osmotic devices provide substantially improved resistance towards alcohol-related dose-dumping as compared to the CONCERTA® osmotic devices. Alcohol-related dose-dumping was evaluated according to Example 7 and the corresponding results are detailed in FIGS. 3-8. The comparisons were conducted on an equivalent dose basis and under similar test conditions. The CONCERTA® and instant osmotic devices included the same total dose of MPH divided among their respective IR (drug-containing coating) and ER (coated core) components.

The osmotic devices (CONCERTA® and instant) were placed in aqueous 0.1 N HCl at 37±1° C. or aqueous ethanol (40% ethanol in aqueous 0.1 N HCl at 37±1° C.) and their in vitro MPH release profiles were observed for a period of 2 h (120 min). A 2 h time limit was imposed, because the in vivo adsorption of ethanol occurs very rapidly and in the stomach such that there is a very limited time window (about 2 h) in vivo within which ethanol might impact the release of MPH from an osmotic device. The influence of ethanol upon release of from the osmotic devices was determined by comparing the 2-h drug release profiles in the absence and presence of ethanol.

Relative increase in the total percentage of drug released at the 120 min time point was calculated as follows: (% $Rel_{alcohol}$/% $Rel_{water}$) Also, the average rate of drug release during the time period of 15 min to 120 min was calculated in order to eliminate the impact of the IR component upon drug the calculations, thereby focusing solely on drug release from the ER component. The average rate of drug release (expressed as percentage released per min during the time period of t=15-120 min) is the slope of the respective lines depicted in FIG. 3: Line A represents the average rate of release for CONCERTA® osmotic device in water; Line B represents the average rate of release for CONCERTA® osmotic device in 40% ethanol in aqueous 0.1 N HCl at 37±1° C.; Line C represents the average rate of release for the instant osmotic device in water; Line D represents the average rate of release for the instant osmotic device in 40% ethanol in aqueous 0.1 N HCl at 37±1° C. The average rate of drug release per min ($RRel_{avg}$, slope of lines A-D) was calculated as follows: $RRel_{avg}$=(% $Rel_{t=120}$-% $Rel_{t=15}$)/105 min. The relative increase in the average rate of drug release due to the alcohol related dose-dumping was calculated as follows: $RRel_{avg(alcohol)}$/$RRel_{avg(water)}$.

Figure 3:
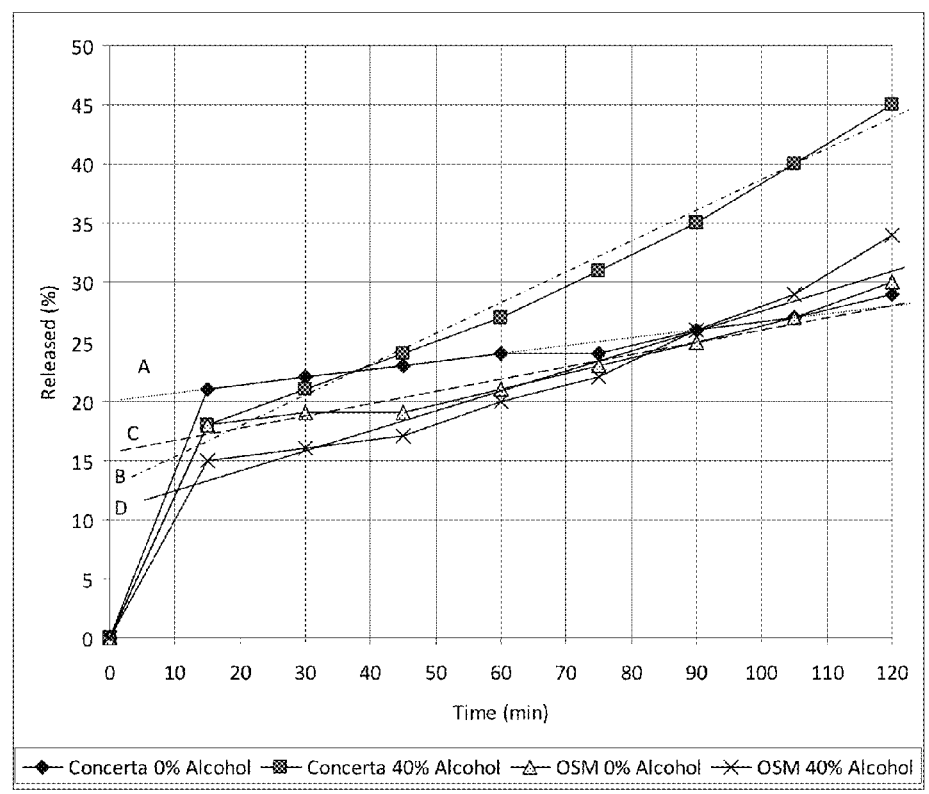
FIG. 3 depicts exemplary in vitro drug release profiles for CONCERTA® osmotic device (18 mg dose) in the absence (filled diamond) and presence of ethanol (filled square, 40% ethanol in aqueous 0.1 N HCl at 37±1° C.) and for the osmotic device (15007) of the invention (18 mg dose) in the absence (open triangle) and presence of ethanol (X, 40% ethanol in aqueous 0.1 N HCl at 37±1° C.). Both osmotic device comprise MPH in a drug-containing exterior coating and in the core.

FIG. 3 depicts exemplary in vitro drug release profiles for CONCERTA® osmotic device (18 mg dose) in the absence (filled diamond) and presence of ethanol (filled square, 40% ethanol in aqueous 0.1 N HCl at 37±1° C.) and for an osmotic device (15007) of the invention (18 mg dose) in the absence (open triangle) and presence of ethanol (X, 40% ethanol in aqueous 0.1 N HCl at 37±1° C.). The following table summarizes the results. Both osmotic devices comprise a core, semipermeable membrane and exterior drug-containing coating.

TABLE 9

| Test Parameter | CONCERTA ® (18 mg) | OSM (18 mg) |
| --- | --- | --- |
| Total release (% @ 2 h in aqueous 0.1N HCl at 37 ± 1° C.) | 29 | 30 |
| Total release (% @ 2 h in 40% EtOH in aqueous 0.1N HCl at 37 ± 1° C.) | 46 | 34 |
| Relative increase in release (= EtOH value/H$_2$O value) | 1.59 | 1.13 |
| Average release rate (t = 15-120 min, in aqueous 0.1N HCl at 37 ± 1° C.) (%/min) | 0.076 | 0.114 |

TABLE 9-continued

| Test Parameter | CONCERTA ® (18 mg) | OSM (18 mg) |
|---|---|---|
| Average release rate (t = 15-120 min, in 40% ethanol in aqueous 0.1N HCl at 37 ± 1° C.) (%/min) | 0.257 | 0.181 |
| Relative increase in average release rate (= EtOH value/H₂O value) | 3.38 | 1.59 |

The instant osmotic device provides a less than 1.6-fold ethanol-related increase in the average rate of MPH release during the time period of 15 min to 120 min, when comparing the release rates in aqueous 0.1 N HCl at 37±1° C. and in 40% ethanol in aqueous 0.1 N HCl at 37±1° C. In comparison, the CONCERTA® osmotic device provides an almost 3.4-fold ethanol-related increase in the average rate of MPH release during the time period of 15 min to 120 min, when comparing the release rates in aqueous 0.1 N HCl at 37±1° C. and in 40% ethanol in aqueous 0.1 N HCl at 37±1° C. The instant osmotic device provides a less than 1.2-fold ethanol-related increase in the total amount of MPH released during the first 120 min, when comparing the release rates in aqueous 0.1 N HCl at 37±1° C. and in 40% ethanol in aqueous 0.1 N HCl at 37±1° C. In comparison, the CONCERTA® osmotic device provides an almost 1.6-fold ethanol-related increase in the total amount of MPH released during the first 120 min, when comparing the release rates in aqueous 0.1 N HCl at 37±1° C. and in 40% ethanol in aqueous 0.1 N HCl at 37±1° C.

Figure 4:
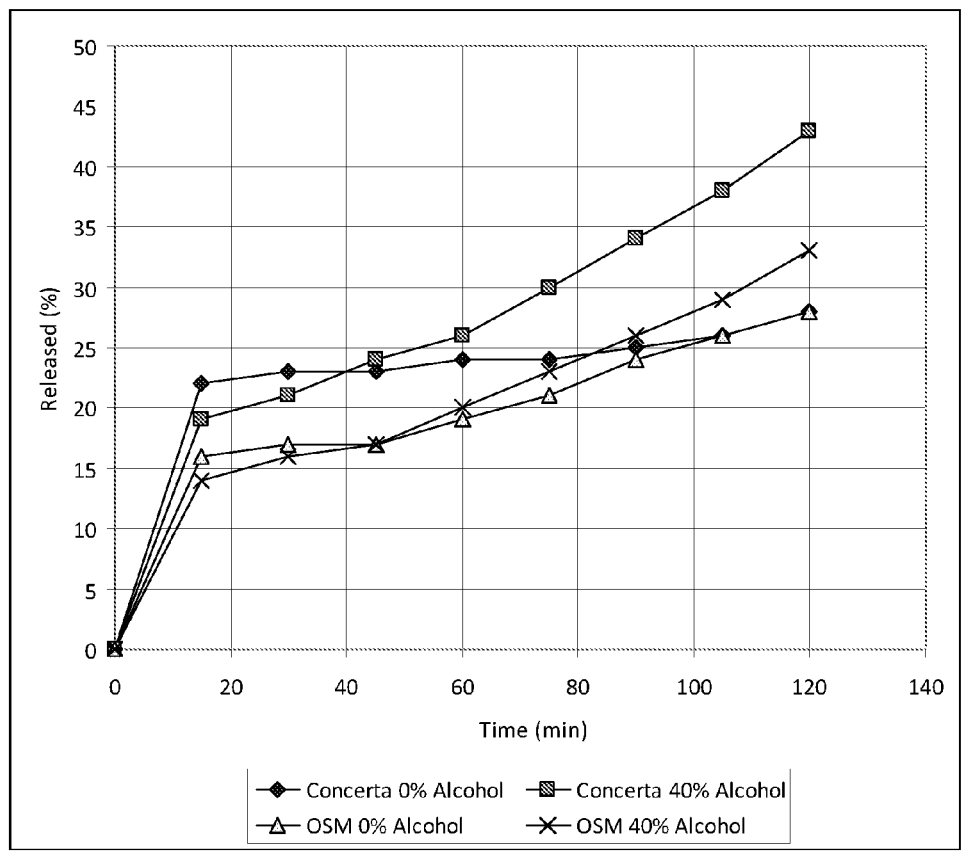
FIG. 4 depicts exemplary in vitro drug release profiles for CONCERTA® osmotic device (27 mg dose) in the absence (filled diamond) and presence of ethanol (filled square, 40% ethanol in aqueous 0.1 N HCl at 37±1° C.) and for the osmotic device (15008) of the invention (27 mg dose) in the absence (open triangle) and presence of ethanol (X, 40% ethanol in aqueous 0.1 N HCl at 37±1° C.). Both osmotic device comprise MPH in a drug-containing exterior coating and in the core.

FIG. 4 depicts exemplary in vitro drug release profiles for CONCERTA® osmotic device (27 mg dose) in the absence (filled diamond) and presence of ethanol (filled square, 40% ethanol in aqueous 0.1 N HCl at 37±1° C.) and for the osmotic device (15008) of the invention (27 mg dose) in the absence (open triangle) and presence of ethanol (X, 40% ethanol in aqueous 0.1 N HCl at 37±1° C.). The following table summarizes the results. Both osmotic devices comprise a core, semipermeable membrane and exterior drug-containing coating.

TABLE 10

| Test Parameter | CONCERTA ® (27 mg) | OSM (27 mg) |
|---|---|---|
| Total release (% @ 2 h in aqueous 0.1N HCl at 37 ± 1° C.) | 28 | 28 |
| Total release (% @ 2 h in 40% ethanol in aqueous 0.1N HCl at 37 ± 1° C.) | 43 | 33 |
| Relative increase in release (= EtOH value/H₂O value) | 1.54 | 1.18 |
| Average release rate (t = 15-120 min, in aqueous 0.1N HCl at 37 ± 1° C.) (%/min) | 0.057 | 0.114 |
| Average release rate (t = 15-120 min, in 40% ethanol in aqueous 0.1N HCl at 37 ± 1° C.) (%/min) | 0.229 | 0.181 |
| Relative increase in average release rate (= EtOH value/H₂O value) | 4.02 | 1.59 |

The instant osmotic device provides a less than 1.6-fold ethanol-related increase in the average rate of MPH release during the time period of 15 min to 120 min, when comparing the release rates in aqueous 0.1 N HCl at 37±1° C. and in 40% ethanol in aqueous 0.1 N HCl at 37±1° C. In comparison, the CONCERTA® osmotic device provides a 4-fold ethanol-related increase in the average rate of MPH release during the time period of 15 min to 120 min, when comparing the release rates in aqueous 0.1 N HCl at 37±1° C. and in 40% ethanol in aqueous 0.1 N HCl at 37±1° C. The instant osmotic device provides a less than 1.2-fold ethanol-related increase in the total amount of MPH released during the first 120 min, when comparing the release rates in aqueous 0.1 N HCl at 37±1° C. and in 40% ethanol in aqueous 0.1 N HCl at 37±1° C. In comparison, the CONCERTA® osmotic device provides an over 1.5-fold ethanol-related increase in the total amount of MPH released during the first 120 min, when comparing the release rates in aqueous 0.1 N HCl at 37±1° C. and in 40% ethanol in aqueous 0.1 N HCl at 37±1° C.

Figure 5:
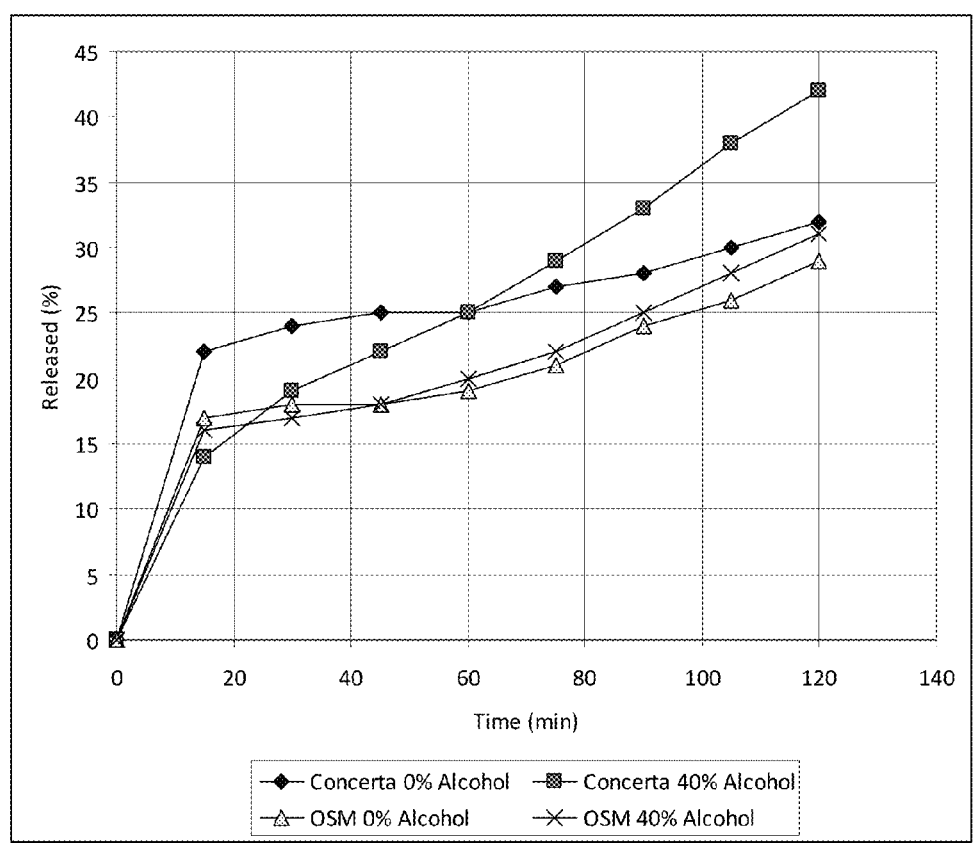
FIG. 5 depicts exemplary in vitro drug release profiles for CONCERTA® osmotic device (36 mg dose) in the absence (filled diamond) and presence of ethanol (filled square, 40% ethanol in aqueous 0.1 N HCl at 37±1° C.) and for the osmotic device (15009) of the invention (36 mg dose) in the absence (open triangle) and presence of ethanol (X, 40% ethanol in aqueous 0.1 N HCl at 37±1° C.). Both osmotic device comprise MPH in a drug-containing exterior coating and in the core.

FIG. 5 depicts exemplary in vitro drug release profiles for CONCERTA® osmotic device (36 mg dose) in the absence (filled diamond) and presence of ethanol (filled square, 40% ethanol in aqueous 0.1 N HCl at 37±1° C.) and for the osmotic device (15009) of the invention (36 mg dose) in the absence (open triangle) and presence of ethanol (X, 40% ethanol in aqueous 0.1 N HCl at 37±1° C.). The following table summarizes the results. Both osmotic devices comprise a core, semipermeable membrane and exterior drug-containing coating.

TABLE 11

| Test Parameter | CONCERTA ® (36 mg) | OSM (36 mg) |
|---|---|---|
| Total release (% @ 2 h in aqueous 0.1N HCl at 37 ± 1° C.) | 32 | 29 |
| Total release (% @ 2 h in 40% ethanol in aqueous 0.1N HCl at 37 ± 1° C.) | 42 | 31 |
| Relative increase in release (= EtOH value/H₂O value) | 1.31 | 1.07 |
| Average release rate (t = 15-120 min, in aqueous 0.1N HCl at 37 ± 1° C.) (%/min) | 0.095 | 0.114 |
| Average release rate (t = 15-120 min, in 40% ethanol in aqueous 0.1N HCl at 37 ± 1° C.) (%/min) | 0.267 | 0.143 |
| Relative increase in average release rate (= EtOH value/H₂O value) | 2.81 | 1.25 |

The instant osmotic device provides a less than 1.3-fold ethanol-related increase in the average rate of MPH release during the time period of 15 min to 120 min, when comparing the release rates in aqueous 0.1 N HCl at 37±1° C. and in 40% ethanol in aqueous 0.1 N HCl at 37±1° C. In comparison, the CONCERTA® osmotic device provides a 2.8-fold ethanol-related increase in the average rate of MPH release during the time period of 15 min to 120 min, when comparing the release rates in aqueous 0.1 N HCl at 37±1° C. and in 40% ethanol in aqueous 0.1 N HCl at 37±1° C. The instant osmotic device provides a less than 1.1-fold ethanol-related increase in the total amount of MPH released during the first 120 min, when comparing the release rates in aqueous 0.1 N HCl at 37±1° C. and in 40% ethanol in aqueous 0.1 N HCl at 37±1° C. In comparison, the CONCERTA® osmotic device provides an over 1.3-fold ethanol-related increase in the total amount of MPH released during the first 120 min, when comparing the release rates in aqueous 0.1 N HCl at 37±1° C. and in 40% ethanol in aqueous 0.1 N HCl at 37±1° C.

Figure 6:
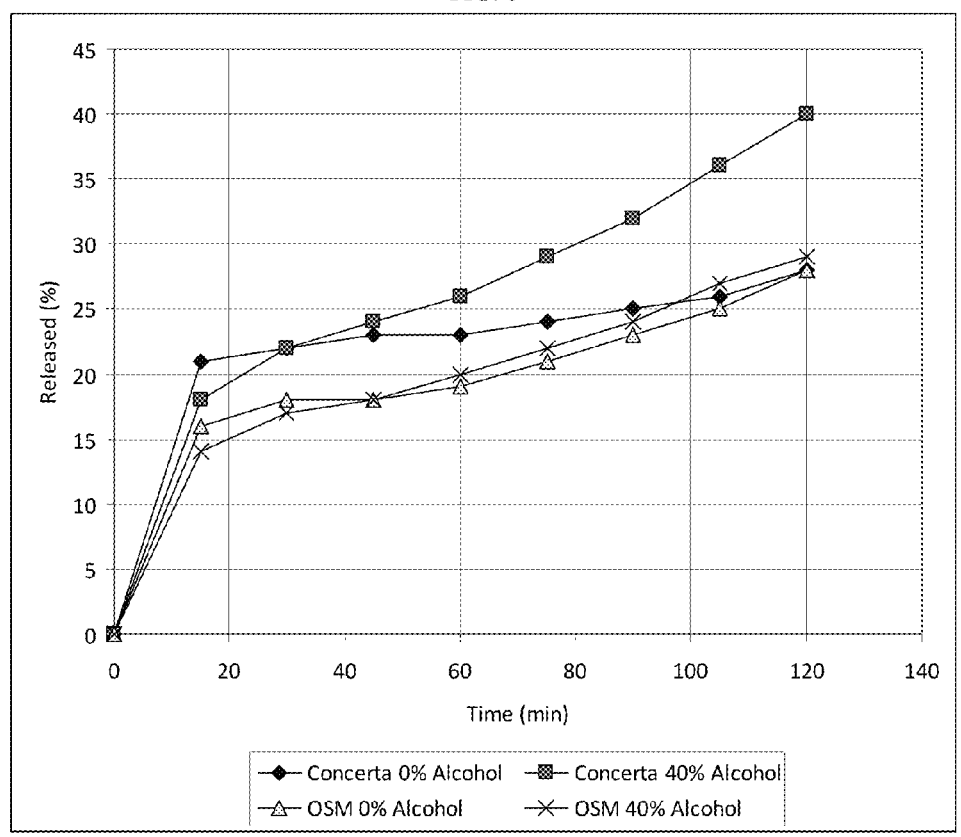
FIG. 6 depicts exemplary in vitro drug release profiles for CONCERTA® osmotic device (54 mg dose) in the absence (filled diamond) and presence of ethanol (filled square, 40% ethanol in aqueous 0.1 N HCl at 37±1° C.) and for the osmotic device (15005) of the invention (54 mg dose) in the absence (open triangle) and presence of ethanol (X, 40% ethanol in aqueous 0.1 N HCl at 37±1° C.). Both osmotic device comprise MPH in a drug-containing exterior coating and in the core.

FIG. 6 depicts exemplary in vitro drug release profiles for CONCERTA® osmotic device (54 mg dose) in the absence (filled diamond) and presence of ethanol (filled square, 40% ethanol in aqueous 0.1 N HCl at 37±1° C.) and for the osmotic device (15005) of the invention (54 mg dose) in the absence (open triangle) and presence of ethanol (X, 40% ethanol in aqueous 0.1 N HCl at 37±1° C.). The following table summarizes the results. Both osmotic devices comprise a core, semipermeable membrane and exterior drug-containing coating.

TABLE 12

| Test Parameter | CONCERTA ® (54 mg) | OSM (54 mg) |
|---|---|---|
| Total release (% @ 2 h in aqueous 0.1N HCl at 37 ± 1° C.) | 28 | 28 |
| Total release (% @ 2 h in 40% ethanol in aqueous 0.1N HCl at 37 ± 1° C.) | 40 | 29 |
| Relative increase in release (= EtOH value/H₂O value) | 1.43 | 1.04 |
| Average release rate (t = 15-120 min, in aqueous 0.1N HCl at 37 ± 1° C.) (%/min) | 0.067 | 0.114 |
| Average release rate (t = 15-120 min, in 40% ethanol in aqueous 0.1N HCl at 37 ± 1° C.) (%/min) | 0.21 | 0.143 |
| Relative increase in average release rate (= EtOH value/H₂O value) | 3.13 | 1.25 |

The instant osmotic device provides a less than 1.3-fold ethanol-related increase in the average rate of MPH release during the time period of 15 min to 120 min, when comparing the release rates in aqueous 0.1 N HCl at 37±1° C. and in 40% ethanol in aqueous 0.1 N HCl at 37±1° C. In comparison, the CONCERTA® osmotic device provides an over 3.1-fold ethanol-related increase in the average rate of MPH release during the time period of 15 min to 120 min, when comparing the release rates in aqueous 0.1 N HCl at 37±1° C. and in 40% ethanol in aqueous 0.1 N HCl at 37±1° C. The instant osmotic device provides a less than 1.1-fold ethanol-related increase in the total amount of MPH released during the first 120 min, when comparing the release rates in aqueous 0.1 N HCl at 37±1° C. and in 40% ethanol in aqueous 0.1 N HCl at 37±1° C. In comparison, the CONCERTA® osmotic device provides an over 1.4-fold ethanol-related increase in the total amount of MPH released during the first 120 min, when comparing the release rates in aqueous 0.1 N HCl at 37±1° C. and in 40% ethanol in aqueous 0.1 N HCl at 37±1° C.

Figure 7:
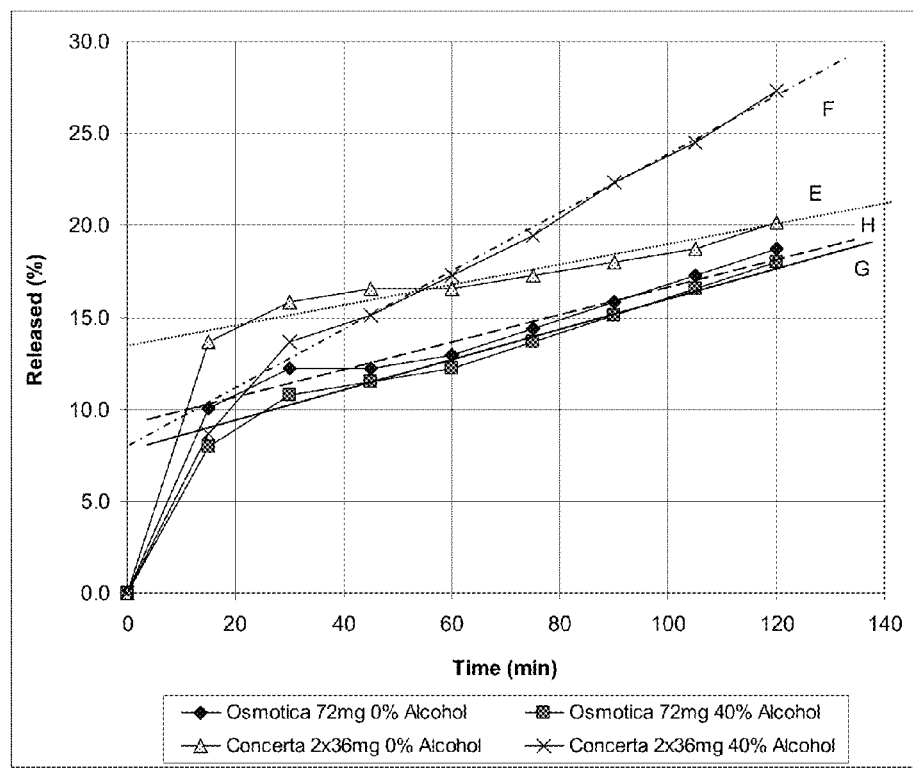
FIG. 7 depicts exemplary in vitro drug release profiles for CONCERTA® osmotic devices (2 osmotic device of 36 mg dose each) in the absence (open triangle) and presence of ethanol (X, 40% ethanol in aqueous 0.1 N HCl at 37±1° C.) and for the osmotic device (15010) of the invention (72 mg dose) in the absence (filled diamond) and presence of ethanol (filled square, 40% ethanol in aqueous 0.1 N HCl at 37±1° C.). Both osmotic device comprise MPH in a drug-containing exterior coating and in the core.

CONCERTA® osmotic devices are not available in 72 mg dose, so two 36 mg osmotic devices are used in place of one 72 mg device. FIG. 7 depicts exemplary in vitro drug release profiles for CONCERTA® osmotic devices (2 osmotic devices of 36 mg dose each) in the absence (open triangle) and presence of ethanol (X, 40% ethanol in aqueous 0.1 N HCl at 37±1° C.) and for the osmotic device (15010) of the invention (72 mg dose) in the absence (filled diamond) and presence of ethanol (filled square, 40% ethanol in aqueous 0.1 N HCl at 37±1° C.). The following table summarizes the results. Both osmotic devices comprise a core, semipermeable membrane and exterior drug-containing coating.

TABLE 13

| Test Parameter | CONCERTA ® (2× 36 mg) | OSM (72 mg) |
|---|---|---|
| Total release (% @ 2 h in aqueous 0.1N HCl at 37 ± 1° C.) | 32 | 26 |
| Total release (% @ 2 h in 40% ethanol in aqueous 0.1N HCl at 37 ± 1° C.) | 42 | 25 |
| Relative increase in release (= EtOH value/H₂O value) | 1.31 | 0.96 |
| Average release rate (t = 15-120 min, in aqueous 0.1N HCl at 37 ± 1° C.) (%/min) | 0.095 | 0.114 |

TABLE 13-continued

| Test Parameter | CONCERTA ® (2× 36 mg) | OSM (72 mg) |
|---|---|---|
| Average release rate (t = 15-120 min, in 40% ethanol in aqueous 0.1N HCl at 37 ± 1° C.) (%/min) | 0.267 | 0.133 |
| Relative increase in average release rate (= EtOH value/H₂O value) | 2.81 | 1.17 |

The instant osmotic device provides a less than 1.2-fold ethanol-related increase in the average rate of MPH release during the time period of 15 min to 120 min, when comparing the release rates in aqueous 0.1 N HCl at 37±1° C. and in 40% ethanol in aqueous 0.1 N HCl at 37±1° C. In comparison, the CONCERTA® osmotic device provides a 2.8-fold ethanol-related increase in the average rate of MPH release during the time period of 15 min to 120 min, when comparing the release rates in aqueous 0.1 N HCl at 37±1° C. and in 40% ethanol in aqueous 0.1 N HCl at 37±1° C. The instant osmotic device provides no increase in the total amount of MPH released during the first 120 min, when comparing the release rates in aqueous 0.1 N HCl at 37±1° C. and in 40% ethanol in aqueous 0.1 N HCl at 37±1° C. In comparison, the CONCERTA® osmotic device provides an over 1.3-fold ethanol-related increase in the total amount of MPH released during the first 120 min, when comparing the release rates in aqueous 0.1 N HCl at 37±1° C. and in 40% ethanol in aqueous 0.1 N HCl at 37±1° C.

Figure 8:
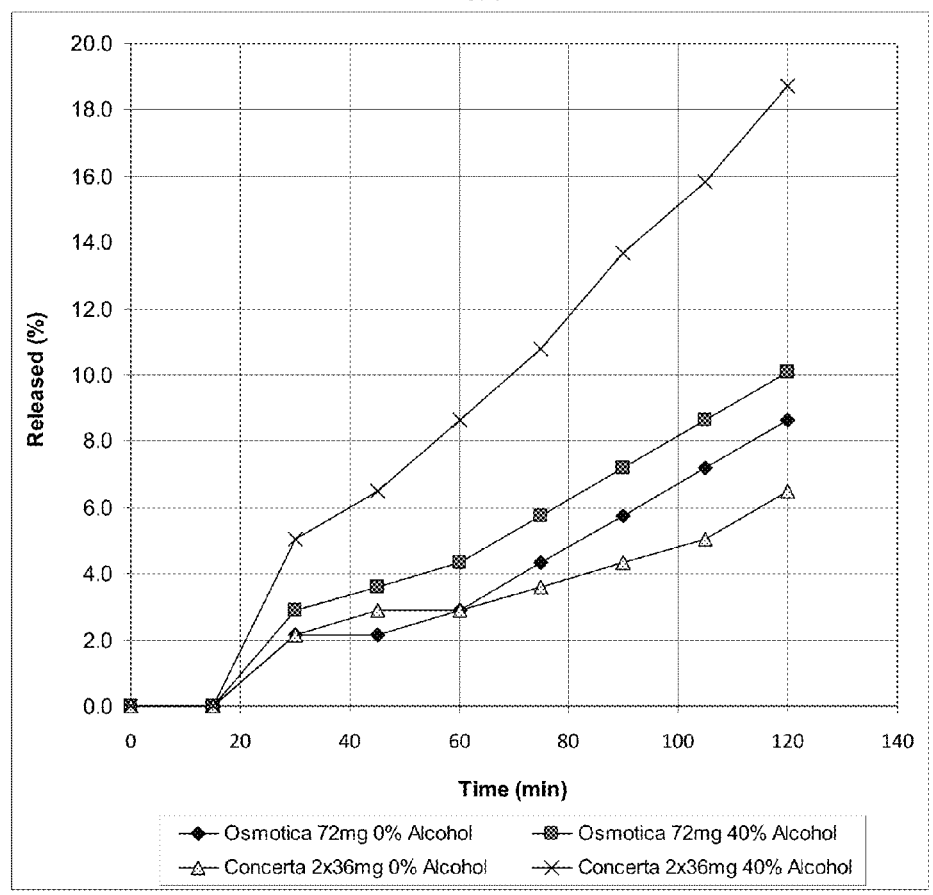
FIG. 8 depicts exemplary in vitro drug release profiles for CONCERTA® osmotic devices (2 osmotic devices of 36 mg dose each) in the absence (open triangle) and presence of ethanol (X, 40% ethanol in aqueous 0.1 N HCl at 37±1° C.) and for the osmotic device of the invention (72 mg dose) in the absence (filled diamond) and presence of ethanol (filled square, 40% ethanol in aqueous 0.1 N HCl at 37±1° C.). The release profiles have been normalized by removal of the immediate release drug data points to exhibit the release of drug only from the core.

In order to more clearly evaluate the release of drug from the core rather than the release of drug from the core and an IR coating, the release profiles of FIG. 7 were normalized by removal of the immediate release drug data points to exhibit the release of drug only from the core. FIG. 8 depicts the normalized exemplary in vitro drug release profiles for CONCERTA® osmotic devices (2 osmotic devices of 36 mg dose each) in the absence (open triangle) and presence of ethanol (X, 40% ethanol in aqueous 0.1 N HCl at 37±1° C.) and for the osmotic device of the invention (72 mg dose) in the absence (filled diamond) and presence of ethanol (filled square, 40% ethanol in aqueous 0.1 N HCl at 37±1° C.). The following table summarizes the results, wherein the percentages of drug released are based upon the amount of drug in the core rather than the amount of drug in the total Table 14

TABLE 14

| Test Parameter | CONCERTA ® (2× 36 mg) | OSM (72 mg) |
|---|---|---|
| Total release (% for t = 15-120 min in aqueous 0.1N HCl at 37 ± 1° C.) | 6.5 | 8.6 |
| Total release (% for t = 15-120 min in 40% ethanol in aqueous 0.1N HCl at 37 ± 1° C.) | 18.7 | 10.1 |
| Relative increase in release (= EtOH value/H₂O value) | 2.88 | 1.17 |
| Average release rate (t = 15-120 min, in aqueous 0.1N HCl at 37 ± 1° C.) (%/min) | 0.062 | 0.082 |
| Average release rate (t = 15-120 min, in 40% ethanol in aqueous 0.1N HCl at 37 ± 1° C.) (%/min) | 0.178 | 0.096 |
| Relative increase in average release rate (= EtOH value/H₂O value) | 2.88 | 1.17 |

In each case and at each dosage strength, the instant osmotic device unexpectedly provides a greatly improved performance over the CONCERTA® osmotic device by significantly reducing the level of ethanol-related dose-dumping. The instant osmotic device provides a less than 2-fold, less than 1.8-fold, less than 1.7-fold, less than 1.6-fold, less than 1.5-fold, less than 1.4-fold, or less than 1.3-fold ethanol-related increase in the average rate of MPH release during the time period of 15 min to 120 min, when comparing the release rates in aqueous 0.1 N HCl at 37±1° C. and in 40% ethanol in aqueous 0.1 N HCl at 37±1° C. The instant osmotic device provides a less than 1.5-fold, less than 1.4-fold, less than 1.3-fold, less than 1.2-fold, less than 1.15-fold, less than 1.1-fold or less than 1.05-fold ethanol-related increase or provides no increase in the total amount of MPH released during the first 120 min, when comparing the release rates in aqueous 0.1 N HCl at 37±1° C. and in 40% ethanol in aqueous 0.1 N HCl at 37±1° C.

The osmotic device of the invention provides reduced release of MPH from the core as compared to the CONCERTA® osmotic device having the same amount of MPH when comparing ethanol-related (ethanol-induced) dose dumping. The osmotic device of the invention comprising a core surrounded (enclosed) by a semipermeable membrane and having an exterior MPH-containing coating can exhibit any of the following drug release (dissolution) profiles when placed in aqueous 0.1 N HCl at 37±1° C. in the presence of EtOH (40%).

| Time (min) | MPH released (% wt) Median or mean range | MPH released (% wt) Median or mean range | MPH released (% wt) Median or mean range | MPH released (% wt) Median or mean range |
|---|---|---|---|---|
| 15 | 11-19 | 11-19 | 12-20 | 10-19 |
| 30 | 12-20 | 12-21 | 13-21 | 12-22 |
| 45 | 13-21 | 13-22 | 13-22 | 13-23 |
| 60 | 15-25 | 15-25 | 15-25 | 15-25 |
| 75 | 19-26 | 18-28 | 17-27 | 17-27 |
| 90 | 21-30 | 22-30 | 20-30 | 19-29 |
| 105 | 24-34 | 24-34 | 23-33 | 22-32 |
| 120 | 29-39 | 28-38 | 26-37 | 24-34 |
| 15 | 4-12 | 4-20 | 11-20 | |
| 30 | 7-15 | 7-22 | 12-22 | |
| 45 | 8-16 | 8-23 | 13-23 | |
| 60 | 9-17 | 9-25 | 15-25 | |
| 75 | 10-18 | 10-28 | 18-28 | |
| 90 | 12-19 | 12-30 | 19-30 | |
| 105 | 13-21 | 13-34 | 22-34 | |
| 120 | 15-22 | 15-39 | 24-39 | |

The CONCERTA® osmotic device comprises a tri-layered core (as described in product package insert; FDA Application No. N021121— dosage strengths 18 mg, 36 mg, 54 mg, 27 mg; and U.S. Pat. No. 6,919,373, U.S. Pat. No. 6,930,129, U.S. Pat. No. 8,163,798, U.S. Pat. No. 8,629,179, U.S. Pat. No. 9,000,038, U.S. Pat. No. 9,029,416, and U.S. Pat. No. 9,144,549); however, the instant osmotic device comprises a bi-layered core. Experiments were conducted to determine whether simply changing the structure of the core from a tri-layered core to a bi-layered core would be sufficient to substantially reduce the ethanol-related dose-dumping observed with the CONCERTA® osmotic device.

As noted above, the CONCERTA® osmotic device is covered by U.S. Pat. No. 9,144,549 and other related patents sharing substantially the same disclosure. Comparator bi-layered osmotic devices (P-MTH) similar in composition to the CONCERTA® osmotic device were made according to Example 2 of the '549 Patent, which provides MPH release data. Unfortunately, the '549 Patent does not provide sufficient guidance as to the performance of key steps of the process for making the bi-layered core osmotic device, so various batches (P-MTH-01, P-MTH-02A, P-MTH-02B, and P-MTH-02C) were made. The batches varied according to the acetone:water ratio in the blend used to dissolve the semipermeable membrane excipients and the spray rate used to spray the semipermeable membrane suspension (Example 5).

Figure 9A:
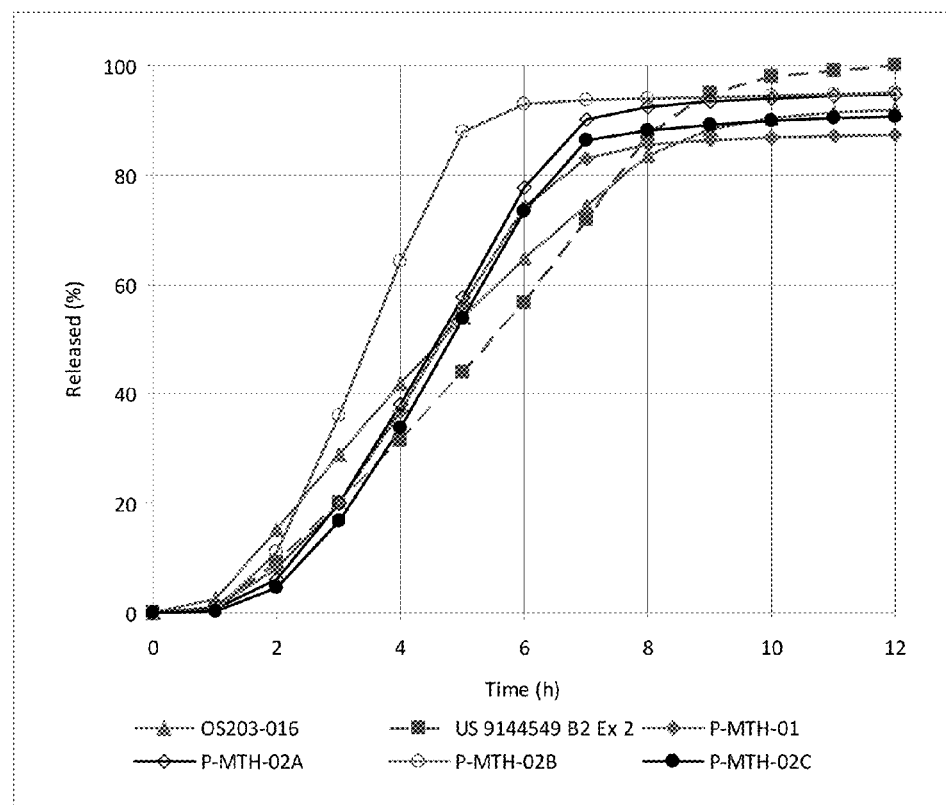
FIG. 9A depicts exemplary in vitro overall drug release profiles for four osmotic devices made according to Example 2 of U.S. Pat. No. 9,144,549 (P-MTH-01, P-MTH-02A, P-MTH-02B, and P-MTH-02C; each 14.08 mg MPH strength) and for an osmotic device of the invention (OS203-016) in water at pH 3.0 in an Apparatus 7 dissolution device along with the release profile disclosed in Example 2 of U.S. Pat. No. 9,144,549.

FIG. 9A depicts exemplary in vitro overall drug release profiles for the core of four comparator osmotic devices made according to Example 2 of U.S. Pat. No. 9,144,549 (P-MTH-01 (filled diamond), P-MTH-02A (open diamond), P-MTH-02B (open circle), and P-MTH-02C (filled circle), each 14.08 mg MPH strength manufactured as disclosed in Example 5; the release profile disclosed in Example 2 of U.S. Pat. No. 9,144,549 (filled square), and the release profile for the 36 mg MPH strength osmotic device of the invention OS203-016 (filled triangle) manufactured as disclosed in Example 6.

Figure 9B:
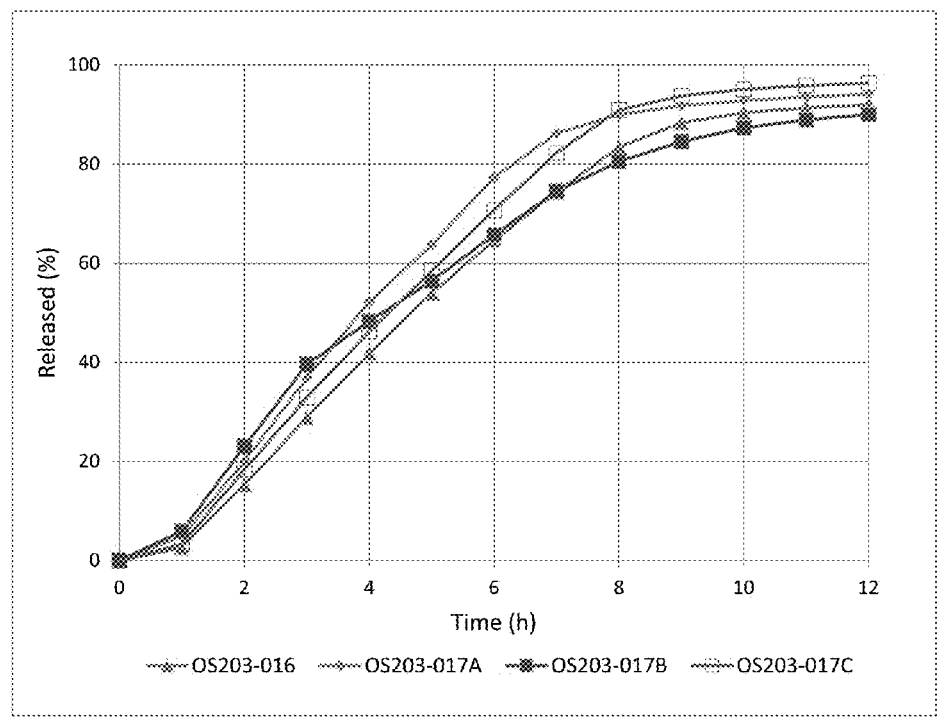
FIG. 9B depicts exemplary in vitro overall drug release profiles for four osmotic devices of the invention (OS203-016, OS203-017A, OS203-017B and OS203-017C; each 29.5 mg MPH strength) in water at pH 3.0 in an Apparatus 7 dissolution device.

FIG. 9B depicts exemplary in vitro overall drug release profiles for the core of four 36 mg MPH strength osmotic device of the invention manufactured as disclosed in Example 6, (OS203-016 (filled triangle), OS203-017A (filled diamond), OS203-017B (filled square), and OS203-017C (open square)), in water at pH 3.0 in an Apparatus 7 dissolution device. None of the osmotic devices contained an IR coating, so the release data represents only drug released from the coated core. The release data was obtained as described in the '549 Patent. As evidenced by similarities in their ascending MPH release rates and their sigmoidal release profiles throughout the first 5 to 6 h and similarities in their total amounts of drug released after about 8 h, three of the four comparator osmotic devices are similar to the osmotic device as described in the '549 Patent (filled squares).

Figure 9C:
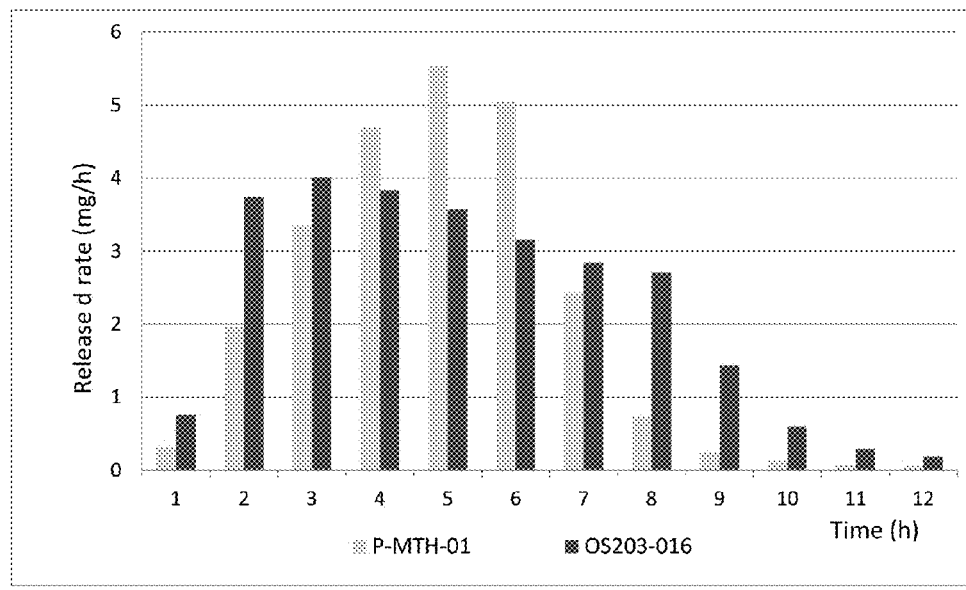
FIG. 9C depicts a comparison of the rate of drug release in mg/hour for osmotic devices P-MTH-01 and OS203-016.

FIG. 9C depicts a comparison of the rate of drug release in mg/hour for the core of osmotic devices P-MTH-01 and OS203-016. Osmotic device P-MTH-01 provides an ascending rate of drug release through the period of 1 h to 5 h and osmotic device OS203-016 generally provides a descending rate of drug release through the period of 3 h to 12 h.

Figure 9D:
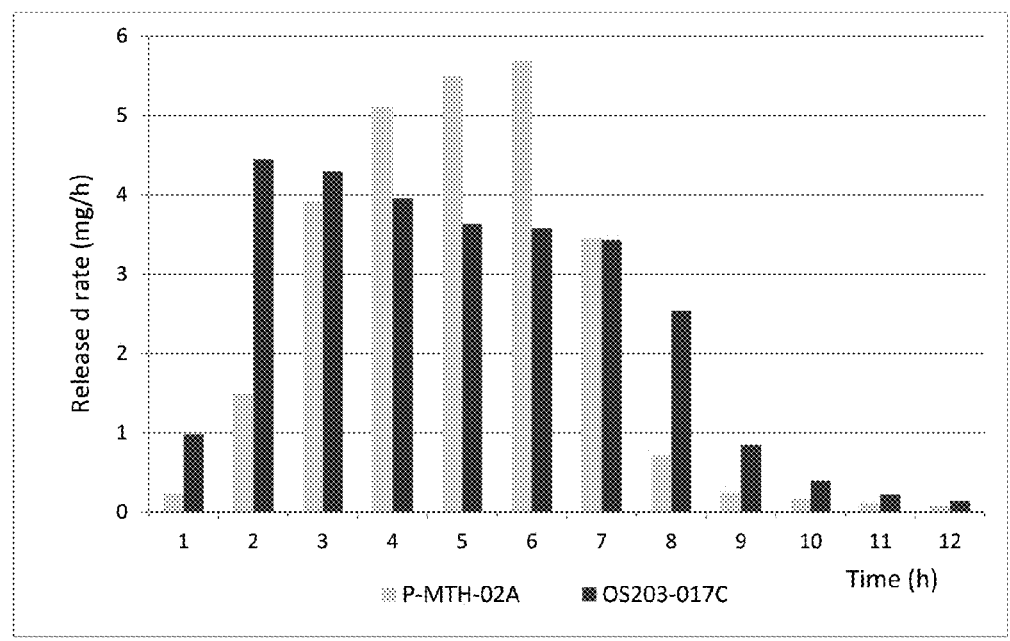
FIG. 9D depicts a comparison of the rate of drug release in mg/hour for osmotic devices P-MTH-02A and OS203-017C.

FIG. 9D depicts a comparison of the rate of drug release in mg/hour for the core of osmotic devices P-MTH-02A and OS203-017C. Osmotic device P-MTH-02A provides an ascending rate of drug release through the period of 1 h to 6 h and osmotic device OS203-017C generally provides a descending rate of drug release through the period of 2 h to 12 h.

Figure 9E:
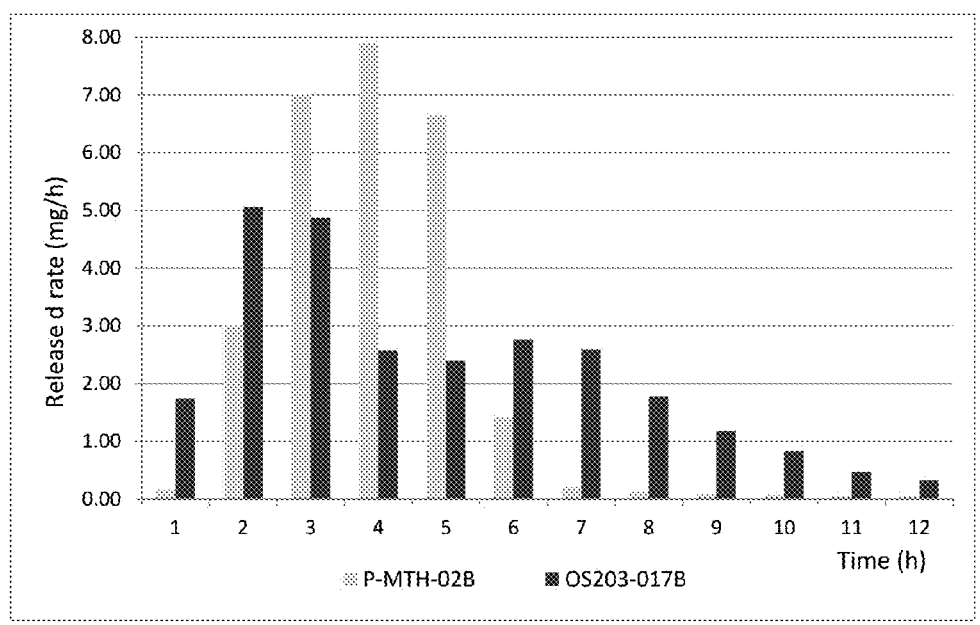
FIG. 9E depicts a comparison of the rate of drug release in mg/hour for osmotic devices P-MTH-02B and OS203-017B.

FIG. 9E depicts a comparison of the rate of drug release in mg/hour for the core of osmotic devices P-MTH-02B and OS203-017B. Osmotic device P-MTH-02B provides an ascending rate of drug release through the period of 1 h to 4 h and osmotic device OS203-017B generally provides a descending rate of drug release through the period of 2 h to 12 h.

Figure 9F:
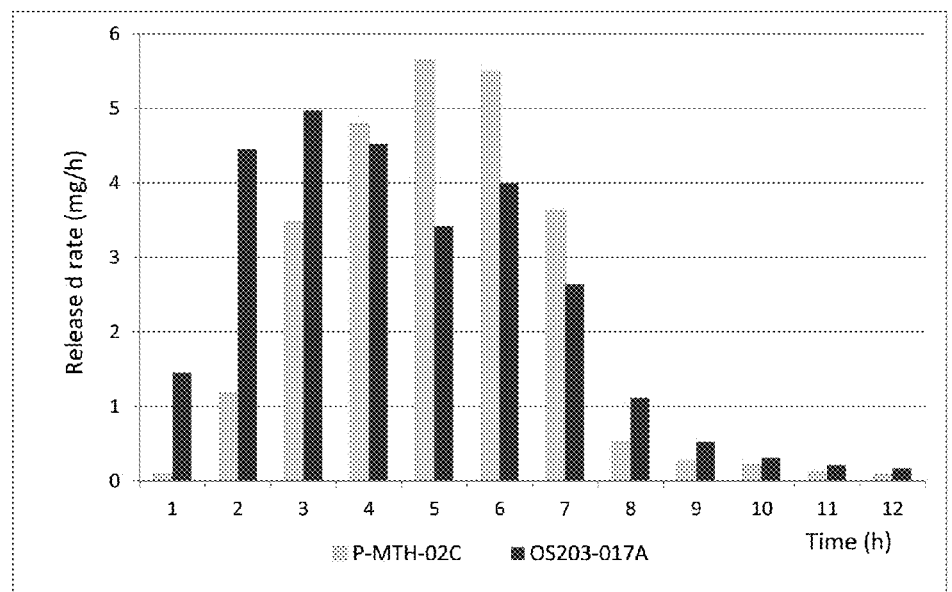
FIG. 9F depicts a comparison of the rate of drug release in mg/hour for osmotic devices P-MTH-02C and OS203-017A.

FIG. 9F depicts a comparison of the rate of drug release in mg/hour for the core of osmotic devices P-MTH-02C and OS203-017A. Osmotic device P-MTH-02C provides an ascending rate of drug release through the period of 1 h to 5 h and osmotic device OS203-017A generally provides a descending rate of drug release through the period of 3 h to 12 h.

Unlike the comparator osmotic devices, the osmotic devices of the invention do not provide an ascending rate of drug release through the period of 1 h to 4 h, 1 h to 5 h or 1 h to 6 h, and instead generally provide a descending rate of drug release through the period of 2 h to 12 h or 3 h to 12 (FIGS. 9C, 9D, 9E and 9F).

Figure 10:
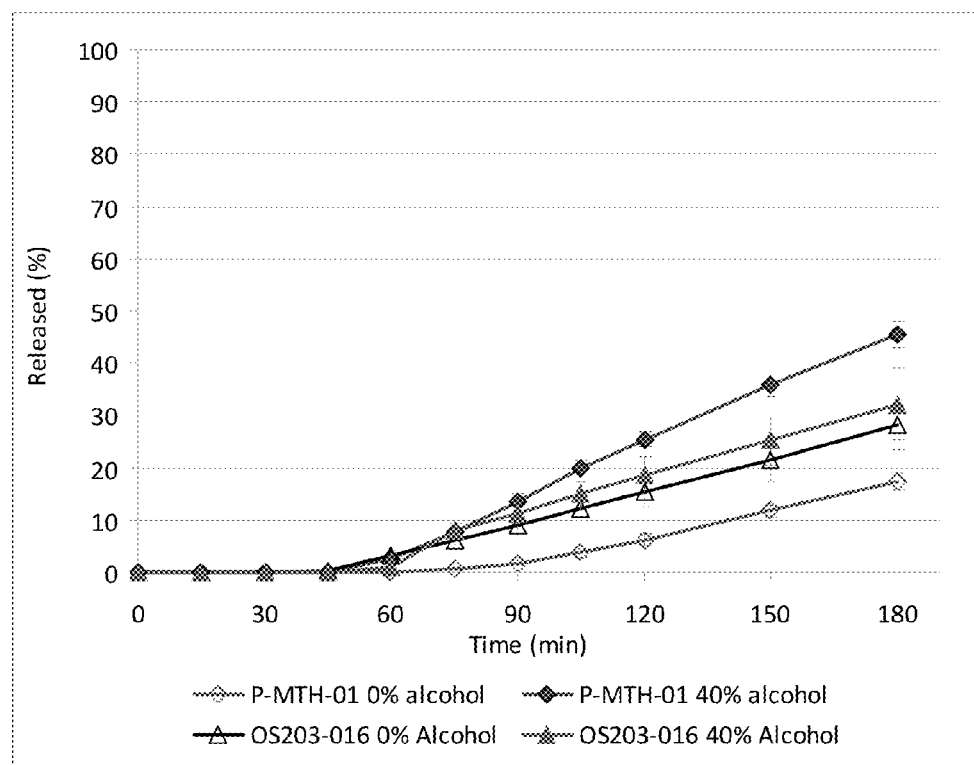
FIG. 10 depicts exemplary in vitro drug release profiles for two osmotic devices according to Example 2 of U.S. Pat. No. 9,144,549 (P-MTH-01; 2 devices of 14.06 mg MPH strength) in the absence (open diamond) and presence of ethanol (filled diamond, 40% ethanol in aqueous 0.1 N HCl at 37±1° C.) and for the osmotic device (OS203-016) of the invention (29.5 mg MPH strength) in the absence (open triangle) and presence of ethanol (filled triangle, 40% ethanol in aqueous 0.1 N HCl at 37±1° C.).

The extent of alcohol-related dose-dumping was evaluated, as described herein, for the comparator osmotic devices. FIG. 10 depicts exemplary in vitro drug release profiles for the core of an osmotic device according to Example 2 of U.S. Pat. No. 9,144,549 (P-MTH-01; 2 devices of 14.06 mg MPH strength) in the absence (open diamond) and presence of ethanol (filled diamond, 40% ethanol in aqueous 0.1 N HCl at 37±1° C.) and for the core of an osmotic device (OS203-016) of the invention (29.5 mg MPH strength) in the absence (open triangle) and presence of ethanol (filled triangle, 40% ethanol in aqueous 0.1 N HCl at 37±1° C.). The following table summarizes the results.

TABLE 15

| Test Parameter | P-MTH-01 (2× 14.06 mg) | OS203-016 (29.5 mg) |
|---|---|---|
| Total release (% @ 2 h in aqueous 0.1N HCl at 37 ± 1° C.) | 5 | 11 |
| Total release (% @ 2 h in 40% ethanol in aqueous 0.1N HCl at 37 ± 1° C.) | 27 | 17 |
| Relative increase in release (= EtOH value/$H_2O$ value) | 5.4 | 1.55 |
| Average release rate (t = 15-120 min, in aqueous 0.1N HCl at 37 ± 1° C.) (%/min) | 0.048 | 0.105 |
| Average release rate (t = 15-120 min, in 40% ethanol in aqueous 0.1N HCl at 37 ± 1° C.) (%/min) | 0.257 | 0.162 |
| Relative increase in average release rate (= EtOH value/$H_2O$ value) | 5.35 | 1.54 |

The instant osmotic device provides a less than 1.6-fold ethanol-related increase in the average rate of MPH release during the time period of 15 min to 120 min, when comparing the release rates in aqueous 0.1 N HCl at 37±1° C. and in 40% ethanol in aqueous 0.1 N HCl at 37±1° C. In comparison, the P-MTH-01 osmotic device provides an over 5.3-fold ethanol-related increase in the average rate of MPH release during the time period of 15 min to 120 min, when comparing the release rates in aqueous 0.1 N HCl at 37±1° C. and in 40% ethanol in aqueous 0.1 N HCl at 37±1° C. The instant osmotic device provides a less than 1.6-fold ethanol-related increase in the total amount of MPH released during the first 120 min, when comparing the release rates in aqueous 0.1 N HCl at 37±1° C. and in 40% ethanol in aqueous 0.1 N HCl at 37±1° C. In comparison, the P-MTH-01 osmotic device provides a 5.4-fold ethanol-related increase in the total amount of MPH released during the first 120 min, when comparing the release rates in aqueous 0.1 N HCl at 37±1° C. and in 40% ethanol in aqueous 0.1 N HCl at 37±1° C.

Figure 11:
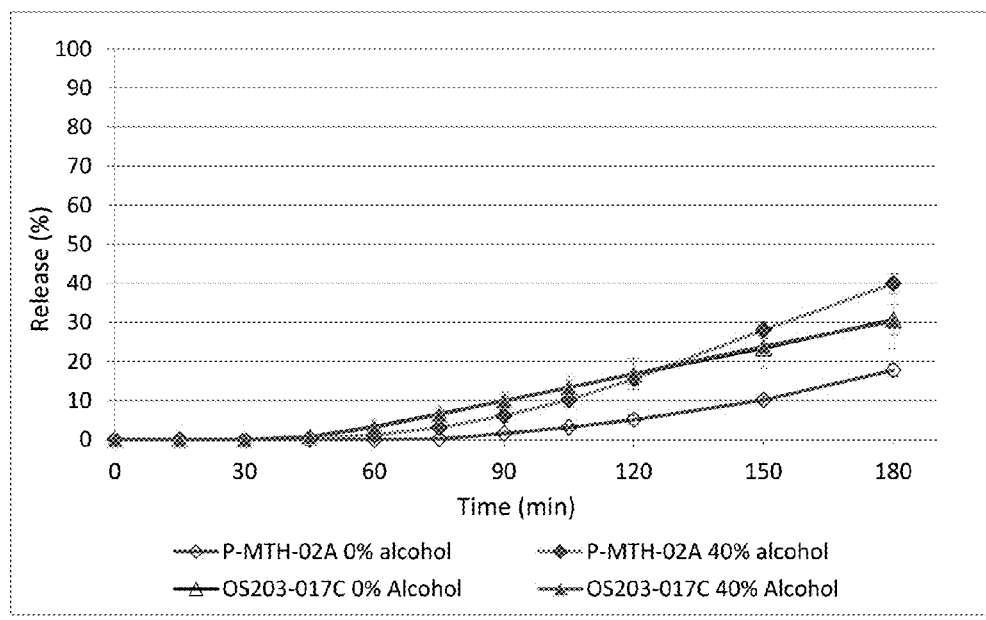
FIG. 11 depicts exemplary in vitro drug release profiles for two osmotic devices according to Example 2 of U.S. Pat. No. 9,144,549 (P-MTH-02A; 2 devices of 14.06 mg MPH strength) in the absence (open diamond) and presence of ethanol (filled diamond, 40% ethanol in aqueous 0.1 N HCl at 37±1° C.) and for the osmotic device (OS203-017C) of the invention (29.5 mg MPH strength) in the absence (open triangle) and presence of ethanol (filled triangle, 40% ethanol in aqueous 0.1 N HCl at 37±1° C.).

FIG. 11 depicts exemplary in vitro drug release profiles for the core of an osmotic device according to Example 2 of U.S. Pat. No. 9,144,549 (P-MTH-02A; 2 devices of 14.06 mg MPH strength) in the absence (open diamond) and presence of ethanol (filled diamond, 40% ethanol in aqueous 0.1 N HCl at 37±1° C.) and for the core of an osmotic device (OS203-017C) of the invention (29.5 mg MPH strength) in the absence (open triangle) and presence of ethanol (filled triangle, 40% ethanol in aqueous 0.1 N HCl at 37±1° C.). The following table summarizes the results.

TABLE 16

| Test Parameter | P-MTH-02A (2× 14.06 mg) | OS203-17C (29.5 mg) |
|---|---|---|
| Total release (% @ 2 h in aqueous 0.1N HCl at 37 ± 1° C.) | 5 | 22 |
| Total release (% @ 2 h in 40% ethanol in aqueous 0.1N HCl at 37 ± 1° C.) | 16 | 19 |
| Relative increase in release (= EtOH value/$H_2O$ value) | 3.2 | 0.86 |
| Average release rate (t = 15-120 min, in aqueous 0.1N HCl at 37 ± 1° C.) (%/min) | 0.048 | 0.209 |
| Average release rate (t = 15-120 min, in 40% ethanol in aqueous 0.1N HCl at 37 ± 1° C.) (%/min) | 0.152 | 0.181 |
| Relative increase in average release rate (= EtOH value/$H_2O$ value) | 3.17 | 0.87 |

The instant osmotic device provides a less than 0.9-fold ethanol-related increase in the average rate of MPH release during the time period of 15 min to 120 min, when comparing the release rates in aqueous 0.1 N HCl at 37±1° C. and in 40% ethanol in aqueous 0.1 N HCl at 37±1° C. In comparison, the P-MTH-02A osmotic device provides an almost 3.2-fold ethanol-related increase in the average rate of MPH release during the time period of 15 min to 120 min, when comparing the release rates in aqueous 0.1 N HCl at 37±1° C. and in 40% ethanol in aqueous 0.1 N HCl at 37±1° C. The instant osmotic device provides a less than 0.9-fold ethanol-related increase in the total amount of MPH released during the first 120 min, when comparing the release rates in aqueous 0.1 N HCl at 37±1° C. and in 40% ethanol in aqueous 0.1 N HCl at 37±1° C. In comparison, the P-MTH-02A osmotic device provides a 3.2-fold ethanol-related increase in the total amount of MPH released during the first 120 min, when comparing the release rates in aqueous 0.1 N HCl at 37±1° C. and in 40% ethanol in aqueous 0.1 N HCl at 37±1° C.

Figure 12:
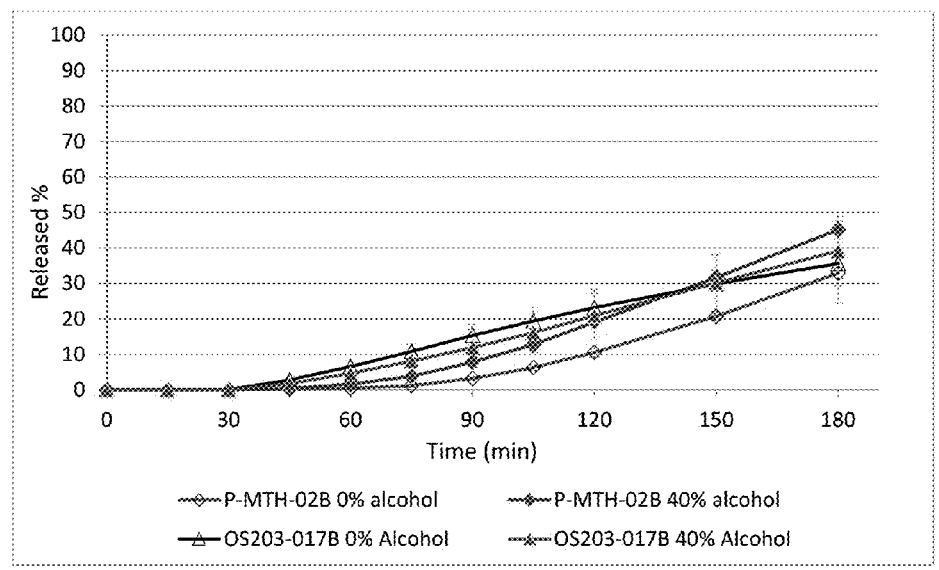
FIG. 12 depicts exemplary in vitro drug release profiles for two osmotic devices according to Example 2 of U.S. Pat. No. 9,144,549 (P-MTH-02B; 2 devices of 14.06 mg MPH strength) in the absence (open diamond) and presence of ethanol (filled diamond, 40% ethanol in aqueous 0.1 N HCl at 37±1° C.) and for the osmotic device (OS203-017B) of the invention (29.5 mg MPH strength) in the absence (open triangle) and presence of ethanol (filled triangle, 40% ethanol in aqueous 0.1 N HCl at 37±1° C.).

FIG. 12 depicts exemplary in vitro drug release profiles for the core of an osmotic device according to Example 2 of U.S. Pat. No. 9,144,549 (P-MTH-02B; 2 devices of 14.06 mg MPH strength) in the absence (open diamond) and presence of ethanol (filled diamond, 40% ethanol in aqueous 0.1 N HCl at 37±1° C.) and for the core of an osmotic device (OS203-017B) of the invention (29.5 mg MPH strength) in the absence (open triangle) and presence of ethanol (filled triangle, 40% ethanol in aqueous 0.1 N HCl at 37±1° C.). The following table summarizes the results.

TABLE 17

| Test Parameter | P-MTH-02B (2× 14.06 mg) | OS203-017B (29.5 mg) |
|---|---|---|
| Total release (% @ 2 h in aqueous 0.1N HCl at 37 ± 1° C.) | 11 | 22 |
| Total release (% @ 2 h in 40% ethanol in aqueous 0.1N HCl at 37 ± 1° C.) | 19 | 28 |
| Relative increase in release (= EtOH value/$H_2O$ value) | 1.73 | 1.27 |
| Average release rate (t = 15-120 min, in aqueous 0.1N HCl at 37 ± 1° C.) (%/min) | 0.105 | 0.209 |
| Average release rate (t = 15-120 min, in 40% ethanol in aqueous 0.1N HCl at 37 ± 1° C.) (%/min) | 0.181 | 0.267 |
| Relative increase in average release rate (= EtOH value/$H_2O$ value) | 1.72 | 1.28 |

The instant osmotic device provides a less than 1.3-fold ethanol-related increase in the average rate of MPH release during the time period of 15 min to 120 min, when comparing the release rates in aqueous 0.1 N HCl at 37±1° C. and in 40% ethanol in aqueous 0.1 N HCl at 37±1° C. In comparison, the P-MTH-02B osmotic device provides an over 1.7-fold ethanol-related increase in the average rate of MPH release during the time period of 15 min to 120 min, when comparing the release rates in aqueous 0.1 N HCl at 37±1° C. and in 40% ethanol in aqueous 0.1 N HCl at 37±1° C. The instant osmotic device provides a less than 1.3-fold ethanol-related increase in the total amount of MPH released during the first 120 min, when comparing the release rates in aqueous 0.1 N HCl at 37±1° C. and in 40% ethanol in aqueous 0.1 N HCl at 37±1° C. In comparison, the P-MTH-02B osmotic device provides an over 1.7-fold ethanol-related increase in the total amount of MPH released during the first 120 min, when comparing the release rates in aqueous 0.1 N HCl at 37±1° C. and in 40% ethanol in aqueous 0.1 N HCl at 37±1° C.

Figure 13:
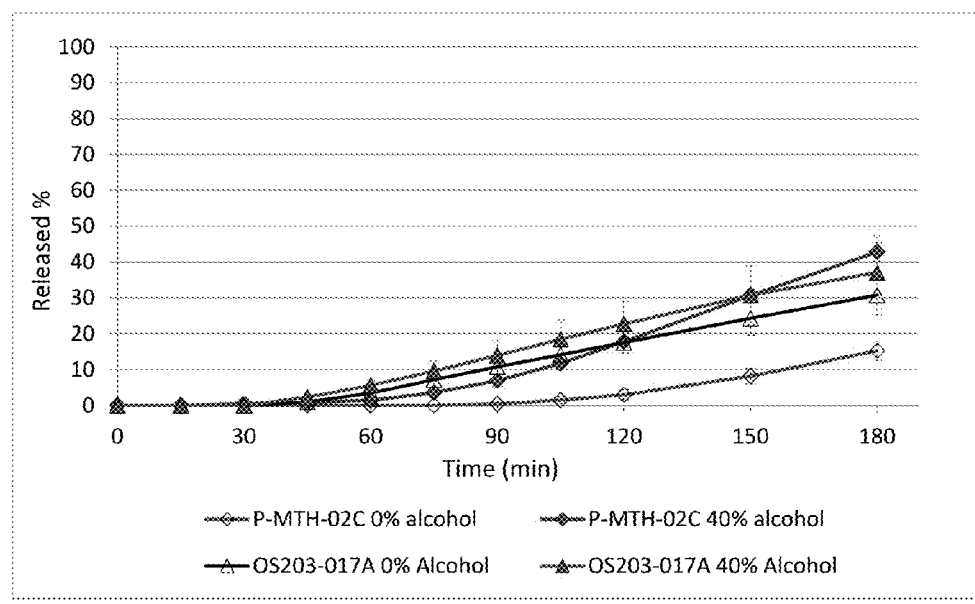
FIG. 13 depicts exemplary in vitro drug release profiles for two osmotic devices according to Example 2 of U.S. Pat. No. 9,144,549 (P-MTH-02C; 2 devices of 14.06 mg MPH strength) in the absence (open diamond) and presence of ethanol (filled diamond, 40% ethanol in aqueous 0.1 N HCl at 37±1° C.) and for the osmotic device (OS203-017A) of the invention (29.5 mg MPH strength) in the absence (open triangle) and presence of ethanol (filled triangle, 40% ethanol in aqueous 0.1 N HCl at 37±1° C.).

FIG. 13 depicts exemplary in vitro drug release profiles for the core of an osmotic device according to Example 2 of U.S. Pat. No. 9,144,549 (P-MTH-02C; 2 devices of 14.06 mg MPH strength) in the absence (open diamond) and presence of ethanol (filled diamond, 40% ethanol in aqueous 0.1 N HCl at 37±1° C.) and for the core of an osmotic device (OS203-017A) of the invention (29.5 mg MPH strength) in the absence (open triangle) and presence of ethanol (filled triangle, 40% ethanol in aqueous 0.1 N HCl at 37±1° C.). The following table summarizes the results.

TABLE 18

| Test Parameter | P-MTH-02C (2× 14.06 mg) | OS203-017A (29.5 mg) |
|---|---|---|
| Total release (% @ 2 h in aqueous 0.1N HCl at 37 ± 1° C.) | 2 | 19 |
| Total release (% @ 2 h in 40% ethanol in aqueous 0.1N HCl at 37 ± 1° C.) | 17 | 20 |
| Relative increase in release (= EtOH value/H₂O value) | 8.5 | 1.05 |
| Average release rate (t = 15-120 min, in aqueous 0.1N HCl at 37 ± 1° C.) (%/min) | 0.019 | 0.181 |
| Average release rate (t = 15-120 min, in 40% ethanol in aqueous 0.1N HCl at 37 ± 1° C.) (%/min) | 0.162 | 0.190 |
| Relative increase in average release rate (= EtOH value/H₂O value) | 8.5 | 1.05 |

The instant osmotic device provides a less than 1.1-fold ethanol-related increase in the average rate of MPH release during the time period of 15 min to 120 min, when comparing the release rates in aqueous 0.1 N HCl at 37±1° C. and in 40% ethanol in aqueous 0.1 N HCl at 37±1° C. In comparison, the P-MTH-02A osmotic device provides an 8.5-fold ethanol-related increase in the average rate of MPH release during the time period of 15 min to 120 min, when comparing the release rates in aqueous 0.1 N HCl at 37±1° C. and in 40% ethanol in aqueous 0.1 N HCl at 37±1° C. The instant osmotic device provides a less than 1.1-fold ethanol-related increase in the total amount of MPH released during the first 120 min, when comparing the release rates in aqueous 0.1 N HCl at 37±1° C. and in 40% ethanol in aqueous 0.1 N HCl at 37±1° C. In comparison, the P-MTH-02B osmotic device provides an 8.5-fold ethanol-related increase in the total amount of MPH released during the first 120 min, when comparing the release rates in aqueous 0.1 N HCl at 37±1° C. and in 40% ethanol in aqueous 0.1 N HCl at 37±1° C.

It is evident that simply changing the structure of the core of the osmotic device from a tri-layered core (CONCERTA® osmotic device) to a bi-layered core (Example 2 of the '549 Patent and the instant osmotic devices) is not sufficient to reduce the alcohol-related dose-dumping of an osmotic device similar in composition to the CONCERTA® osmotic device.

As evidenced herein, the coated core of the instant osmotic device provides improved resistance toward alcohol-related dose dumping and improved pH independence of drug release while at the same time providing controlled release of MPH according to a first order, pseudo-first order, zero order or pseudo-zero order release profile over an extended period of time.

The exemplary release profile described below is for release of drug (MPH) from the core of an osmotic device of the invention using the charge of drug in the core as the basis for calculation and using the methods described herein.

TABLE 19

| Time (hr) | Deionized water Dissolution (% wt) Median or mean range | Deionized water Dissolution (% wt) Median or mean range | Deionized water Dissolution (% wt) Median or mean range | Deionized water Dissolution (% wt) Median or mean range |
|---|---|---|---|---|
| 1 | <10 | <10 | <10 | <10 |
| 2 | 10-30 | 5-30 | 10-25 | 10-22 |
| 4 | 35-60 | 30-60 | 30-55 | 30-50 |
| 6 | 55-85 | 50-85 | 55-85 | 50-70 |
| 8 | ≥70 | ≥70 | ≥70 | 75-95 |
| 10 | ≥80 | ≥80 | ≥80 | ≥80 |
| 1 | 11-31 | 15-30 | | |
| 2 | | 30-40 | | |
| 4 | 38-62 | 50-70 | | |
| 6 | | 75-95 | | |
| 8 | | ≥80 | | |
| 10 | ≥80 | ≥90 | | |

Figure 14:
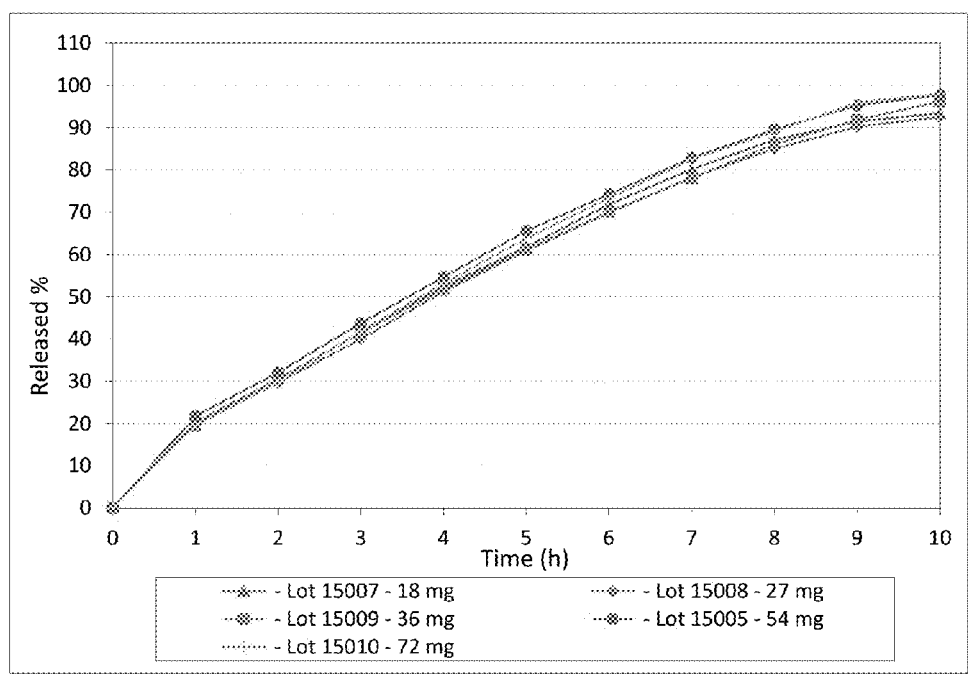
FIG. 14 depicts the overall in vitro dissolution profile, for osmotic devices of the invention (18 mg to 72 mg total dose). The release profiles were determined in water according to Example 4.

The instant osmotic device can comprise an immediate release or release coating exterior to the semipermeable membrane. The coating can comprise MPH such that the total dose of MPH in an osmotic device equals the sum of the charge in the coating and the charge in core. FIG. 14 depicts the overall in vitro dissolution profile, determined as described herein, for osmotic devices of the invention (18 mg to 72 mg total dose). The release profile, as defined by % wt released over time, exhibits little dependence upon the amount of MPH present in the core.

When the instant osmotic device comprises a MPH-containing coating exterior to the membrane coated core, the total dose of MPH in the osmotic device can be divided as follows: 1-40% wt in the coating and 99-60% wt in the core, 10-40% wt in the coating and 90-60% wt in the core, 15-35% wt in the coating and 85-65% wt in the core, 15-25% wt in the coating and 85-75% wt in the core, or 15-20% wt in the coating and 85-80% wt in the core. In some embodiments, there is about 18% wt of MPH in the coating and about 82% wt of MPH in the coated core. In some embodiments, there is 20% wt or less of MPH in the coating and about 80% wt or more of MPH in the coated core. In some embodiments, there is about 22% wt of MPH in the coating and about 78% wt of MPH in the coated core. In some embodiments, the dosage form does not comprise a drug-containing coating exterior to the membrane.

The amount of therapeutic compound incorporated in each device will be at least one or more unit doses and can be selected according to known principles of pharmacy. An effective amount of therapeutic compound is specifically contemplated. By the term "effective amount", it is understood that, with respect to, for example, pharmaceuticals, a pharmaceutically (therapeutically) effective amount is contemplated. A pharmaceutically effective amount is the amount or quantity of a drug or pharmaceutically active substance which is sufficient to elicit the required or desired therapeutic response, or in other words, the amount which is sufficient to elicit an appreciable biological response when administered to a patient.

In some embodiments, MPH (as either the freebase or as a salt) is present in an osmotic device at total dose strength of about 2.5 mg to about 90 mg or about 2.5 mg to about 72 mg, about 20 mg to about 80 mg, or about 18 mg to about 72 mg. Specific total doses include all integers and fractions thereof within the above-noted ranges. Exemplary specific total doses include about 2.5 mg, about 5 mg, about 7.5 mg, about 9 mg, about 10 mg, about 12.5 mg, about 14 mg, about 15 mg, about 17.5 mg, about 18 mg, about 20 mg, about 25 mg, about 27 mg, about 30 mg, about 35 mg, about 36 mg, about 40 mg, about 45 mg, about 50 mg, about 54 mg, about 60 mg, about 63 mg, about 70 mg, about 72 mg, about 75 mg, about 80 mg, about 81 mg, or about 90 mg.

It is known that renally impaired subjects might experience drug accumulation, thereby causing higher Cmax and AUC values as compared to subjects with healthy renal functions. Accordingly, the doses described herein can be reduced further as needed for patients with impaired renal function. The level of dose reduction can be determined by a supervising clinician according to the subject's extent of renal impairment. Typically, the greater the impairment, the lower the dose required to provide therapeutically effective plasma levels of drug.

The term "unit dosage form" is used herein to mean a device containing a quantity of the drug, said quantity being such that one or more predetermined units may be provided as a single therapeutic administration.

As evidenced herein, the coated core of the instant osmotic device provides improved resistance toward alcohol-related dose dumping and improved pH independence of drug release while at the same time providing controlled release of MPH according to a first order, pseudo-first order, zero order or pseudo-zero order release profile over an extended period of time.

By "bi-layered core" is meant the core of an osmotic device that is divided into two layers: a MPH-containing pull layer and a water swellable push layer. The core is considered to be the composition enclosed within the wall, e.g. semipermeable membrane, of the osmotic device. The ingredients of the individual layers may be present as a heterogeneous mixture or homogeneous mixture. A homogeneous mixture is one wherein all of the ingredients have been thoroughly mixed such that the composition of the formulation is substantially the same throughout different portions of the respective layer. The combined step of mixing and directly compressing the ingredients of that layer generally provides a homogeneous mixture. A heterogeneous mixture is one wherein the ingredients of the respective layers are divided into two or more groups that are processed separately to form two or more respective blends, at least one of which contains drug and at least one of which contains a pharmaceutical excipient. The blends are then mixed together and compressed to form the respective layer. A heterogeneous mixture can be obtained by wet granulation, dry granulation, pelleting or combinations thereof.

The weight ratio of pull layer to push layer may impact the release profile of the osmotic device. In some embodiments, the bi-layered core exhibits a weight ratio of pull layer to push layer of at least 1, at least 1.1, at least 1.2, at least 1.3 at least 1.4, at least 1.5, or at least 1.6. In some embodiments, the bi-layered core exhibits a weight ratio of pull layer to push layer of 1.1 to 2, 1.2 to 1.7, 1.3 to 1.7, 1.4 to 1.7 or 1.4-1.6. In some embodiments, the bi-layered core exhibits a weight ratio of pull layer to push layer of not less than 1, not less than 0.9 or not less than 0.8.

The terms "osmotic device" and "controlled release dosage form" or "extended release dosage form" are generally used herein interchangeably. An osmotic device is a controlled release device that comprises a semipermeable membrane surrounding the compressed drug-containing core, and optionally one or more other coatings and/or membranes. The preformed passageway is disposed at least through the semipermeable membrane.

The osmotic device can also comprise an inert water soluble or erodible coat composition surrounding the semipermeable membrane. The preformed passageway can be disposed through the inert water soluble or erodible coat composition and the semipermeable membrane or just through the semipermeable membrane.

The invention includes embodiments wherein the membrane does not rupture during use. As used herein, the term "rupture" refers to breakage of the membrane such as by bursting, splitting, cracking, rending, severing, fracturing, tearing, cleaving, forcing open, puncturing, splitting, or ripping. Permissible rupture according to the invention excludes embodiments wherein the membrane breaks catastrophically thereby releasing the entire contents of the core in a burst or rapid manner. The mechanism of rupture, as used herein, is distinguished from mechanisms such as leaching, erosion or dissolution of material from the membrane, e.g. by inclusion of a pore-former in the membrane. The invention includes embodiments wherein the membrane ruptures even though it may also include a pore former. The rupture may occur on one or more faces, ridges, edges, shoulders or seams of the dosage form.

It should be understood that the device can assume any shape or form currently known in the art of osmotic devices. That is, the device may assume any different shape and/or size according to which are optimal for the intended environment of use. In some embodiments, its compressed core will comprise one or more shoulders, ridges, seams or edges covered by the membrane. In particular embodiments, the shape and size of the device will be optimal for use in subject mammals such as animals or human beings. The device can also include surface markings, cuttings, grooves, letters and/or numerals for the purposes of decoration, identification and/or other purposes.

In some embodiments, the core of the tablet includes one or more ridges, edges, shoulders or seams. In some embodiments, the shape of the tablet can be a cylinder, an ellipsoid of revolution or spheroid such that it does not comprise an edge or shoulder.

The examples disclose controlled release device formulations that differ in the composition of the core, a layer of the core and the semipermeable membrane.

Osmotically effective solutes or osmotic agents, i.e. osmagents, that are capable of being totally or partially solubilized in the fluid, can be included in one or both layers of the core. These osmagents will aid in either the suspension or dissolution of the active agent in the core. Osmotic salts are salt forms of osmagents. Exemplary osmagents include organic and inorganic compounds such as salt, acid, base, chelating agent, halide salt, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are widely known in the art. In some embodiments, a halide salt is preferred. In some embodiments, the preferred halide salt is sodium chloride or potassium chloride. In some embodiments, the preferred halide salt has an ion in common with the MPH salt.

These osmagents can also be incorporated to the core of the osmotic device or a layer thereof to control the release of an active agent therein. In some embodiments, at least one osmotic salt is included in the push-layer.

Osmopolymers are well known to those of ordinary skill in the osmotic device art and well described in the patent and scientific literature. Osmopolymers may be of plant or animal origin, or synthetic. One or more osmopolymers (water swellable excipient(s), water swellable agent(s), water swellable polymer(s)) are present in the core to aid in the delivery of the MPH. A "swellable" agent is any material that increases its volume upon exposure to a solution, such as a polymeric sorbent, for example, sodium polyacrylate, sodium polyacrylamide, poly-N-vinylpyrrolidone, poly-vinyltoluenesulfonate, poly-sulfoethyl acrylate, poly-2-hydroxyethyl acrylate, poly-vinylmethyloxazolidinone, hydrolyzed polyacrylamide, polyacrylic acid, copolymers of acrylamide and acrylic acid, and alkali metal salts of such of the polymers as contain sulfonate or carboxylate groups (see U.S. Pat. No. 3,926,891; U.S. Pat. No. 3,699,103, U.S. Pat. No. 5,693,411, all herein incorporated by reference in their entirety), or a naturally occurring water-swellable agent, such as mangrot seed, ground root of the buuk plant, cotton and sponge.

Examples of osmopolymers include: poly(hydroxy-alkyl methacrylates) with molecular weight of 30,000 to 5,000,000, poly(vinylpyrrolidone) with molecular weight of 10,000 to 360,000, anionic and cationic hydrogels, polyelectrolyte complexes, poly(vinyl alcohol) having low acetate residual, optionally cross-linked with glyoxal, formaldehyde or glutaraldehyde and having a degree of polymerization of 200 to 30,000, a mixture of methyl cellulose, cross-linked agar and carboxymethylcellulose, hydroxyalkyl cellulose, hydroxyalkyl alkylcellulose, hydroxypropyl cellulose, a mixture of hydroxypropyl methylcellulose and sodium carboxymethylcellulose, sodium carboxymethylcellulose, hydroxypropyl methylcellulose, polyethylene oxide, polymers of N-vinyllactams, polyoxyethylene-polyoxypropylene gels, polyoxybutylene-polyethylene block copolymer gels, carob gum, polyacrylic gels, polyester gels, polyurea gels, polyether gels, polyamide gels, polypeptide gels, polyamino acid gels, polycellulosic gels, carbopol acidic carboxy polymers having molecular weights of 250,000 to 4,000,000, Cyanamer polyacrylamides, cross-linked indene-maleic anhydride polymers, Good-Rite™ polyacrylic acids having molecular weights of 80,000 to 200,000, polyalkylene oxide (PAO) polymers, Polyox™ polyethylene oxide (PEO, which is a PAO) polymers having molecular weights of 100,000 to 5,000,000, starch graft copolymers, and Aqua-Keeps™ acrylate polymer polysaccharides.

In some embodiments, the core or a layer thereof comprises two different water swellable polymers (osmopolymers), wherein one polymer is present as a major portion (majority) and the other polymer is present as a minor portion (minority) of the total amount of water swellable polymer present. In some embodiments, the core or a layer thereof comprises polyalkylene oxide (PAO) and hydrophilic cellulose derivative. One or more grades of PEO can be used as the swellable polymer(s) in the core. Some suitable commercially available grades are listed below.

TABLE 21

| POLYOX Grades | Approx. Mol. Wt | Viscosity Range at 25° C. (cP) | | |
|---|---|---|---|---|
| | | 5% Solution | 2% Solution | 1% Solution |
| POLYOX WSR N-10 | 100,000 | 30-50 | | |
| POLYOX WSR N-80 | 200,000 | 55-90 | | |
| POLYOX WSR N-750 | 300,000 | 60-1,200 | | |
| POLYOX WSR N-3000 | 400,000 | 2,250-4,500 | | |
| POLYOX WSR-205 | 600,000 | 4,500-8,800 | | |
| POLYOX WSR N-12K | 1,000,000 | | 400-800 | |
| POLYOX WSR N-60K | 2,000,000 | | 2,000-4,000 | |
| POLYOX WSR-301 | 4,000,000 | | | 1,650-5,500 |
| POLYOX Coagulant | 5,000,000 | | | 5,500-7,500 |
| POLYOX WSR-303 | 7,000,000 | | | 7,500-10,000 |

In some embodiments, the PEO has a molecular weight of: about 7,000,000 or less, about 5,000,000 or less, about 4,000,000 or less, about 3,000,000 or less, about 2,000,000 or less, about 1,000,000 or less, about 1,000,000, about 600,000, about 400,000, about 300,000, about 200,000 or about 100,000. In some embodiments, the PEO has a molecular weight of 200,000 and 7,000,000. A combination of two or more grades of PEO can be used.

Osmopolymers swell or expand to an equilibrium state when exposed to water or other biological fluids. This volume expansion is used to physically force the pharmaceutical agent out through openings that have been formed in the wall, shell or coating during manufacture. Exemplary osmopolymers are disclosed in U.S. Pat. Nos. 5,422,123; 4,783,337; 4,765,989; 4,612,008; 4,327,725; 4,609,374; 4,036,228; 4,992,278; 4,160,020; 4,615,698. The osmopolymers generally swell or expand to a very high degree, usually exhibiting a 2 to 60 fold volume increase. The osmopolymers can be non-cross-linked or cross-linked. The swellable, hydrophilic polymers are, in some embodiments, lightly cross-linked, such as cross-links being formed by covalent or ionic bonds.

Suitable hydrophilic (and/or water swellable) cellulose derivatives include alkycellulose, hydroxyalkylcellulose, carboxyalkyl or hydroxyalkyl alkylcellulose among others. In some embodiments, alkyl is methyl, ethyl or propyl. In some embodiments, hydroxyalkyl is hydroxymethyl, hydroxyethyl or hydroxypropyl. Alkyl and hydroxyalkyl are independently selected upon each occurrence. Suitable types include carboxymethylcellulose (free acid and/or salt form, e.g. sodium or potassium salt), hydroxypropyl methylcellulose (HPMC, hypromellose, METHOCEL E, METHOCEL K, METHOCEL F, METOLOSE 60SH, METOLOSE 65SH, METOLOSE 90SH), methylcellulose (METHOCEL A, METOLOSE SM), hydroxymethylcellulose, hydroxypropylcellulose, hydroxyethylcellulose, ethylcellulose, propylcellulose, hydroxyethyl methylcellulose and others.

One or more grades of HPMC can be used as the water swellable polymer(s) and/or as the hydrophilic polymer in the core. Some suitable commercially available grades (hypromellose, METHOCEL E, METHOCEL K, METHOCEL A) are listed below.

TABLE 22

| Grade | Methoxyl content (%) | Hydroxy-propyl content (%) | Viscosity* (mPa-s) |
|---|---|---|---|
| METHOCEL E premium (group) | 28-30 | 7-12 | |
| METHOCEL E3 premium LV | 28-30 | 7-12 | 2.4-3.6 |
| METHOCEL E5 Premium LV | 28-30 | 7-12 | 4-6 |
| METHOCEL E6 premium LV | 28-30 | 7-12 | 4.8-7.2 |
| METHOCEL E15 premium LV | 28-30 | 7-12 | 12-18 |
| METHOCEL E50 premium LV | 28-30 | 7-12 | 40-60 |
| METHOCEL K premium (group) | 19-24 | 7-12 | |
| METHOCEL K3 premium LV | 19-24 | 7-12 | 2.4-3.6 cps |
| METHOCEL K4M | 19-24 | 7-12 | 2,663-4,970 |
| METHOCEL K15M | 19-24 | 7-12 | 13,275-24,780 |
| METHOCEL K100LV | 22-24 | 7-12 | 80-120 |
| METHOCEL K100M | 19-24 | 7-12 | 75,000-140,000 |
| METHOCEL F premium (group) | 27-30 | 4-7.5 | |
| Hypromellose type 1828 | 16.5-20.0 | 23.0-32.0 | |
| Hypromellose type 2208 | 19.0-24.0 | 4.0-12.0 | |
| Hypromellose type 2906 | 27.0-30.0 | 4.0-7.5 | |
| Hypromellose type 2910 | 28.0-30.0 | 7.0-12.0 | |
| METOLOSE 60SH (type 2910) | 28.0-30.0 | 7.0-12.0 | 50-10,000 |
| METOLOSE 65 SH (type 2906) | 27.0-30.0 | 4.0-7.5 | 50-4,000 |
| METOLOSE 90SH (type 2208) | 19.0-24.0 | 4.0-12.0 | 100-15,000 |
| METHOCEL A premium (group) | 27.5-31.5 | 0 | |
| METHOCEL A15 premium LV | 27.5-31.5 | 0 | 12-18 |
| METHOCEL A4C | 27.5-31.5 | 0 | 320-480 |
| METHOCEL A15C | 27.5-31.5 | 0 | 1,298-2,422 |
| METHOCEL A4M | 27.5-31.5 | 0 | 2,663-4,970 |
| METOLOSE SM | 27.5-31.5 | 0 | 32-5,600 |

In some embodiments, the water swellable PEO is present in a greater amount than the hydrophilic cellulose derivative. In some embodiments, the core or a layer thereof comprises PEO and HPMC. In some embodiments, the PEO is present in a greater amount than the HPMC. In some embodiments, the weight ratio of PEO to HPMC in the core ranges from about 5 to about 8.

In some embodiments, the core or a layer thereof comprises at least one water swellable polymer and at least one osmagent.

Many common materials known by those of ordinary skill in the art are suitable for use as the semipermeable membrane. Exemplary materials include cellulose esters, cellulose ethers, cellulose esters-ethers and combinations thereof. Representative materials for making the semipermeable membrane include a member selected from the group consisting of cellulose acylate, cellulose diacylate, cellulose triacylate, cellulose acetate, cellulose diacetate, cellulose triacetate, mono, di and tricellulose alkanylates, mono, di and tricellulose aroylates, and the like. Exemplary polymers include cellulose acetate having a D.S. up to 1 and an acetyl content up to 21%; cellulose acetate having an acetyl content of 32 to 39.8%; cellulose diacetate having a D.S. of 1 to 2 and an acetyl content of 21 to 35%; cellulose triacetate having a degree of substitution (D.S.) of 2 to 3 and an acetyl content of 35 to 44.8%; and the like. More specific cellulosic polymers include cellulose propionate having a D.S. of 1.8 and a propionyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, and cellulose trioclanoate; cellulose diacylates having a D.S. of 2.2 to 2.6 such as cellulose disuccinate, cellulose dipalmitate, cellulose dioclanoate, cellulose dipentalate, and the like. Additional semipermeable polymers include acetaldehyde dimethyl acetate, cellulose acetate ethyl carbamate, cellulose acetate phthalate for use in environments having a low ph, cellulose acetate methyl carbamate, cellulose acetate dimethyl aminoacetate, semipermeable polyamides, semipermeable polyurethanes, semipermeable sulfonated polystyrenes, cross-linked selectively semipermeable polymers formed by the coprecipitation of a polyanion and a polycation as disclosed in U.S. Pat. Nos. 3,173,876, 3,276,586, 3,541,005, 3,541,006, and 3,546,142; semipermeable polymers as disclosed by Loeb and Sourirajan in U.S. Pat. No. 3,133,132; lightly cross-linked polystyrene derivatives; cross-linked poly(sodium styrene sulfonate), cross-linked poly(vinylbenzyltrimethyl ammonium chloride). These and others polymers are disclosed in U.S. Pat. Nos. 3,845,770, 3,916,899, 4,765,989 and 4,160,020; and in Handbook of Common Polymers (Scott, J. R. and Roff, W. J., eds.; 1971; CRC Press, Cleveland, Ohio).

The cellulose esters differ in their cellulose chain length and the type and amount of ester groups attached to the chain. For cellulose acetates, as the amount of acetyl content increases, the water permeability decreases. The cellulose acetate grade 3 comprises 7-10% by weight of hydroxyl groups and has a viscosity of 200-280 seconds as determined by ASTM Method D 1343. The cellulose acetate grade 4 comprises 3-5% by weight of hydroxyl groups and has a viscosity of 6 to 45 seconds. The cellulose acetate grade 5 comprises 3-5% by weight of hydroxyl groups and has a viscosity of 100 to 240 seconds.

Some exemplary grades of cellulose acetate that are suitable for use in the making the semipermeable membrane are also described in the table below, which is included by way of example. Cellulose acetate of differing grades is readily available from Eastman Chemical Company (Kingsport, Tenn., USA).

TABLE 23

| Cellulose Acetate | Hydroxyl Content (% by wt.) | Acetyl Content (% by wt.) | Viscosity* |
|---|---|---|---|
| Grade 1 | 8.7 | 32 | 2.4 P |
| Grade 2 | 3.5 | 39-40, 39.8 | 38 P |
| Grade 3 | 7-10 | 30-36 | 200-280 sec* |
| Grade 4 | 3-5 | 37-43 | 6-45 sec* |
| Grade 5 | 3-5 | 37-43 | 100-240 sec* |

*Viscosity determined as set forth in ASTM D817 (Formula A) and D1343, the disclosure of which is hereby incorporated by reference.

The above amounts are approximate (about) due to lot-to-lot manufacturing variations. Grade 1 can be considered a more narrowly defined Grade 3. Grade 2 can be considered a more narrowly defined Grade 5. Specific grades of cellulose acetate polymer also include the following.

TABLE 24

| Cellulose Acetate | Average Hydroxyl Content (% by wt.) | Average Acetyl Content (% by wt.) | Avg. Viscosity* (poise) | $MW_n$ |
|---|---|---|---|---|
| CA-394-60S | 4.0 | 39.5 | 228 | ~60000 |
| CA-398-3 | 3.5 | 39.8 | 11.4 | ~30000 |
| CA-398-6 | 3.5 | 39.8 | 22.8 | ~35000 |
| CA-398-10 | 3.5 | 39.8 | 38 | ~40000 |
| CA-398-30 | 3.5 | 39.7 | 114 | ~50000 |
| CA-320-S | 8.7 | 32.0 | 210 | ~18000 |
| CA-435-75S | 0.9 | 43.5 | — | ~122000 |

*Viscosity determined as set forth in ASTM D817 (Formula A) and D1343.

In some embodiments, the semipermeable membrane comprises plasticizer and a single type of film-forming cellulose ester polymer. In some embodiments, the semipermeable membrane comprises plasticizer and a single type of film-forming cellulose ester polymer. In some embodiments, the semipermeable membrane comprises a single grade of cellulose ester. In some embodiments, the semipermeable membrane comprises cellulose acetate ester having an average hydroxyl content of about 3.5-4.0% wt or about 3.5% wt, and an average acetyl content of about 39.5-40% wt or about 39.7-39.8% wt. In some embodiments, the semipermeable membrane comprises cellulose acetate ester exhibiting an average viscosity of about 11 poise to about 120 poise or about 11.4 poise to 114 poise determined per the ASTM methods listed herein.

Plasticizers can be included in the semipermeable membrane to modify the properties and characteristics of the polymers used in the coats or core of the device. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in Poly (ethylene glycol) Chemistry: Biotechnical and Biomedical Applications (J.M. Harris, Ed.; Plenum Press, NY) the disclosure of which is hereby incorporated by reference.

It has been found that a semipermeable membrane consisting essentially of cellulose acetate (CA) and poly(ethylene glycol) (PEG, plasticizer) is particularly advantageous. In some embodiments, PEG 3350 (PEG having an average molecular weight of about 3350), is preferred when used in combination with CA. This particular combination of CA and PEG provides a semipermeable membrane that gives the osmotic device a well controlled release profile for the active agent in the core and that retains its chemical and physical integrity in the environment of use. In some embodiments, the weight ratio of CA:PEG ranges from about 90-99% by weight of CA: about 10-1% by weight of PEG, about 95-99% by weight of CA: about 5-1% by weight of PEG, about 95-98% by weight of CA: about 5-2% by weight of PEG, about 97% by weight of CA: about 3% by weight of PEG. The ratio can be varied to alter permeability and ultimately the release profile of the osmotic device.

The plasticizer can be present in the following amounts or percentages, based upon the weight of the final dried membrane: 0.1-10% wt, 0.1-8% wt, 0.1-6% wt., 1-10% wt, 1-8% wt, 1-5% wt, about 2-4% wt, about 3% wt or other ranges specified herein. The plasticizer can be, esp. PEG 3350, or as otherwise specified herein.

The optional inert polymer coat that covers the semipermeable membrane is made of synthetic, semisynthetic or natural material which, through selective dissolution and/or erosion shall allow the passageway to be unblocked thus allowing the process of osmotic delivery to start. The inert polymer coat will generally comprise an inert and non-toxic material which is at least partially, and generally substantially completely, soluble and/or erodible in an environment of use.

An optional drug-containing coat exterior to the semipermeable membrane may contain a second active agent that may or may not be the same as a first active agent in the core. The coating can comprise MPH, a second active agent or a combination of MPH and a second active agent. The second active agent is available for immediate release. The second active agent can be applied to the surface of the device according to common methods of preparing similar osmotic devices such as applying to its surface solids in solution or suspension through the use of a sprayer that spreads them uniformly over the core or by employing nucleated compression or other suitable methods known to those of ordinary skill in the art. The external coat can comprise poly (vinylpyrrolidone) (PVP) and poly(ethylene glycol) (PEG) and can further comprise materials such as, by way of example and without limitation, hydroxypropyl methylcellulose (HPMC), hydroxyethylcellulose (HEC), sodium carboxymethyl-cellulose (CMC), dimethylaminoethyl methacrylate-methacrylic acid ester copolymer, ethylacrylate-methylmethacrylate copolymer (GA-MMA), C-5 or 60 SH-50 (Shin-Etsu Chemical Corp.) and combinations thereof. The active agent-containing external coat can also comprise dissolution aids, stability modifiers, and bioabsorption enhancers.

As used herein, the term "preformed passageway" refers to a passageway or passageway precursor that has been formed on the semipermeable membrane of the device by mechanical means, such as by a laser, drill and/or etching apparatus. The term "preformed passageway" is not intended to cover pores, holes, apertures, channels or other similar structures formed in the semipermeable membrane by incorporation of pore formers, water soluble particulates, or similar materials known to those of ordinary skill, into the semipermeable membrane of the rupturing controlled release device during manufacture of the osmotic device.

The osmotic device of the invention comprises at least one preformed passageway (pore, hole, or aperture) that communicates the exterior of the semipermeable membrane with the core of the device. The preformed passageway can be formed according to any of the known methods of forming passageways in a semipermeable membrane. Such methods include, for example, 1) drilling a hole through the semipermeable membrane with a bit or laser; 2) punching a hole through the semipermeable membrane; or 3) employing a tablet punch having a pin to punch a hole through the semipermeable membrane. The passageway can pass through the semipermeable membrane and one or more of any other coating onto the semipermeable membrane or between the semipermeable membrane and the core. The passageway(s) can be shaped as desired. In some embodiments, the passageway is laser drilled and is shaped as an oval, ellipse, slot, slit, cross or circle.

Methods of forming preformed passageways in semipermeable membranes of osmotic devices are disclosed in U.S. Pat. No. 4,088,864 to Theeuwes et al., U.S. Pat. No. 4,016,880 to Theeuwes et al., U.S. Pat. No. 3,916,899 to Theeuwes et al., U.S. Pat. No. 4,285,987 to Ayer et al., U.S. Pat. No. 4,783,337 to Wong et al., U.S. Pat. No. 5,558,879 to Chen et al., U.S. Pat. No. 4,801,461 to Hamel et al., U.S. Pat. No. 3,845,770 to Theeuwes et al., PCT International Publication No. WO 04/103349 to Faour, and U.S. Pat. No. 6,809,288 to Faour, the disclosures of which are hereby incorporated by reference.

In some embodiments, the edge of the membrane defining the preformed passageway in the wall does not tear or rupture during use of the osmotic device.

A device according to the present invention can comprise one or more preformed passageways including two, three, four, five, six, seven, eight, nine, ten or more preformed passageways. It is only necessary that the preformed passageways together are adapted to permit controlled release of ingredients from the core during use. In some embodiments, the semipermeable membrane comprises at least one preformed passageway having a diameter ranging from about 0.3 to about 0.7 mm, about 0.4 to about 0.6 mm. In other embodiments, the total area of the preformed passageway(s) present in the membrane ranges from 0.07 mm$^2$ to 0.38 mm$^2$. Preformed passageways of different sizes, shapes and functions can be employed.

Membrane thickness is related to membrane weight, i.e. the final weight of the membrane after preparation. Generally, the thicker the membrane, the heavier it is and the slower the release rate of drug. In some embodiments, a membrane weighing from 15 mg to 35 mg is applied to a core weighing from 200 mg to 600 mg. In some embodiments, the approximate membrane and core weights (based upon the weight of core without the membrane) are in any of the following ranges.

TABLE 25

| Element | Weight (mg) | Weight (mg) | Weight (mg) | Weight (mg) | Weight (mg) | Weight (mg) |
|---|---|---|---|---|---|---|
| Core | 200-250 | 110-140 | 150-220 | 170-200 | 200-300 | 400-600 |
| Membrane | 15-30 | 17-23 or 22-29 | 20-35 | 22-27 or 22-31 | 20-35 | 17-23 or 22-29 |

The osmotic device of the invention can also comprise adsorbents, antioxidants, buffering agents, colorants, flavorants, tablet antiadherents, tablet binders, tablet diluents, tablet fillers, tablet direct compression excipients, tablet glidants, tablet lubricants, tablet opaquants, colorant, acidic agent, alkaline agent and/or tablet polishing agents.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "antioxidant" is intended to mean an agent that inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene (BHT), hypophosphorous acid, monothioglycerol, propyl gallate, sodium ascorbate, sodium bisulfite, sodium formaldehyde sulfoxylate and sodium metabisulfite and other materials known to one of ordinary skill in the art.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and other materials known to one of ordinary skill in the art.

As used herein, the term "tablet binders" is intended to mean substances used to cause adhesion of powder particles in tablet granulations. Such compounds include, by way of example and without limitation, acacia, poly(vinylpyrrolidone), compressible sugar (e.g., NuTab™), ethylcellulose, gelatin, liquid glucose, povidone, copovidone (KOLLIDON® VA 64; BASF Group, Germany), pregelatinized starch, tragacanth, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC F68, PLURONIC F127), collagen, albumin, cellulosics in nonaqueous solvents, combinations thereof and other materials known to one of ordinary skill in the art. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

KOLLIDON® VA 64 (copovidone) is a vinylpyrrolidone-vinyl acetate copolymer that is soluble in water and alcohol. The monomers are present in an approximate molar ratio of 6:4. The copolymer has a molecular weight ranging from 45,000-70,000 as measured by laser light scattering in solution. Additional information can be obtained from BASF (cww.pharma-ingredients.basf.com) or "Kollidon—Polyvinylpyrrolidone excipients for the Pharmaceutical Industry (BASF leaflet 03_030743e).

As used herein, the term "tablet antiadherents" is intended to mean agents which prevent the sticking of tablet formulation ingredients to punches and dies in a tableting machine during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "tablet diluents" or "tablet fillers" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose (MCC), powdered cellulose, precipitated calcium carbonate, sorbitol, and starch and other materials known to one of ordinary skill in the art.

As used herein, the term "tablet direct compression excipient" is intended to mean a compound used in direct compression tablet formulations. Such compounds include, by way of example and without limitation, dibasic calcium phosphate (e.g., Ditab) and other materials known to one of ordinary skill in the art.

As used herein, the term "tablet glidant" is intended to mean agents used in tablet and capsule formulations to promote the flowability of a granulation. Such compounds include, by way of example and without limitation, colloidal silica, cornstarch, talc, calcium silicate, magnesium silicate, colloidal silicon, silicon hydrogel and other materials known to one of ordinary skill in the art.

As used herein, the term "tablet lubricant" is intended to mean substances used in tablet formulations to reduce friction during tablet compression. Such compounds include, by way of example and without limitation, calcium stearate, magnesium stearate, mineral oil, stearic acid, and zinc stearate and other materials known to one of ordinary skill in the art.

As used herein, the term "tablet opaquant" is intended to mean a compound used to render a tablet coating opaque. It may be used alone or in combination with a colorant. Such compounds include, by way of example and without limitation, titanium dioxide and other materials known to one of ordinary skill in the art.

As used herein, the term "tablet polishing agent" is intended to mean a compound used to impart an attractive sheen to coated tablets. Such compounds include, by way of example and without limitation, carnauba wax, and white wax and other materials known to one of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carmine, turmeric, paprika, and other materials known to one of ordinary skill in the art. The amount of coloring agent used will vary as desired.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly preferred flavors are the grape and cherry flavors and citrus flavors such as orange.

It is contemplated that the osmotic device of the invention can also include oils, for example, fixed oils, such as peanut oil, sesame oil, cottonseed oil, corn oil and olive oil; fatty acids, such as oleic acid, stearic acid and isostearic acid; and fatty acid esters, such as ethyl oleate, isopropyl myristate, fatty acid glycerides and acetylated fatty acid glycerides. It can also be mixed with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethyleneglycol) 450, with petroleum hydrocarbons, such as mineral oil and petrolatum; with water, or with mixtures thereof; with or without the addition of a pharmaceutically suitable surfactant, suspending agent or emulsifying agent.

Soaps and synthetic detergents may be employed as surfactants and as vehicles for detergent compositions.

Various other components, not otherwise listed above, can be added to the present formulation for optimization of a desired active agent release profile including, by way of example and without limitation, glycerylmonostearate, nylon, cellulose acetate butyrate, d, 1-poly(lactic acid), 1,6-hexanediamine, diethylenetriamine, starches, derivatized starches, acetylated monoglycerides, gelatin coacervates, poly (styrene-maleic acid) copolymer, glycowax, castor wax, stearyl alcohol, glycerol palmitostearate, poly (ethylene), poly(vinyl acetate), poly(vinyl chloride), 1,3-butylene-glycoldimethacrylate, ethyleneglycoldimethacrylate and methacrylate hydrogels.

As used herein, an acidic agent is a compound or combination of compounds that comprises an acidic moiety. Exemplary acidic agents include organic acid, inorganic acid, mineral acid and a combination thereof. Exemplary acids include hydrochloric acid, hydrobromic acid, sulfuric acid, sulfonic acid, sulfamic acid, phosphoric acid, or nitric acid or others known to those of ordinary skill; and the salts prepared from organic acids such as amino acids, acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulfanilic acid, 2-acetoxybenzoic acid, fumaric acid, toluenesulfonic acid, methanesulfonic acid, ethane disulfonic acid, oxalic acid, isethionic acid and others acids known to those of ordinary skill in the art.

As used herein, an alkaline agent is a compound or combination of compounds that comprises an alkaline moiety. Exemplary alkaline agents include primary amine, secondary amine, tertiary amine, quaternary amine, hydroxide, alkoxide, and a combination thereof. Exemplary alkaline agents include ammonia solution, ammonium carbonate, diethanolamine, monoethanolamine, potassium hydroxide, sodium borate, sodium carbonate, sodium bicarbonate, sodium hydroxide, triethanolamine, diethanolamine, monobasic phosphate salt, dibasic phosphate salt, organic amine base, alkaline amino acids and trolamine and others known to those of ordinary skill in the art.

It should be understood, that compounds used in the art of pharmaceutical formulations generally serve a variety of functions or purposes. Thus, if a compound named herein is mentioned only once or is used to define more than one term herein, its purpose or function should not be construed as being limited solely to that named purpose(s) or function(s).

Particular combinations of active agents that can be provided by the present controlled release device include: 1) a drug in the core from a first therapeutic class and a different drug in the external drug-containing coat from the same therapeutic class; 2) a drug in the core from a first therapeutic class and a different drug in the external drug-containing coat from a different therapeutic class; 3) a drug in the core having a first type of biological activity and a different drug in the external drug-containing coat having about the same biological activity; and/or 4) a drug in the core having a first type of biological activity and a different drug in the external drug-containing coat having a different second type of biological activity.

The therapeutic compound(s), such as MPH or the abusable drug, contained within the present osmotic device can be formulated as its pharmaceutically acceptable salts. As used herein, "pharmaceutically acceptable salts" refer to derivatives of the disclosed compounds wherein the therapeutic compound is modified by making an acid or base salt thereof. Examples of pharmaceutically acceptable salts include, but are not limited to, mineral or organic acid salts of basic residues such as amines; alkali or organic salts of acidic residues such as carboxylic acids; and others known to those of ordinary skill. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfonic, sulfamic, phosphoric, nitric and others known to those of ordinary skill; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill. The pharmaceutically acceptable salts of the present invention can be synthesized from the parent therapeutic compound which contains a basic or acidic moiety by conventional chemical methods. Lists of suitable salts are found in Remington's Pharmaceutical Sciences, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

If desired, the device of the invention can be coated with one or more finish coats as is commonly done in the art to provide the desired shine, color, taste and/or other aesthetic characteristics. Materials suitable for preparing the finish coat are well known in the art and found in the disclosures of many of the references cited and incorporated by reference herein. Printing may also be included in or on the dosage form.

The following examples should not be considered exhaustive, but merely illustrative of only a few of the many embodiments contemplated by the present invention. The methods described herein can be followed to prepare and use dosage forms and methods according to the invention.

In the examples below, ranges are specified for the amount of each ingredient. Ranges including "0" as the lowest value indicate an optional ingredient. Osmotic devices with quantities of ingredients falling within the compositional ranges specified herein were made. Osmotic devices of the invention comprising quantities of ingredients falling within the compositional ranges specified herein operate as intended and as claimed.

Example 1

The following formula is used to prepare controlled release devices containing MPH in the core. The osmotic device tablets contain the following ingredients in the amounts indicated.

| | Component | Amt (mg) | Amt (% wrt layer) |
|---|---|---|---|
| | 1-A | | |
| Tablet Core- Pull Layer | Methylphenidate HCL USP | 14.76 | 10.35 |
| | Hydrophilic polymer | 2.85-28.52 | 2.00-20.00 |
| | Water swellable polymer | 7.13-121.23 | 5.00-85.00 |
| | Optional Acidic agent | 0.00-28.52 | 0.00-20.00 |
| | Optional Lubricant | 0.00-7.13 | 0.00-5.00 |
| Tablet Core Push Layer | Osmotic salt | 0.00-40.00 | 0.00-40.00 |
| | Optional glidant | 0.10-1.00 | 0.10-1.00 |
| | Water swellable polymer | 5.00-85.00 | 5.00-85.00 |
| | Hydrophilic polymer | 2.00-20.00 | 2.00-20.00 |
| | Optional pigment | 0.00-2.40 | 0.00-2.40 |
| | Optional lubricant | 0.00-5.00 | 0.00-5.00 |
| Semipermeable membrane (Coating A) | Film-forming cellulose ester | 14.25-14.85 | 95.00-99.00 |
| | Plasticizer | 0.15-0.75 | 1.00-5.00 |
| IR Coating (Coating B) | Methylphenidate HCL USP | 3.24 | 24.27 |
| | Water soluble polymer | 6.68-11.76 | 50.00-90.00 |
| | Optional acidic agent | 0.00-QS to PH:3 | |
| | 1-B | | |
| Tablet Core- Pull Layer | Methylphenidate HCL USP | 22.14 | 14.76 |
| | Hydrophilic polymer | 3.00-30.00 | 2.00-20.00 |
| | Water swellable polymer | 7.50-127.50 | 5.00-85.00 |
| | Optional Acidic agent | 0.00-30.00 | 0.00-20.00 |
| | Optional Lubricant | 0.00-7.50 | 0.00-5.00 |
| Tablet Core Push Layer | Osmotic salt | 10.00-40.00 | 10.00-40.00 |
| | Optional glidant | 0.00-1.00 | 0.00-1.00 |
| | Water swellable polymer | 5.00-85.00 | 5.00-85.00 |
| | Hydrophilic polymer | 2.00-20.00 | 2.00-20.00 |
| | Optional pigment | 0.00-2.40 | 0.00-2.40 |
| | Optional lubricant | 0.00-5.00 | 0.00-5.00 |
| Semipermeable membrane (Coating A) | Film-forming cellulose ester | 14.25-14.85 | 95.00-99.00 |
| | Plasticizer | 0.15-0.75 | 1.00-5.00 |
| IR Coating (Coating B) | Methylphenidate HCL USP | 4.86 | 24.27 |
| | Water soluble polymer | 10.01-15.16 | 50.00-75.72 |
| | Optional acidic agent | 0.00-QS to PH:3 | |
| | 1-C | | |
| Tablet Core- Pull Layer | Methylphenidate HCL USP | 29.52 | 11.43 |
| | Hydrophilic polymer | 5.70-57.05 | 2.00-20.00 |
| | Water swellable polymer | 14.26-242.45 | 5.00-85.00 |
| | Optional Acidic agent | 0.00-57.05 | 0.00-20.00 |
| | Optional Lubricant | 0.00-14.26 | 0.00-5.00 |
| Tablet Core Push Layer | Osmotic salt | 20.00-80.00 | 10.00-40.00 |
| | Optional glidant | 0.00-2.00 | 0.0-1.00 |
| | Water swellable polymer | 10.00-170.00 | 5.00-85.00 |
| | Hydrophilic polymer | 4.00-40.00 | 2.00-20.00 |
| | Optional pigment | 0.00-4.80 | 0.00-2.40 |
| | Optional lubricant | 0.00-10.00 | 0.00-5.00 |
| Semipermeable membrane (Coating A) | Film-forming cellulose ester | 15.20-15.84 | 95.00-99.00 |
| | Plasticizer | 0.16-8.00 | 1.00-5.00 |
| IR Coating (Coating B) | Methylphenidate HCL USP | 6.48 | 24.26 |

| | Component | Amt (mg) | Amt (% wrt layer) |
|---|---|---|---|
| | Water soluble polymer | 13.35-20.22 | 50.00-75.72 |
| | Optional acidic agent | QS to PH:3 | |

1-D

| | Component | Amt (mg) | Amt (% wrt layer) |
|---|---|---|---|
| Tablet Core-Pull Layer | Methylphenidate HCL USP | 44.28 | 14.76 |
| | Hydrophilic polymer | 6.00-60.00 | 2.00-20.00 |
| | Water swellable polymer | 15.00-255.00 | 5.00-85.00 |
| | Optional Acidic agent | 0.00-60.00 | 0.00-20.00 |
| | Optional Lubricant | 0.00-15.00 | 0.00-5.00 |
| Tablet Core Push Layer | Osmotic salt | 20.00-80.00 | 10.00-40.00 |
| | Optional glidant | 0.00-2.00 | 0.00-1.00 |
| | Water swellable polymer | 10.00-170 | 5.00-85.00 |
| | Hydrophilic polymer | 4.00-40.00 | 2.00-20.00 |
| | Optional pigment | 0.00-4.8 | 0.00-2.40 |
| | Optional lubricant | 0.00-10.00 | 0.00-5.00 |
| Semipermeable membrane (Coating A) | Film-forming cellulose ester | 16.15-16.83 | 95.00-99.00 |
| | Plasticizer | 0.17-0.85 | 1.00-5.00 |
| IR Coating (Coating B) | Methylphenidate HCL USP | 9.72 | 24.26 |
| | Water soluble polymer | 20.04-30.35 | 50.00-75.72 |
| | Optional acidic agent | 0.00-QS to PH:3 | |

1-E

| | Component | Amt (mg) | Amt (% wrt layer) |
|---|---|---|---|
| Tablet Core-Pull Layer | Methylphenidate HCL USP | 59.04 | 14.76 |
| | Hydrophilic polymer | 6.30-62.95 | 2.00-20.00 |
| | Water swellable polymer | 15.74-267.55 | 5.00-85.00 |
| | Optional Acidic agent | 0.00-62.95 | 0.00-20.00 |
| | Optional Lubricant | 0.00-15.74 | 0.00-5.00 |
| Tablet Core Push Layer | Osmotic salt | 20.00-80.00 | 10.00-40.00 |
| | Optional glidant | 0.00-2.00 | 0.00-1.00 |
| | Water swellable polymer | 10.00-170.00 | 5.00-85.00 |
| | Hydrophilic polymer | 4.00-40.00 | 2.00-20.00 |
| | Optional pigment | 0.00-4.80 | 0.00-2.40 |
| | Optional lubricant | 0.00-10.00 | 0.00-5.00 |
| Semipermeable membrane (Coating A) | Film-forming cellulose ester | 15.20-15.84 | 95.00-99.00 |
| | Plasticizer | 0.16-0.08 | 1.00-5.00 |
| IR Coating (Coating B) | Methylphenidate HCL USP | 12.96 | 24.28 |
| | Water soluble polymer | 26.69-40.41 | 50.00-75.72 |
| | Optional acidic agent | 0.00-QS to PH:3 | | wrt denotes "with respect to".

Example 2

The following formula is used to prepare controlled release devices containing MPH in the core. The osmotic device tablets contain the following ingredients in the amounts indicated.

| | Component | Amt (mg) | Amt (% wrt layer) |
|---|---|---|---|

2-A

| | Component | Amt (mg) | Amt (% wrt layer) |
|---|---|---|---|
| Tablet Core-Pull Layer | Methylphenidate HCL USP | 14.76 | 10.35 |
| | Hydrophilic polymer | 2.85-57.05 | 2.00-40.00 |
| | Water swellable polymer | 7.13-135.49 | 5.00-95.00 |
| | Acidic agent | 1.43-35.66 | 1.00-25.00 |
| | Lubricant | 0.36-14.26 | 0.25-10.00 |
| Tablet Core-Push Layer | Osmotic salt | 5.00-50.00 | 5.00-50.00 |
| | Glidant | 0.1-2.00 | 0.1-2.00 |
| | Water swellable polymer | 5.00-90.00 | 5.00-90.00 |
| | Hydrophilic polymer | 2.00-40.00 | 2.00-40.00 |
| | Pigment 1 | 0.35-2.40 | 0.35-2.40 |
| | Lubricant | 0.25-10.00 | 0.25-10.00 |
| Osmotic Coating (Coating A) | Film-forming cellulose ester | 6.00-60.00 | 2.00-20.00 |
| | Plasticizer | 0.15-0.90 | 0.05-0.30 |
| | Solvent 1 | 242.25-282.15 | 85.00-99.00 |
| | Solvent 2 | 2.85-42.75 | 1.00-15.00 |
| IR Coating (Coating B) | Methylphenidate HCL USP | 3.24 | 24.27 |
| | Water soluble polymer | 2.90-14.50 | 3.00-15.00 |
| | Acidic agent | Q.S to PH 3.0 | Q.S to PH 3.0 |
| | Solvent 2 | 77.38-93.78 | 80.00-97.00 |
| Optional Color Coating (Coating C) | Water soluble polymer and dye | 3.00-20.00 | 3.00-20.00 |
| | Solvent 2 | 42.35-137.84 | 80.00-97.00 |
| Optional Printing | Pigment and polymer | Negligible | Negligible |
| | Solvent 3 | Negligible | Negligible |

2-B

| | Component | Amt (mg) | Amt (% wrt layer) |
|---|---|---|---|
| Tablet Core-Pull Layer | Methylphenidate HCL USP | 22.14 | 14.76 |
| | Hydrophilic polymer | 3.00-60.00 | 2.00-40.00 |
| | Water swellable polymer | 7.50-142.5 | 5.00-95.00 |
| | Acidic agent | 1.50-37.50 | 1.00-25.00 |
| | Lubricant | 0.38-15.00 | 0.25-10.00 |
| Tablet Core-Push Layer | Osmotic salt | 5.00-50.00 | 5.00-50.00 |
| | Glidant | 0.10-2.00 | 0.1-2.00 |
| | Water swellable polymer | 5.00-90.00 | 5.00-90.00 |
| | Hydrophilic polymer | 2.00-40.00 | 2.00-40.00 |
| | Pigment 1 | 0.35-2.40 | 0.35-2.40 |
| | Lubricant | 0.25-10.00 | 0.25-10.00 |
| Osmotic Coating (Coating A) | Film-forming cellulose ester | 6.00-60.00 | 2.00-20.00 |
| | Plasticizer | 0.15-0.9 | 0.05-0.30 |
| | Solvent 1 | 242.25-282.15 | 85.00-99.00 |
| | Solvent 2 | 2.85-42.75 | 1.00-15.00 |
| IR Coating (Coating B) | Methylphenidate HCL USP | 4.86 | 24.28 |
| | Water soluble polymer | 4.35-21.75 | 3.00-15.00 |
| | Acidic agent | Q.S to PH 3.0 | Q.S to PH 3.0 |
| | Solvent 2 | 116.01-140.66 | 80.00-97.00 |
| Optional Color Coating (Coating C) | Water soluble polymer and dye | 2.55-17.00 | 3.00-20.00 |
| | Solvent 2 | 36.00-117.17 | 80.00-97.00 |
| Optional Printing | Pigment and polymer | Negligible | Negligible |
| | Solvent 3 | Negligible | Negligible |

2-C

| | Component | Amt (mg) | Amt (% wrt layer) |
|---|---|---|---|
| Tablet Core-Pull Layer | Methylphenidate HCL USP | 29.52 | 10.35 |
| | Hydrophilic polymer | 5.70-114.10 | 2.00-40.00 |
| | Water swellable polymer | 14.26-270.98 | 5.00-95.00 |
| | Acidic agent | 2.85-71.31 | 1.00-25.00 |
| | Lubricant | 0.71-28.52 | 0.25-10.00 |
| Tablet Core-Push Layer | Osmotic salt | 10.00-100.00 | 5.00-50.00 |
| | Glidant | 0.20-4.00 | 0.10-2.00 |
| | Water swellable polymer | 10.00-180.00 | 5.00-90.00 |
| | Hydrophilic polymer | 4.00-80.00 | 2.00-40.00 |
| | Pigment 1 | 0.70-4.80 | 0.35-2.40 |
| | Lubricant | 0.50-20.00 | 0.25-10.00 |
| Osmotic Coating (Coating A) | Film-forming cellulose ester | 6.40-64.00 | 2.00-20.00 |
| | Plasticizer | 0.16-0.96 | 0.05-0.30 |
| | Solvent 1 | 229.69-300.96 | 85.00-99.00 |
| | Solvent 2 | 9.12-31.92 | 1.00-15.00 |
| IR Coating (Coating B) | Methylphenidate HCL USP | 6.48 | 24.27 |
| | Water soluble polymer | 5.80-28.99 | 3.00-15.00 |
| | Acidic agent | Q.S to PH 3.0 | Q.S to PH 3.0 |
| | Solvent 2 | 154.70-187.58 | 80.00-97.00 |
| Optional Color Coating (Coating C) | Water soluble polymer and dye | 4.95-33.00 | 3.00-20.00 |
| | Solvent 2 | 69.88-227.44 | 80.00-97.00 |
| Optional Printing | Pigment and polymer | Negligible | Negligible |
| | Solvent 3 | Negligible | Negligible |

2-D

| | Component | Amt (mg) | Amt (% wrt layer) |
|---|---|---|---|
| Tablet Core-Pull Layer | Methylphenidate HCL USP | 44.28 | 14.76 |
| | Hydrophilic polymer | 6.00-120.00 | 2.00-40.00 |
| | Water swellable polymer | 15.00-251.47 | 5.00-95.00 |
| | Acidic agent | 3.00-75.00 | 1.00-25.00 |
| | Lubricant | 0.75-30.00 | 0.25-10.00 |

| | Component | Amt (mg) | Amt (% wrt layer) |
|---|---|---|---|
| Tablet Core-Push Layer | Osmotic salt | 10.00-100.00 | 5.00-50.00 |
| | Glidant | 0.20-4.00 | 0.1-2.00 |
| | Water swellable polymer | 10.00-180.00 | 5.00-90.00 |
| | Hydrophilic polymer | 4.00-80.00 | 2.00-40.00 |
| | Pigment 1 | 0.70-4.80 | 0.35-2.40 |
| | Lubricant | 0.50-20.00 | 0.25-10.00 |
| Osmotic Coating (Coating A) | Film-forming cellulose ester | 6.80-68.00 | 2.00-20.00 |
| | Plasticizer | 0.17-1.01 | 0.05-0.30 |
| | Solvent 1 | 244.04-319.77 | 85.00-99.00 |
| | Solvent 2 | 3.23-48.45 | 1.00-15.00 |
| IR Coating (Coating B) | Methylphenidate HCL USP | 9.72 | 24.25 |
| | Water soluble polymer | 7.50-37.78 | 3.00-15.11 |
| | Acidic agent | Q.S to PH 3.0 | Q.S to PH 3.0 |
| | Solvent 2 | 238.18-288.80 | 80.00-97.00 |
| Optional Color Coating (Coating C) | Water soluble polymer and dye | 5.10-33.33 | 3.00-20.00 |
| | Solvent 2 | 74.11-241.22 | 80.00-97.00 |
| Optional Printing | Pigment and polymer | Negligible | Negligible |
| | Solvent 3 | Negligible | Negligible |
| 2-E | | | |
| Tablet Core-Pull Layer | Methylphenidate HCL USP | 59.04 | 18.76 |
| | Hydrophilic polymer | 12.03-240.64 | 2.00-40.00 |
| | Water swellable polymer | 30.00-571.55 | 5.00-95.00 |
| | Acidic agent | 3.00-75.00 | 1.00-25.00 |
| | Lubricant | 1.50-60.00 | 0.25-10.00 |
| Tablet Core-Push Layer | Osmotic salt | 10.00-100.00 | 5.00-50.00 |
| | Glidant | 0.60-12.00 | 0.1-2.00 |
| | Water swellable polymer | 30.00-541.47 | 5.00-90.00 |
| | Hydrophilic polymer | 12.03-240.64 | 2.00-40.00 |
| | Pigment 1 | 1.00-6.80 | 0.35-2.40 |
| | Lubricant | 0.50-60.00 | 0.25-10.00 |
| Osmotic Coating (Coating A) | Film-forming cellulose ester | 6.42-64.21 | 2.00-20.00 |
| | Plasticizer | 0.16-0.96 | 0.05-0.30 |
| | Solvent 1 | 229.69-300.96 | 85.00-99.00 |
| | Solvent 2 | 9.12-31.92 | 1.00-15.00 |
| IR Coating (Coating B) | Methylphenidate HCL USP | 12.96 | 24.28 |
| | Water soluble polymer | 11.60-58.44 | 3.00-15.11 |
| | Acidic agent | Q.S to PH 3.0 | Q.S to PH3.0 |
| | Solvent 2 | 309.33-375.06 | 80.00-97.00 |
| Optional Color Coating (Coating C) | Water soluble polymer and dye | 5.25-35.00 | 3.00-20.00 |
| | Solvent 2 | 74.11-241.22 | 80.00-97.00 |
| Optional Printing | Pigment and polymer | Negligible | Negligible |
| | Solvent 3 | Negligible | Negligible | wrt denotes "with respect to".

Example 3

The procedure of Example 1 is followed to prepare an osmotic device comprising a bi-layered core with a MPH-containing first layer and a water swellable second layer. The osmotic device contains the following ingredients in the amounts indicated.

| | Component | Amt (mg) | Amt (% wrt layer) |
|---|---|---|---|
| 3-A | | | |
| Tablet Core-Push Layer | Methylphenidate HCL USP | 14.76 | 10.35 |
| | Hypromellose USP 2208 K100 Premium LVCR | 2.85-28.52 | 2.00-20.00 |
| | Polyethylene Oxide NF (Polyox WSR N80 LEO) | 7.13-121.23 | 5.00-85.00 |
| | Succinic Acid, NF | 7.13-28.52 | 5.00-20.00 |
| | Magnesium Stearate NF | 0.36-7.13 | 0.25-5.00 |
| Pull layer weight | | 142.62 | 50.75 |
| Tablet Core-Push Layer | Sodium Chloride USP | 10.00-40.00 | 10.00-40.00 |
| | Colloidal Silicon Dioxide NF (Aerosil 200) | 0.10-1.00 | 0.10-1.00 |
| | Polyethylene Oxide NF (Polyox WSR 303 LEO) | 5.00-85.00 | 5.00-85.00 |
| | Hypromellose USP 2208 K100 Premium LVCR | 2.00-20.00 | 2.00-20.00 |
| | Ferrosoferric Oxide NF | 0.35-2.40 | 0.35-2.40 |
| | Magnesium Stearate NF | 0.25-5.00 | 0.25-5.00 |
| Push layer weight | | 100.00 | 35.59 |
| Osmotic Coating (Coating A) | Acetate Cellulose NF (CA-398-10) | 8.73-20.37 | 2.91-6.79 |
| | Polyethylene Glycol NF 3350 | 0.27-0.63 | 0.09-0.21 |
| | Acetone NF | 256.50-282.15 | 90.00-99.00 |
| | Purified Water USP | 2.85-28.50 | 1.00-10.00 |
| Osmotic coating weight | | 15.00 | 5.34 |
| IR Coating (Coating B) | Methylphenidate HCL USP | 3.24 | 24.27 |
| | Opadry YS-3-7413 Clear | 7.31-12.42 | 7.56-12.85 |
| | Phosphoric Acid, NF | Q.S to PH 3.0 | Q.S to PH 3.0 |
| | Purified Water USP | 80.25-87.01 | 83.00-90.00 |
| IR coating weight | | 13.35 | 4.75 |
| Color Coating (Coating C) | Opadry II Yellow 32K92800 | 5.00-15.00 | 5.00-15.00 |
| | Purified Water USP | 45-135 | 85.00-95.00 |
| Color coating weight | | | |
| Printing | Opacode WB Black NS-78-17821 | Negligible | Negligible |
| | Isopropyl Alcohol 99% USP | Negligible | Negligible |
| Total weight | | 280.97 | 100.00 |
| 3-B | | | |
| Tablet Core-Push Layer | Methylphenidate HCL USP | 22.14 | 14.76 |
| | Hypromellose USP 2208 K100 Premium LVCR | 3.00-30.00 | 2.00-20.00 |
| | Polyethylene Oxide NF (Polyox WSR N80 LEO) | 7.50-127.50 | 5.00-85.00 |
| | Succinic Acid, NF | 7.50-30.00 | 5.00-20.00 |
| | Magnesium Stearate NF | 0.375-7.50 | 0.25-5.00 |
| Pull layer weight | | 150.00 | 51.10 |
| Tablet Core-Push Layer | Sodium Chloride USP | 10.00-40.00 | 10.00-40.00 |
| | Colloidal Silicon Dioxide NF (Aerosil 200) | 0.1-1.00 | 0.1-1.00 |
| | Polyethylene Oxide NF (Polyox WSR 303 LEO) | 5.00-85.00 | 5.00-85.00 |
| | Hypromellose USP 2208 K100 Premium LVCR | 2.00-20.00 | 2.00-20.00 |
| | Ferrosoferric Oxide NF | 0.35-2.40 | 0.35-2.40 |
| | Magnesium Stearate NF | 0.25-5.00 | 0.25-5.00 |
| Push layer weight | | 100.00 | 34.07 |
| Osmotic Coating (Coating A) | Acetate Cellulose NF (CA-398-10) | 8.73-20.37 | 2.91-6.79 |
| | Polyethylene Glycol NF 3350 | 0.27-0.63 | 0.09-0.21 |
| | Acetone NF | 256.50-282.15 | 90.00-99.00 |
| | Purified Water USP | 2.85-28.50 | 1.00-10.00 |
| Osmotic coating weight | | 15.00 | 5.11 |
| IR Coating (Coating B) | Methylphenidate HCL USP | 4.86 | 24.28 |
| | Opadry YS-3-7413 Clear | 10.97-18.65 | 7.56-12.86 |
| | Phosphoric Acid, NF | Q.S to PH 3.0 | Q.S to PH 3.0 |
| | Purified Water USP | 120.36-130.51 | 83.00-90.00 |
| IR coating weight | | 20.02 | 6.82 |
| Color Coating (Coating C) | Opadry II Yellow 32K92800 | 4.25-12.75 | 5.00-15.00 |
| | Purified Water USP | 38.25-114.75 | 85.00-95.00 |
| Color coating weight | | 8.50 | 2.90 |
| Printing | Opacode WB Black NS-78-17821 | Negligible | Negligible |
| | Isopropyl Alcohol 99% USP | Negligible | Negligible |
| Total weight | | 293.52 | 100.00 |

3-C

| Component | | Amt (mg) | Amt (% wrt layer) |
|---|---|---|---|
| Tablet Core-Push Layer | Methylphenidate HCL USP | 29.52 | 10.35 |
| | Hypromellose USP 2208 K100 Premium LVCR | 5.70-57.00 | 2.00-20.00 |
| | Polyethylene Oxide NF (Polyox WSR N80 LEO) | 14.26-242.45 | 5.00-85.00 |
| | Succinic Acid, NF | 14.26-57.00 | 5.00-20.00 |
| | Magnesium Stearate NF | 0.71-14.26 | 0.25-5.00 |
| Pull layer weight | | 285.24 | 52.39 |
| Tablet Core-Push Layer | Sodium Chloride USP | 20.00-80.00 | 10.00-40.00 |
| | Colloidal Silicon Dioxide NF (Aerosil 200) | 0.2-2.00 | 0.1-1.00 |
| | Polyethylene Oxide NF (Polyox WSR 303 LEO) | 10.00-170.00 | 5.00-85.00 |
| | Hypromellose USP 2208 K100 Premium LVCR | 4.00-40.00 | 2.00-20.00 |
| | Ferrosoferric Oxide NF | 0.70-4.80 | 0.35-2.40 |
| | Magnesium Stearate NF | 0.50-10.00 | 0.25-5.00 |
| Push layer weight | | 200.00 | 36.73 |
| Osmotic Coating (Coating A) | Acetate Cellulose NF (CA-398-10) | 9.31-21.73 | 2.91-6.79 |
| | Polyethylene Glycol NF 3350 | 0.29-0.67 | 0.09-0.21 |
| | Acetone NF | 243.20-300.96 | 90.00-99.00 |
| | Purified Water USP | 9.12-21.28 | 1.00-10.00 |
| Osmotic coating weight | | 16.00 | 2.94 |
| IR Coating (Coating B) | Methylphenidate HCL USP | 6.48 | 24.27 |
| | Opadry YS-3-7413 Clear | 14.62-24.85 | 7.56-12.86 |
| | Phosphoric Acid, NF | QS to PH:3 | QS to PH:3 |
| | Purified Water USP | 160.50-174.04 | 83.00-90.00 |
| IR coating weight | | 26.70 | 4.90 |
| Color Coating (Coating C) | Opadry II Yellow 32K92800 | 8.25-24.75 | 5.00-15.00 |
| | Purified Water USP | 74.25-222.75 | 85.00-95.00 |
| Color coating weight | | 16.50 | 3.03 |
| Printing | Opacode WB Black NS-78-17821 | Negligible | Negligible |
| | Isopropyl Alcohol 99% USP | Negligible | Negligible |
| Total weight | | 544.44 | 100.00 |

3-D

| Component | | Amt (mg) | Amt (% wrt layer) |
|---|---|---|---|
| Tablet Core-Push Layer | Methylphenidate HCL USP | 44.28 | 14.76 |
| | Hypromellose USP 2208 K100 Premium LVCR | 6.00-60.00 | 2.00-20.00 |
| | Polyethylene Oxide NF (Polyox WSR N80 LEO) | 15.00-255.00 | 5.00-85.00 |
| | Succinic Acid, NF | 15.00-60.00 | 5.00-20.00 |
| | Magnesium Stearate NF | 0.75-15.00 | 0.25-5.00 |
| Pull layer weight | | 300.00 | 52.26 |
| Tablet Core-Push Layer | Sodium Chloride USP | 20.00-80.00 | 10.00-40.00 |
| | Colloidal Silicon Dioxide NF (Aerosil 200) | 0.20-2.00 | 0.1-1.00 |
| | Polyethylene Oxide NF (Polyox WSR 303 LEO) | 10.00-170.00 | 5.00-85.00 |
| | Hypromellose USP 2208 K100 Premium LVCR | 4.00-40.00 | 2.00-20.00 |
| | Ferrosoferric Oxide NF | 0.70-4.80 | 0.35-2.40 |
| | Magnesium Stearate NF | 0.50-10.00 | 0.25-5.00 |
| Push layer weight | | 200.00 | 34.84 |
| Osmotic Coating (Coating A) | Acetate Cellulose NF (CA-398-10) | 9.89-23.09 | 2.91-6.79 |
| | Polyethylene Glycol NF 3350 | 0.31-0.71 | 0.09-0.21 |
| | Acetone NF | 258.40-319.77 | 90.00-99.00 |
| | Purified Water USP | 3.23-32.30 | 1.00-10.00 |
| Osmotic coating weight | | 17.00 | 2.96 |
| IR Coating (Coating B) | Methylphenidate HCL USP | 9.72 | 24.25 |
| | Opadry YS-3-7413 Clear | 22.66-37.78 | 9.07-15.11 |
| | Phosphoric Acid, NF | QS to PH:3 | QS to PH:3 |
| | Purified Water USP | 238.18-262.00 | 80.00-88.00 |
| IR coating weight | | 40.08 | 6.98 |
| Color Coating (Coating C) | Opadry II Yellow 32K92800 | 8.50-25.50 | 5.00-15.00 |
| | Purified Water USP | 78.75-236.25 | 85.00-95.00 |
| Color coating weight | | 17.00 | 2.96 |
| Printing | Opacode WB Black NS-78-17821 | Negligible | Negligible |
| | Isopropyl Alcohol 99% USP | Negligible | Negligible |
| Total weight | | 574.00 | 100.00 |

3-E

| Component | | Amt (mg) | Amt (% wrt layer) |
|---|---|---|---|
| Tablet Core-Push Layer | Methylphenidate HCL USP | 59.04 | 10.35 |
| | Hypromellose USP 2208 K100 Premium LVCR | 12.03-120.32 | 2.00-20.00 |
| | Polyethylene Oxide NF (Polyox WSR N80 LEO) | 30.00-511.39 | 5.00-85.00 |
| | Succinic Acid, NF | 15.00-60.00 | 5.00-20.00 |
| | Magnesium Stearate NF | 1.50-30.00 | 0.25-5.00 |
| Pull layer weight | | 314.76 | 52.32 |
| Tablet Core-Push Layer | Sodium Chloride USP | 20.00-80.00 | 10.00-40.00 |
| | Colloidal Silicon Dioxide NF (Aerosil 200) | 0.60-6.00 | 0.1-1.00 |
| | Polyethylene Oxide NF (Polyox WSR 303 LEO) | 30-511.39 | 5.00-85.00 |
| | Hypromellose USP 2208 K100 Premium LVCR | 12.03-120.32 | 2.00-20.00 |
| | Ferrosoferric Oxide NF | 1.00-6.80 | 0.35-2.40 |
| | Magnesium Stearate NF | 0.50-10.00 | 0.25-5.00 |
| Push layer weight | | 200.00 | 33.24 |
| Osmotic Coating (Coating A) | Acetate Cellulose NF (CA-398-10) | 9.31-21.73 | 2.91-6.79 |
| | Polyethylene Glycol NF 3350 | 0.29-0.67 | 0.09-0.21 |
| | Acetone NF | 243.20-300.96 | 90.00-99.00 |
| | Purified Water USP | 9.12-21.28 | 1.00-10.00 |
| Osmotic coating weight | | 16.00 | 2.66 |
| IR Coating (Coating B) | Methylphenidate HCL USP | 12.96 | 24.28 |
| | Opadry YS-3-7413 Clear | 29.28-49.74 | 7.57-12.86 |
| | Phosphoric Acid, NF | QS to PH:3 | QS to PH:3 |
| | Purified Water USP | 320.93-347.99 | 83.00-90.00 |
| IR coating weight | | 53.37 | 8.87 |
| Color Coating (Coating C) | Opadry II Yellow 32K92800 | 8.75-26.25 | 5.00-15.00 |
| | Purified Water USP | 78.75-236.25 | 85.00-95.00 |
| Color coating weight | | 17.50 | 2.96 |
| Printing | Opacode WB Black NS-78-17821 | Negligible | Negligible |
| | Isopropyl Alcohol 99% USP | Negligible | Negligible |
| Total weight | | 601.63 | 100.00 |

Example 4

The dissolution (drug release) profile for the dosage forms described herein is determined according to the method disclosed in Methylphenidate Hydrochloride (MPH-HCl) Extended-Release Tablets USP official monograph (test 2), in 50 mL of acidified water adjusted with phosphoric acid to a pH of 3, at 37±0.5° C., using an Apparatus 7 (USP method <724> entitled "Drug Release") at 30 cycles (dips)/min, 2-3 cm amplitude, using a metal coil (spring) sample holder (FIG. 4d). MPH was quantified by reverse-phase HPLC employing UV-detection at 205 nm using external calibration with 5 mM sodium pentane sulfonate buffer and acetonitrile mixture (70:30).

Example 5

The following procedure was used to prepare bi-layered core osmotic devices according to Example 2 of U.S. Pat. No. 9,144,549.

The pull composition was prepared as follows: first methylphenidate HCl, sorbitol, and 50% of PEO WSRN80 LEO were mixed and screened using a Quadro Comil apparatus with a 1905 um screen to form mix 1. The remaining PEO WSR N80 LEO and HPMC E5 were separately screened using a Quadro Comil apparatus with a 1905 um screen and then mixed to form mix 2. Next mix 1 was added to a V-Blender and blended until uniform, follow by the addition of mix 2 to the blender and blended until uniform. Next the BHT was milled using a Fitz mill with a #0033 screen, then mixed with magnesium stearate and screened through a 40-mesh, then added to the blender and blended until uniform.

The push composition was prepared as follows: PEO WSR 303 LEO and HPMC E5 were separately screened using a Quadro Comil apparatus with a 1905 um screen and then mixed to form mix 1. Next the sodium chloride and the BHT were milled using a Fitz mill with a #0033 screen to form mix 2. Mix 1 was added to a V-Blender and blended until uniform, follow by the addition of mix 2 to the blender and blended until uniform. Next the red ferric oxide and the magnesium stearate were screened through a 40-mesh, then added to the blender and blended until uniform.

The pull composition and the push composition were compressed into tablets on a standard rotary tablet press to form core tablets.

Several lots were manufactured comprising core tablets coated with different semi-permeable membrane coating suspensions containing cellulose acetate (39.8% acetyl content), cellulose acetate (32% acetyl content) and 5% poly(ethylene glycol) (3350 number-average molecular weight) as follows.

Lot P-MTH-01 was manufactured using a semipermeable membrane coating suspension containing acetone:water (85:15) and 5% w/w of solids. The coating suspension was sprayed at 13 g/min. Lot P-MTH-01 was manufactured using 8.5 mm punches.

Lot P-MTH-02A was manufactured using a semipermeable membrane coating suspension containing acetone:water (85:15) and 5% w/w of solids. The coating suspension was sprayed at 18 g/min. Lot P-MTH-02A was manufactured using 7 mm punches.

Lot P-MTH-02B was manufactured using a semipermeable membrane coating suspension containing acetone:water (75:25) and 5% w/w of solids. The coating suspension was sprayed at 16 g/min. Lot P-MTH-02B was manufactured using 7 mm punches.

Lot P-MTH-02C was manufactured using a semipermeable membrane coating suspension containing acetone:water (85:15) and 5% w/w of solids. The coating suspension was sprayed at 13 g/min. Lot P-MTH-02C was manufactured using 7 mm punches.

Example 6

The following procedure was used to prepare bi-layered core osmotic devices OS203-016, OS203-017A, OS203-017B and OS203-017C The pull composition was prepared as follows: first deagglomerated methylphenidate HCl, 34% of PEO WSR N80 LEO and HPMC K100 LV were mixed and screened using a Quadro Comil apparatus with a 1905 um screen to form mix 1. The 66% of PEO WSR N80 LEO and succinic acid were separately screened using a Quadro Comil apparatus with a 1905 um screen and then mixed to form mix 2. Mix 1 was added to a V-Blender and blended until uniform, follow by the addition of mix 2 to the blender and blended until uniform. Next magnesium stearate was screened through a 40-mesh, then added to the blender and blended until uniform.

The push composition was prepared as follows: first PEO WSR 303 LEO and HPMC K100 LV were separately screened using a Quadro Comil apparatus with a 1905 um screen and then mixed to form mix 1. Next NaCl was milled using a Fitz mill with a #0033 screen, then mixed with SiO2 until uniform, and screened using a Quadro Comil apparatus with a 1905 um screen to form mix 2. Then mix 1 was added to a V-Blender and blended until uniform, follow by the addition of mix 2 to the blender and blended until uniform. Next black iron oxide and the magnesium stearate were screened through a 40-mesh, then added to the blender and blended until uniform.

The pull composition and the push composition were compressed into tablets using 10 mm punches on a standard rotary tablet press to form core tablets.

Several lots were manufacture comprising identical core tablets coated with different semi-permeable membrane coating suspensions containing cellulose acetate (39.8% acetyl content) and 5% poly(ethylene glycol) (3350 number-average molecular weight) as follows.

Lot OS203-016 was manufactured using a semipermeable membrane coating suspension containing acetone:water (95:5) and 5% w/w of solids. The coating suspension was sprayed at 13 g/min.

Lot OS203-017A was manufactured using a semipermeable membrane coating suspension containing acetone:water (85:15) and 5% w/w of solids. The coating suspension was sprayed at 13 g/min.

Lot OS203-017B was manufactured using a semipermeable membrane coating suspension containing acetone:water (75:25) and 5% w/w of solids. The coating suspension was sprayed at 16 g/min.

Lot OS203-017C was manufactured using a semipermeable membrane coating suspension containing acetone:water (85:15) and 5% w/w of solids. The coating suspension was sprayed at 18 g/min.

Example 7

The following procedure was used to evaluate ethanol-related dose dumping of osmotic devices.

Testing Conditions: 900 mL, 0.1 N HCl, USP apparatus 2 (paddle) operated at 37° C. @50 rpm, with or without alcohol;
 Test 1: 12 units tested according to the proposed method (with 0.1N HCl), with data collected every 15 minutes for a total of 2 hours
 Test 2: 12 units analyzed by substituting 5% (v/v) of test medium with Alcohol USP and data collection every 15 minutes for a total of 2 hours
 Test 3: 12 units analyzed by substituting 20% (v/v) of test medium with Alcohol USP and data collection every 15 minutes for a total of 2 hours
 Test 4: 12 units analyzed by substituting 40% (v/v) of test medium with Alcohol USP and data collection every 15 minutes for a total of 2 hours.

The data obtained for evaluation of the osmotic device is detailed in the attached figures and above Detailed Description. Even though the figures do not include data for the 5% ethanol and 20% ethanol assays, the data was obtained, and in each case, the ethanol-related dose dumping was lower for the 20% ethanol solutions and lowest for the 5% ethanol solutions.

Example 8

Bioequivalence Study of Methylphenidate Hydrochloride Extended-Release Tablets, 54 Mg, and CONCERTA® Extended-Release Tablets, 54 mg Under Fed and Fasted Conditions The objective of this single-dose, open-label, randomized, four-period, two-treatment replicate design study is to compare the rate of absorption and oral bioavailability of a test formulation of Methylphenidate HCl ER tablet, 54 mg, lot: 15005, manufactured by Osmotica Pharmaceutical Corp. (for Osmotica Kft) to an oral dose of the commercially available comparator, CONCERTA® Extended-release tablet, 54 mg, manufactured by Janssen-Cilag Manufacturing, LLC (for Janssen Pharmaceuticals, Inc.), when administered under fed and fasted conditions. Thirty-six (36) healthy adult subjects were enrolled in this study. Subjects received a single dose of a test formulation of Methylphenidate HCl ER tablet, 54 mg in two periods and a separate single dose of CONCERTA® Extended-release tablet, 54 mg in two periods under fed conditions. There was a 7-day washout between each administration of study treatment.

Blood (plasma) pharmacokinetic characteristics were assessed after each dose of study medication. Blood samples were drawn at 0 (predose) and at 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 11.0, 12.0, 14.0, 16.0, 24.0, and 36.0 hours after dose administration. Plasma samples were analyzed for methylphenidate using a validated LC-MS-MS procedure.

The pharmacokinetic profiles are given in FIG. 2B (fasted conditions) and FIG. 2C (fed conditions).

Example 9

Bioequivalence Study of Methylphenidate Hydrochloride Extended-Release Tablets, 72 Mg, and CONCERTA® Extended-Release Tablets, 2×36 mg, Under Fasted Conditions The objective of this single-dose, open-label, randomized, four-period, two-treatment replicate design study is to compare the rate of absorption and oral bioavailability of a test formulation of Methylphenidate HCl ER tablet, 72 mg, lot: 15010, manufactured by Osmotica Pharmaceutical Corp. (for Osmotica Kft) to an oral dose of the commercially available comparator, CONCERTA® Extended-release tablet, 2×36 mg, manufactured by Janssen-Cilag Manufacturing, LLC (for Janssen Pharmaceuticals, Inc.), when administered under fasted conditions. Sixty (60) healthy adult subjects were enrolled in this study. Subjects were administered either a single 72 mg or 2×36 mg dose of the assigned treatment in a randomized, sequenced fashion. Each drug administration was separated by a washout period of 7 days.

Blood (plasma) pharmacokinetic characteristics were assessed after each dose of study medication. Blood samples were drawn at predose (0 hour) and at 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 11.0, 12.0, 14.0, 16.0, 24.0, and 36.0 hours after study treatment administration. Plasma samples were analyzed for methylphenidate using a validated LC-MS-MS procedure.

The pharmacokinetic profiles are depicted in FIG. 2D.

Example 10

Generalized Procedure for Preparing Osmotic Devices of the Invention

Osmotic devices of the invention were prepared as follows. The pull layer, push layer, semipermeable membrane and exterior drug-containing coating compositions were prepared separately in any order. The bi-layered compressed core was formed and then coated with film-forming composition. The resultant semipermeable membrane was then perforated. A drug-containing coating was applied exterior to the semipermeable membrane.

Pull Layer

A portion of MPH-HCl, a portion of water swellable polymer, and hydrophilic polymer were mixed, milled and screened. Another portion of water swellable polymer and acidic agent were mixed, milled and screened. The above ingredients were blended with lubricant and the blended material was screened.

Preferred materials include PEO as the water swellable polymer, HPMC as the hydrophilic polymer, organic acid as the acidic agent and magnesium stearate as the lubricant. Specific grades if needed are described herein.

Push Layer

Osmotic salt was milled and screened. The osmotic salt and glidant were mixed. A portion of water swellable polymer and hydrophilic polymer were mixed, milled and screened. The above ingredients were blended with pigment and lubricant and the blended material was screened.

Preferred materials include halide salt as the osmotic salt, colloidal silicon dioxide as the glidant, PEO as the water swellable polymer, HPMC as the hydrophilic polymer, and magnesium stearate as the lubricant. Specific grades if needed are described herein.

Compressed Bi-Layered Core

The chamber of a tablet press was loaded with a charge of push layer composition and a charge of pull layer composition. The compositions were compressed to form the bi-layered core.

Semipermeable Membrane

The film-forming composition was formed by mixing plasticizer with water and then adding organic solvent to that mixture until complete dissolution of the plasticizer. The ratio of organic solvent to water is at least 90:10 or at least 95:5. The film-forming cellulose ester is then added to the mixture such that the solids content is less than 10% wt or about 5% wt.

The film-forming composition is sprayed onto the compressed core using a coating pan or other suitable coating equipment until the target weight of coating onto the cores is achieved. The target weight can be as described herein. Water and solvent evaporate during this process.

The semipermeable membrane is then perforated with a laser drill or other such equipment to form a preformed passageway on the face of the pull layer. The diameter of the whole can be as described herein.

Preferred materials include cellulose acetate as the cellulose ester, PEG as the plasticizer, and a volatile organic solvent. Specific grades if needed are described herein.

Drug-Containing Coating

A portion of MPH-HCl, water soluble polymer, and optional acidic agent are mixed, milled and screened. The drug-containing composition is then applied to the semipermeable membrane coated core either by compression or by spray coating. If spray coating is used, then the solids must be mixed with a suitable liquid to enable application.

All values disclosed herein may have standard technical measure error (standard deviation) of ±10%. The term "about" is intended to mean±10%, ±5%, ±2.5% or ±1% relative to a specified value, i.e. "about" 20% means 20±2%, 20±1%, 20±0.5% or 20±0.25%.

It should be noted that, unless otherwise specified, values herein concerning pharmacokinetic or dissolution parameters are typically representative of the mean or median values obtained from evaluation of at least 4, at least 8 or at least 12 of the same dosage forms.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. An osmotic device comprising a core and a semipermeable membrane enclosing the core, wherein the osmotic device provides a release of methylphenidate hydrochloride (MPH-HCl) from the core according to the following release profile when the osmotic device is placed in 40% ethanol in 0.1 N hydrochloric acid at 37±1° C. in a USP Apparatus type 7

| Time (min) | Released (% wt) |
|---|---|
| 15 | <1 |
| 30 | 2-4 |
| 45 | 2.5-4.5 |
| 60 | 3.5-5.5 |
| 75 | 4.7-6.7 |
| 90 | 6.2-8.2 |
| 105 | 7.7-9.7 |
| 120 | 9-11 | wherein the percentage released is based upon the weight of MPH-HCl in the core.

2. The osmotic device of claim 1, wherein the osmotic device provides a release of MPH-HCl from the core according to the following release profile when the osmotic device is placed in 0.1 N hydrochloric acid at 37±1° C. in a USP Apparatus type 7

| Time (min) | Released (% wt) |
|---|---|
| 15 | <1 |
| 30 | 1-3 |
| 45 | 1-3.5 |
| 60 | 2-4 |
| 75 | 3-5 |
| 90 | 5-7 |
| 105 | 6-8 |
| 120 | 7.5-9.5 | wherein the percentage released is based upon the weight of MPH-HCl in the core.

3. The osmotic device of claim 1, wherein the osmotic device provides a release of MPH-HCl from the core according to the following release profile when the osmotic device is placed in water at 37±1° C. in a USP Apparatus type 7

| Time (hr) | Released (% wt) Median or mean range |
|---|---|
| 1 | <10 |
| 2 | 10-30 |
| 4 | 35-60 |
| 6 | 55-85 |
| 8 | 70-100 |
| 10 | 80-100 | wherein the percentage released is based upon the weight of MPH-HCl in the core.

4. The osmotic device of claim 1, wherein the osmotic device comprises a) a bi-layered core comprising:
  a pull layer comprising MPH-HCl, first water swellable poly(alkylene oxide) polymer, first hydrophilic cellulose derivative and acidic agent; and
  a push layer comprising second water swellable poly(alkylene oxide) polymer, second hydrophilic cellulose derivative, and osmotic salt; and
b) a semipermeable membrane enclosing the core and comprising at least one preformed passageway and at least one cellulose acetate polymer.

5. The osmotic device of claim 4, wherein the semipermeable membrane comprises at least one preformed passageway, at least one plasticizer and a single grade of cellulose acetate polymer, wherein the cellulose acetate polymer is characterized by an acetyl content of about 39-40% wt and a hydroxyl content of about 3-4% wt.

6. An osmotic device comprising a core, a semipermeable membrane enclosing the core, and a drug-containing coating exterior to the semipermeable membrane, wherein the osmotic device provides a release of methylphenidate hydrochloride (MPH-HCl) according to one of the following release profiles when the osmotic device is placed in 40% ethanol in 0.1 N hydrochloric acid at 37±1° C. in a USP Apparatus type 7

| Time (min) | released (% wt) Median or mean range | released (% wt) Median or mean range |
|---|---|---|
| 15 | 4-12 | 11-20 |
| 30 | 7-15 | 12-22 |
| 45 | 8-16 | 13-23 |
| 60 | 9-17 | 15-25 |
| 75 | 10-18 | 18-28 |
| 90 | 12-19 | 19-30 |
| 105 | 13-21 | 22-34 |
| 120 | 15-22 | 24-39 | wherein the percentage released is based upon the total weight of MPH-HCl in the osmotic device.

7. The osmotic device of claim 6, wherein the osmotic device provides a release of methylphenidate hydrochloride (MPH-HCl) according to one of the following release profiles when the osmotic device is placed in aqueous 0.1 N hydrochloric acid at 37±1° C. in a USP Apparatus type 7

| Time (min) | released (% wt) Median or mean range | released (% wt) Median or mean range |
|---|---|---|
| 1 | 20-30 | 15-25 |
| 2 | 25-35 | 25-35 |
| 4 | 45-60 | 42-60 |
| 6 | 68-85 | 58-85 |
| 8 | 90-100 | 71-95 |
| 10 | 91-100 | 79-100 | wherein the percentage released is based upon the total weight of MPH-HCl in the osmotic device.

8. The osmotic device of claim 6, wherein the osmotic device comprises a) a bi-layered core comprising:
  a pull layer comprising MPH-HCl, first water swellable poly(alkylene oxide) polymer, first hydrophilic cellulose derivative and acidic agent; and
  a push layer comprising second water swellable poly(alkylene oxide) polymer, second hydrophilic cellulose derivative, and osmotic salt;

b) a semipermeable membrane enclosing the core and comprising at least one preformed passageway, at least one plasticizer and at least one cellulose acetate polymer; and c) a rapid release or immediate release drug-containing coating exterior to the semipermeable membrane and comprising MPH-HCl.

9. The osmotic device of claim 8, wherein the semipermeable membrane comprises at least one preformed passageway, at least one plasticizer and a single grade of cellulose acetate polymer.

10. The osmotic device of claim 9, wherein the cellulose acetate polymer is characterized by an acetyl content of about 39-40% wt and a hydroxyl content of about 3-4% wt.

11. An osmotic device comprising methylphenidate (MPH) or salt thereof, wherein the osmotic device exhibits a less than 1.5-fold ethanol-related increase in the total amount of MPH or salt thereof released from the device during the first 120 minutes when comparing the MPH or salt thereof release rates in aqueous 0.1 N HCl at 37±1° C. and in 40% ethanol in aqueous 0.1 N HCl at 37±1° C.; wherein about 25% to about 35% wt of MPH or salt thereof is released by about 2 hours, about 45% to about 60% wt of MPH or salt thereof is released by about 4 hours, about 65% to about 85% of MPH or salt thereof is released by about 6 hours, about 85% to about 100% wt of MPH or salt thereof is released by about 8 hours and no less than 85% of MPH or salt thereof is released b about 10 hours after placement in an environment of use or after oral administration.

12. The osmotic device of claim 11, wherein the osmotic device exhibits a less than 2-fold ethanol-related increase in the average rate of MPH or salt thereof released from the device during the time period of 15 minutes to 120 minutes when comparing the release rates in aqueous 0.1 N HCl at 37±1° C. and in 40% ethanol in aqueous 0.1 N HCl at 37±1° C.

13. The osmotic device of claim 11, wherein the osmotic device comprises a bi-layered core enclosed within a semipermeable membrane, and wherein:

a) the bi-layered core comprises:
 a pull layer comprising MPH or salt thereof; and
 a push layer comprising at least one water swellable polymer; and b) the semipermeable membrane comprises at least one preformed passageway, at least one plasticizer and at least one cellulose ester.

14. The osmotic device of claim 13, wherein the semipermeable membrane comprises at least one preformed passageway, at least one plasticizer and a single grade of cellulose acetate polymer, and the cellulose acetate polymer is characterized by an acetyl content of about 39-40% wt and a hydroxyl content of about 3-4% wt.

15. The osmotic device of claim 13, wherein the bi-layered core comprises:
 a pull layer comprising MPH or salt thereof, and first water swellable polymer; and
 a push layer comprising second water swellable polymer.

16. The osmotic device of claim 13, wherein
 the pull layer comprises MPH or salt thereof, first water swellable polymer, and first hydrophilic polymer; and
 the push layer comprises second water swellable polymer, and second hydrophilic polymer.

17. The osmotic device of claim 13, wherein
 the pull layer comprises MPH or salt thereof, first water swellable polymer, first hydrophilic polymer and acidic agent; and
 the push layer comprises second water swellable polymer, second hydrophilic polymer, and osmotic salt.

18. The osmotic device of claim 17, wherein the first and second water-swellable polymers are poly(alkylene oxide) polymers and the first and second hydrophilic polymers are hydrophilic cellulose derivatives.

19. The osmotic device of claim 13, wherein
 the pull layer comprises MPH or salt thereof, first water swellable poly(alkylene oxide) polymer, first hydrophilic cellulose derivative and acidic agent; and
 the push layer comprises second water swellable poly(alkylene oxide) polymer, second hydrophilic cellulose derivative, and osmotic salt.

20. The osmotic device of claim 19, wherein the first hydrophilic cellulose derivative is a different type and/or grade than the second hydrophilic cellulose derivative.

21. The osmotic device of claim 19, wherein the first hydrophilic cellulose derivative is the same type and/or grade as the second hydrophilic cellulose derivative.

22. The osmotic device of claim 19, wherein the hydrophilic cellulose derivative is independently selected upon each occurrence from the group consisting of alkylcellulose, hydroxyalkylcellulose and hydroxyalkyl alkylcellulose.

23. The osmotic device of claim 19, wherein the first and second poly(alkylene oxide) polymers are poly(ethylene oxide) polymers.

24. The osmotic device of claim 23, wherein the first water swellable poly(alkylene oxide) polymer has a lower viscosity and molecular weight than the second water swellable poly(alkylene oxide) polymer.

25. The osmotic device of claim 13 further comprising a rapid release or immediate release MPH- or MPH salt-containing coating exterior to the semipermeable membrane.

26. The osmotic device of claim 13, wherein the MPH or salt thereof is divided between the drug-containing coating and the core according to the following proportions: 1-40% wt in the coating and 99-60% wt in the core, 10-40% wt in the coating and 90-60% wt in the core, 15-35% wt in the coating and 85-65% wt in the core, 15-25% wt in the coating and 85-75% wt in the core, 15-20% wt in the coating and 85-80% wt in the core, 20% wt or less in the coating and 80% wt or more in the core, about 18% wt in the coating and about 82% wt in the core, or about 22% wt in the coating and about 78% wt in the coated core.

27. The osmotic device of claim 13, wherein the dosage form exhibits an in vitro release profile selected from any one of the following for MPH or salt thereof released from the core and the exterior drug-containing coating:

| Time (hr) | Deionized water Dissolution (% wt) Median or mean range | Deionized water Dissolution (% wt) Median or mean range | Deionized water Dissolution (% wt) Median or mean range |
| --- | --- | --- | --- |
| 1 | 20-30 | 22-27 | 21-27 |
| 2 | 25-35 | 29-33 | 27-34 |
| 4 | 45-60 | 51-57 | 46-57 |
| 6 | 68-85 | 74-83 | 68-83 |
| 8 | 90-100 | 97-100 | 92-100 |
| 10 | 91-100 | 99-100 | 95-100. |

28. The osmotic device of claim 13, wherein the core exhibits a weight ratio of pull layer to push layer of at least 1, at least 1.1, at least 1.2, at least 1.3 at least 1.4, at least 1.5, at least 1.6, 1.1 to 2, 1.2 to 1.7, 1.3 to 1.7, 1.4 to 1.7, or 1.4-1.6; and not less than 1, not less than 0.9, or not less than 0.8.

29. The osmotic device of claim 6, wherein oral administration in the fasted or fed state of the osmotic device comprising a 54 mg dose of MPH provides a pharmacokinetic profile defined approximately as follows:

| Parameter | Fed | | Fasted | |
|---|---|---|---|---|
| | OSM (mean) | Standard deviation | OSM (mean) | Standard deviation |
| Tmax (h) | 5.7 | 2.3 | 6 | 1 |
| Cmax (ng/mL) | 16 | 4.8 | 15 | 6 |
| $AUC_{inf}$ (h * ng/mL) | 180 | 54 | 180 | 82. |

* * * * *